US009743870B2

(12) United States Patent
Wang et al.

(10) Patent No.: US 9,743,870 B2
(45) Date of Patent: *Aug. 29, 2017

(54) MICRONEEDLE ARRAYS FOR BIOSENSING AND DRUG DELIVERY

(71) Applicants: The Regents of the University of California, Oakland, CA (US); North Carolina State University, Raleigh, NC (US); Sandia Corporation, Albuquerque, NM (US)

(72) Inventors: Joseph Wang, San Diego, CA (US); Joshua Ray Windmiller, Del Mar, CA (US); Roger Narayan, Raleigh, NC (US); Philip Miller, Greensboro, NC (US); Ronen Polsky, Albuquerque, NM (US); Thayne L. Edwards, Albuquerque, NM (US)

(73) Assignees: The Regents of the University of California, Oakland, CA (US); North Carolina State University, Raleigh, NC (US); National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/965,755

(22) Filed: Dec. 10, 2015

(65) Prior Publication Data

US 2016/0095541 A1 Apr. 7, 2016

Related U.S. Application Data

(63) Continuation of application No. 14/342,536, filed as application No. PCT/US2012/053544 on Aug. 31, 2012.

(Continued)

(51) Int. Cl.
*A61B 5/1473* (2006.01)
*A61M 5/158* (2006.01)
(Continued)

(52) U.S. Cl.
CPC ........ *A61B 5/1473* (2013.01); *A61B 5/14514* (2013.01); *A61B 5/14532* (2013.01);
(Continued)

(58) Field of Classification Search
CPC ..... A61B 5/1473; A61B 5/685; A61B 5/4845; A61B 5/14546; A61B 5/14514;
(Continued)

(56) References Cited

U.S. PATENT DOCUMENTS 4,969,468 A 11/1990 Byers et al.
5,035,711 A 7/1991 Aoki et al.
(Continued)

FOREIGN PATENT DOCUMENTS

CN 101068591 11/2007
EP 1187653 3/2010
(Continued)

OTHER PUBLICATIONS

Miller et al. "Integrated Carbon Fiber Electrodes within Hollow Polymer Microneedles for Transdermal Electrochemical Sensing." Biomicrofluidics. Mar. 2011; 5(1): 013415. Published online Mar. 30, 2011.*

(Continued)

*Primary Examiner* — Meredith Weare
(74) *Attorney, Agent, or Firm* — Perkins Coie LLP

(57) ABSTRACT

Methods, structures, and systems are disclosed for biosensing and drug delivery techniques. In one aspect, a device for detecting an analyte and/or releasing a biochemical into a biological fluid can include an array of hollowed needles, in which each needle includes a protruded needle structure (Continued)

including an exterior wall forming a hollow interior and an opening at a terminal end of the protruded needle structure that exposes the hollow interior, and a probe inside the exterior wall to interact with one or more chemical or biological substances that come in contact with the probe via the opening to produce a probe sensing signal, and an array of wires that are coupled to probes of the array of hollowed needles, respectively, each wire being electrically conductive to transmit the probe sensing signal produced by a respective probe.

20 Claims, 27 Drawing Sheets

Related U.S. Application Data

(60) Provisional application No. 61/530,927, filed on Sep. 2, 2011.

(51) Int. Cl.
| | | |
|---|---|---|
| *A61B 5/00* | (2006.01) | |
| *A61B 5/145* | (2006.01) | |
| *G01N 33/487* | (2006.01) | |
| *A61B 5/1486* | (2006.01) | |
| *A61B 5/15* | (2006.01) | |
| *A61B 5/157* | (2006.01) | |
| *A61B 10/00* | (2006.01) | |
| *A61M 5/172* | (2006.01) | |
| *A61M 37/00* | (2006.01) | |

(52) U.S. Cl.
CPC ...... *A61B 5/14546* (2013.01); *A61B 5/14865* (2013.01); *A61B 5/157* (2013.01); *A61B 5/150984* (2013.01); *A61B 5/4845* (2013.01); *A61B 5/685* (2013.01); *A61B 5/6833* (2013.01); *A61B 5/7282* (2013.01); *A61B 10/0045* (2013.01); *A61M 5/158* (2013.01); *A61M 5/1723* (2013.01); *G01N 33/48785* (2013.01); *A61B 2010/008* (2013.01); *A61B 2562/028* (2013.01); *A61B 2562/046* (2013.01); *A61M 2005/1726* (2013.01); *A61M 2037/003* (2013.01); *A61M 2037/0023* (2013.01)

(58) Field of Classification Search
CPC ............... A61B 5/6833; A61B 5/7282; A61B 5/150984; A61B 5/14865; A61B 5/157; A61B 5/14532; A61B 2010/008; A61B 2562/046; A61B 2562/028; A61B 10/0045; A61M 5/1723; A61M 5/158; A61M 2005/1726; A61M 2037/003; A61M 2037/0023; G01N 33/48785
See application file for complete search history.

(56) References Cited

U.S. PATENT DOCUMENTS

| | | | |
|---|---|---|---|
| 5,869,078 A | 2/1999 | Baudino | |
| 6,132,449 A | 10/2000 | Lum et al. | |
| 6,132,755 A | 10/2000 | Eicher et al. | |
| 6,364,890 B1 | 4/2002 | Lum et al. | |
| 6,603,987 B2 | 8/2003 | Whitson | |
| 6,611,707 B1 | 8/2003 | Prausnitz et al. | |
| 7,344,499 B1 * | 3/2008 | Prausnitz | A61B 5/1411 600/309 |
| 7,415,299 B2 | 8/2008 | Zimmermann et al. | |
| 7,473,244 B2 | 1/2009 | Frazier et al. | |
| 7,837,654 B2 | 11/2010 | Shumate et al. | |
| 7,949,382 B2 | 5/2011 | Jina | |
| 8,108,023 B2 | 1/2012 | Mir et al. | |
| 8,110,079 B2 | 2/2012 | Gooding et al. | |
| 8,160,665 B2 | 4/2012 | Mischler et al. | |
| 8,236,368 B2 * | 8/2012 | Jung | A61M 37/0015 427/2.24 |
| 8,257,324 B2 | 9/2012 | Prausnitz et al. | |
| 8,280,476 B2 | 10/2012 | Jina | |
| 8,815,070 B2 | 8/2014 | Wang et al. | |
| 9,387,000 B2 | 7/2016 | Corrie et al. | |
| 9,551,698 B2 | 1/2017 | Huys et al. | |
| 2003/0104119 A1 | 6/2003 | Wilson et al. | |
| 2003/0135158 A1 | 7/2003 | Gonnelli | |
| 2003/0208167 A1 | 11/2003 | Prausnitz et al. | |
| 2004/0065158 A1 * | 4/2004 | Schrepfer | A61B 5/05 73/864.81 |
| 2005/0137536 A1 | 6/2005 | Gonnelli | |
| 2006/0264716 A1 | 11/2006 | Zander et al. | |
| 2007/0170054 A2 * | 7/2007 | Wilsey | C12Q 1/001 204/403.01 |
| 2007/0282246 A1 | 12/2007 | Henley | |
| 2008/0009800 A1 * | 1/2008 | Nickel | A61M 37/0015 604/173 |
| 2008/0009801 A1 | 1/2008 | Nickel | |
| 2008/0033269 A1 * | 2/2008 | Zhang | A61B 5/14532 600/347 |
| 2008/0097352 A1 | 4/2008 | Beck et al. | |
| 2008/0154107 A1 | 6/2008 | Jina | |
| 2008/0221408 A1 | 9/2008 | Hoarau et al. | |
| 2008/0234562 A1 | 9/2008 | Jina | |
| 2009/0069651 A1 | 3/2009 | Zimmermann et al. | |
| 2009/0069697 A1 | 3/2009 | Frazier et al. | |
| 2009/0084678 A1 | 4/2009 | Joshi | |
| 2009/0131778 A1 | 5/2009 | Jina et al. | |
| 2009/0218239 A1 | 9/2009 | Gooding et al. | |
| 2009/0259118 A1 * | 10/2009 | Feldman | A61B 5/14532 600/345 |
| 2010/0049021 A1 | 2/2010 | Jina et al. | |
| 2011/0077490 A1 * | 3/2011 | Simpson | A61B 5/14532 600/345 |
| 2011/0105871 A1 | 5/2011 | Zimmermann et al. | |
| 2011/0140703 A1 | 6/2011 | Chiao et al. | |
| 2011/0230736 A1 * | 9/2011 | Tepper | A61B 5/14532 600/309 |
| 2011/0237925 A1 | 9/2011 | Yue et al. | |
| 2011/0247934 A1 | 10/2011 | Wang et al. | |
| 2011/0306853 A1 * | 12/2011 | Black | A61B 5/1468 600/309 |
| 2012/0037515 A1 * | 2/2012 | Solanki | C12Q 1/6825 205/780.5 |
| 2012/0172692 A1 | 7/2012 | Tamada et al. | |
| 2013/0053660 A1 | 2/2013 | Shieh | |
| 2013/0065257 A1 | 3/2013 | Wang et al. | |
| 2013/0135158 A1 | 5/2013 | Faroane et al. | |
| 2013/0158376 A1 | 6/2013 | Hayter et al. | |
| 2013/0225956 A1 | 8/2013 | Huang et al. | |
| 2013/0281808 A1 | 10/2013 | Shieh | |
| 2014/0336487 A1 | 11/2014 | Wang et al. | |
| 2015/0276758 A1 | 10/2015 | Addisu | |
| 2015/0313527 A1 | 11/2015 | Renlund | |
| 2016/0029937 A1 | 2/2016 | Sia et al. | |
| 2016/0058342 A1 | 3/2016 | Maiz-Aguinaga et al. | |
| 2016/0095541 A1 | 4/2016 | Wang et al. | |
| 2016/0296149 A1 | 10/2016 | Polsky et al. | |
| 2016/0302687 A1 | 10/2016 | Lee et al. | |
| 2017/0007813 A1 | 1/2017 | Negi et al. | |

FOREIGN PATENT DOCUMENTS

| | | | |
|---|---|---|---|
| EP | 1187653 B1 | 3/2010 | |
| JP | H0231741 A | 2/1990 | |
| JP | H07275227 A | 10/1995 | |
| JP | 2003038464 A | 2/2003 | |
| JP | 2003038465 A | 2/2003 | |
| JP | 2005087613 A | 4/2005 | |
| JP | 2005510467 A | 4/2005 | |
| JP | 2005525141 A | 8/2005 | |
| JP | 2005322591 A | 11/2005 | |

(56) References Cited

FOREIGN PATENT DOCUMENTS

| JP | 2008512162 A | 4/2008 | |
|---|---|---|---|
| JP | 2008540013 A | 11/2008 | |
| WO | 2006060106 | 6/2006 | |
| WO | 2006116242 A2 | 11/2006 | |
| WO | 2010022252 | 2/2010 | |
| WO | 2010120364 A2 | 10/2010 | |
| WO | WO 2010/120364 A2 * | 10/2010 | ........... C12Q 1/6825 |

OTHER PUBLICATIONS

Extended European Search Report for European Patent Application No. 12842020.5, dated May 8, 2015, 7 pages.

G. Jeon, S. Y. Yang, J. Byun, and J. K. Kim, "Electrically Actuatable Smart Nanoporous Membrane for Pulsatile Drug Release", Nano Lett., 2011, 11, 1284-1288.

Han, I. H., Authorized Officer, Korean Intellectual Property Office, International Search Report and Written Opinion, International Application No. PCT/US2012/053544, dated Jun. 27, 2013, 21 pages.

J. R. Windmiller, N. Zhou, M. C. Chuang, G. V. Ramirez, P. Santhosh, P. R. Miller, R. Narayan, and J. Wang, "Microneedle array-based carbon paste amperometric sensors and biosensors", Analyst, 2011, DOI: 10.1039/c1an00012h.

Office Action for Chinese Patent Application No. 201280053416.9, dated Aug. 14, 2015, 14 pages.

S. D. Gittard, A. Ovsianikov, N. A. Monteiro-Riviere, J. Lusk, P. Morel, P. Minghetti, C. Lenardi, B. N. Chichkov, and R. J. Narayan, "Fabrication of Polymer Microneedles Using a Two-Photon Polymerization and Micromolding Process", J. Diabetes Sci. Technol., 2009, 3, 304-311.

Office Action for Japanese Patent Application No. 2014-528676, dated Jul. 19, 2016, 15 pages, with English translation.

Patent Examination Report for Australian Patent Application No. 2012326664, dated Feb. 29, 2016, 3 pages.

Miller et al. "Integrated carbon fiber electrodes within hollow polymer microneedles for transdermal electrochemical sensing," BioMicrofluidics 5, 2011, 14 pages.

J. R. Windmiller, et al. "Bicomponent microneedle array biosensor for minimally-invasive glutamate monitoring", submitted to Electroanal., 2011, xxxx pages.

J. R. Windmiller, et al. "Bicomponent microneedle array biosensor for minimally-invasive glutamate monitoring", submitted to Electroanal., 2011, 8 pages.

* cited by examiner

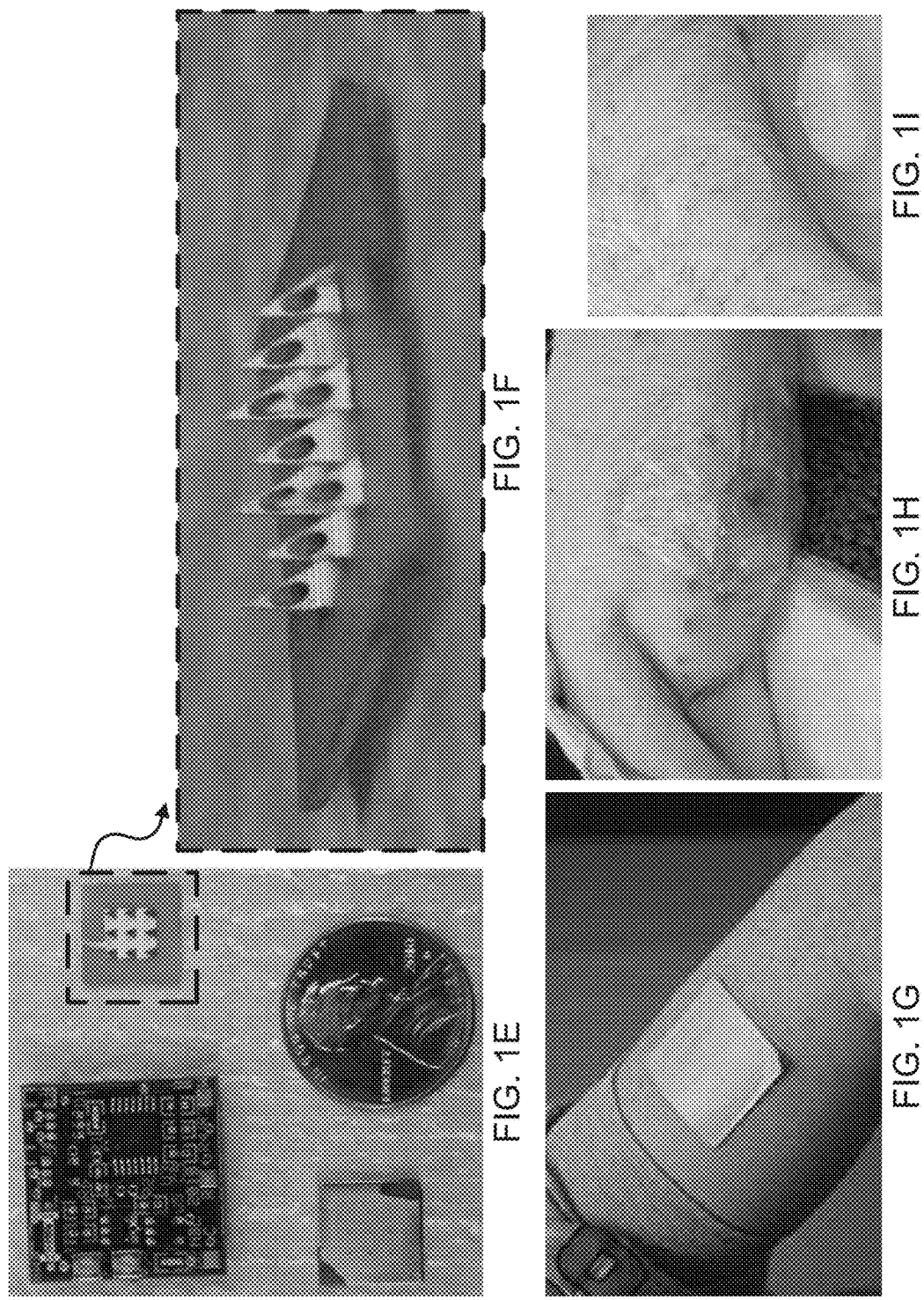

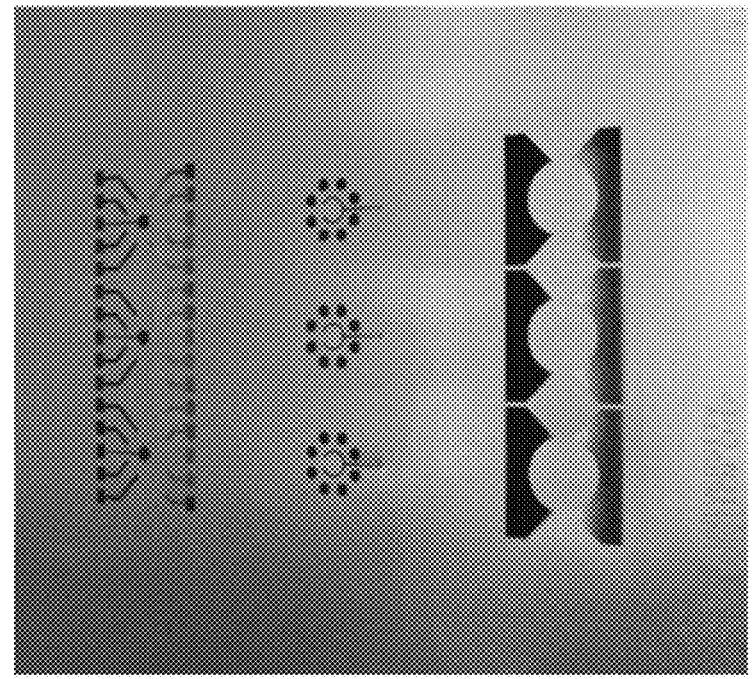
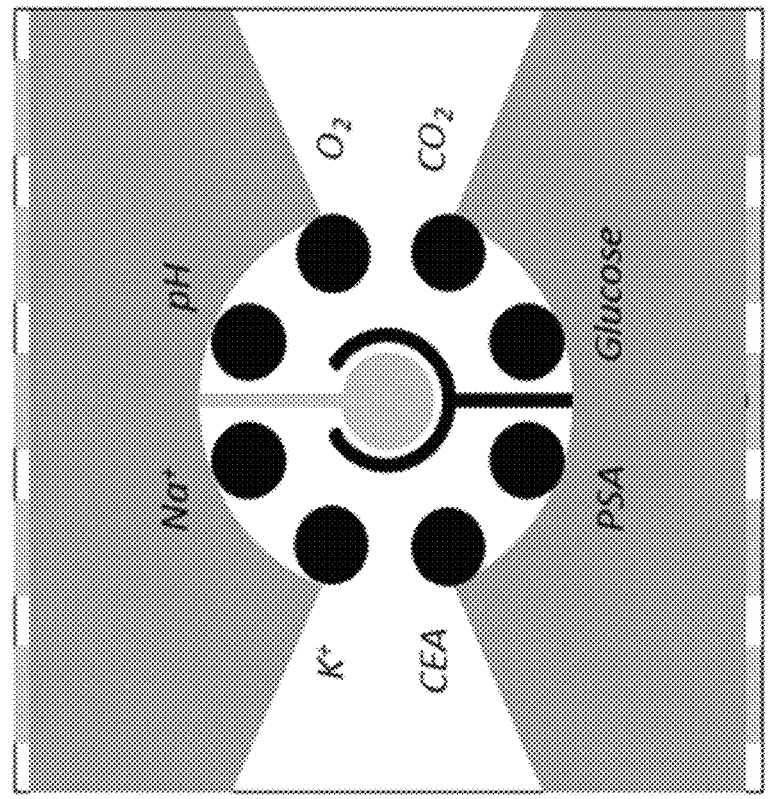
FIG. 4A
FIG. 4B

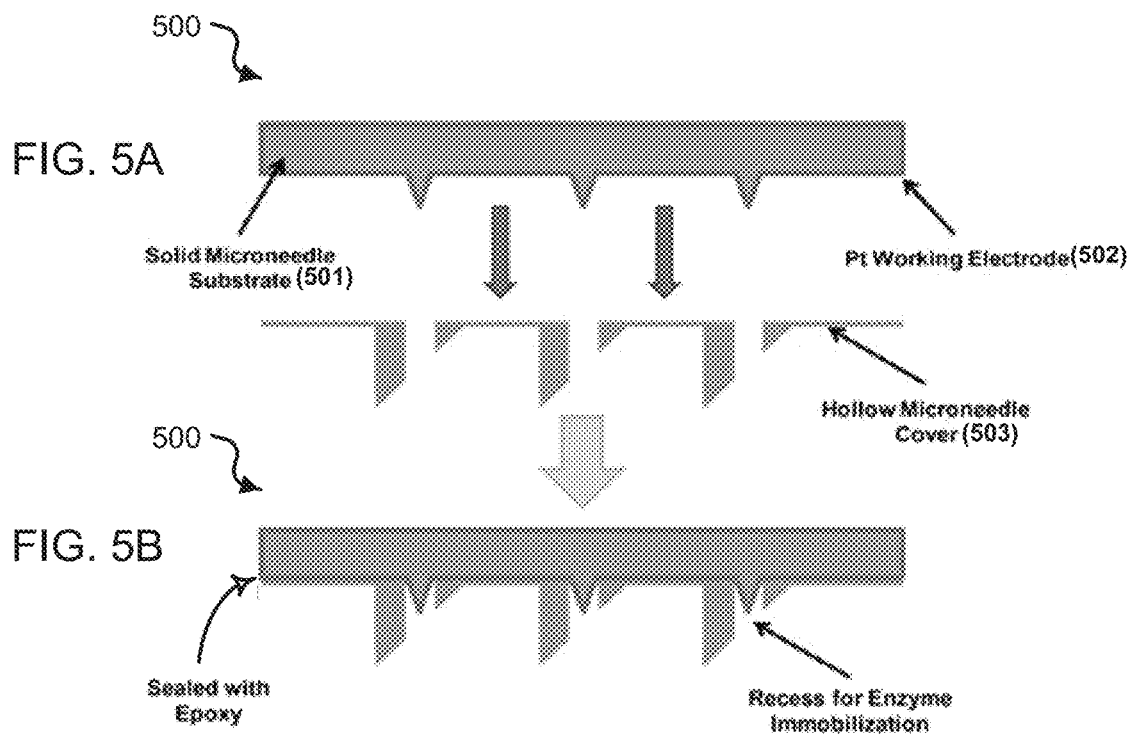
FIG. 5A
FIG. 5B
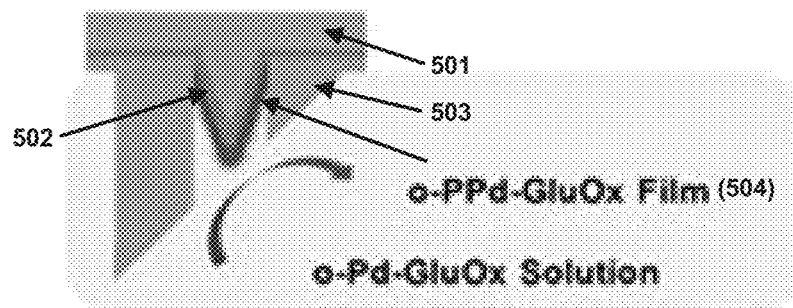
FIG. 5C
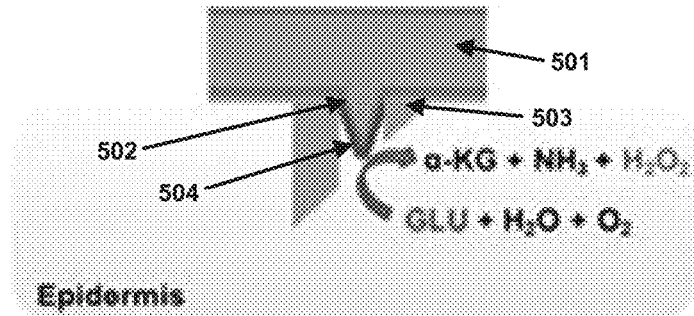
FIG. 5D

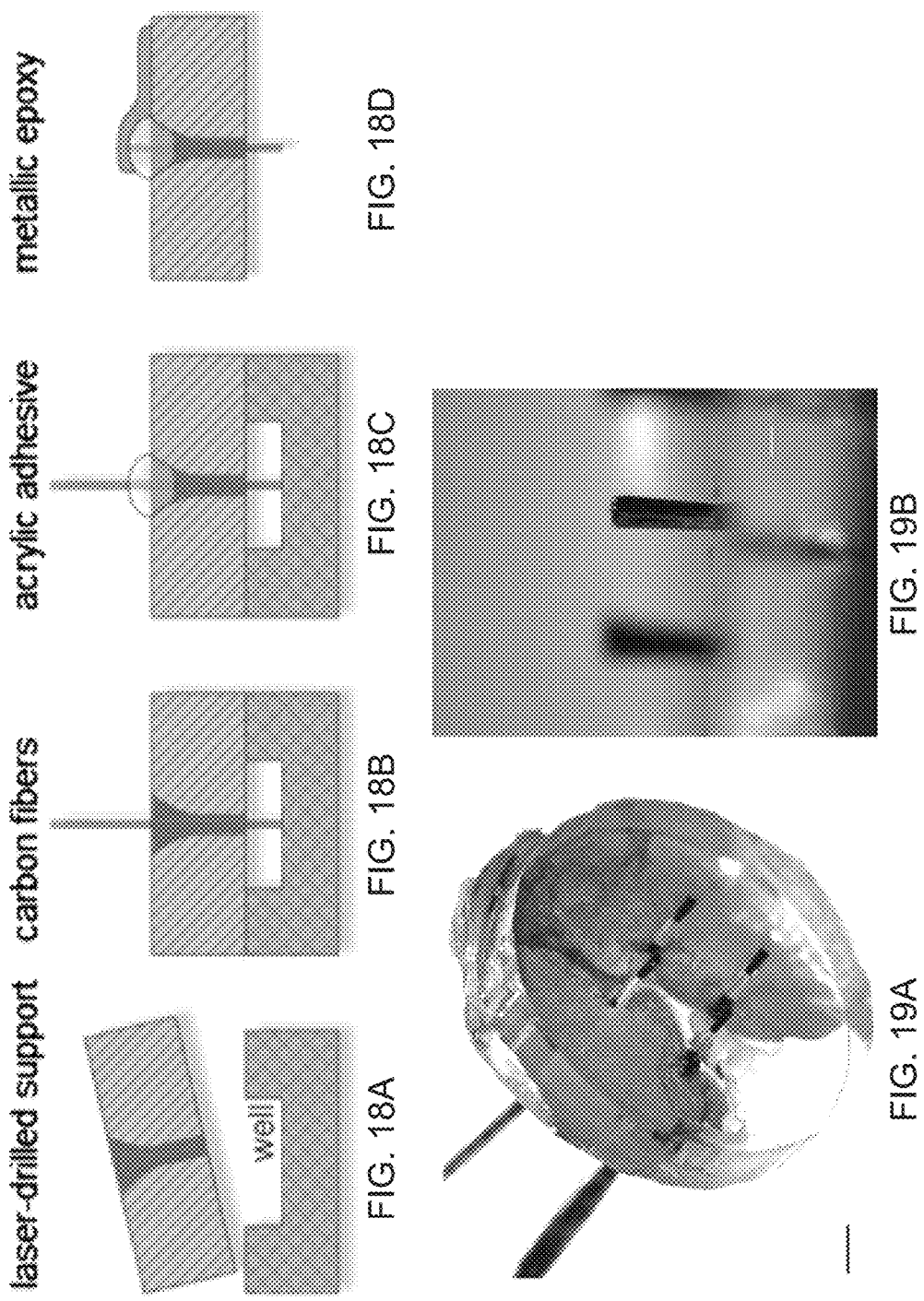

MICRONEEDLE ARRAYS FOR BIOSENSING AND DRUG DELIVERY

CROSS REFERENCE TO RELATED APPLICATIONS

This patent application is a continuation of, and claims priority and benefits of, U.S. patent application Ser. No. 14/342,536 filed Jul. 30, 2014, which is a 35 USC §371 National Stage application of International Application No. PCT/US2012/053544 filed Aug. 31, 2012, which further claims the benefit of priority of U.S. Provisional Application No. 61/530,927, filed on Sep. 2, 2011. The entire content of the before-mentioned patent applications is incorporated by reference as part of the disclosure of this application.

STATEMENT REGARDING FEDERALLY SPONSORED RESEARCH OR DEVELOPMENT

This invention was made with government support under grants no. N00014-08-1-1202 awarded by the Office of Naval Research (ONR), grant no. DE-AC04-94AL85000 awarded by the U.S. Department of Energy to Sandia Corporation, and grant no. 151337 awarded by Sandia National Laboratories Laboratory Directed Research and Development (LDRD). The government has certain rights in the invention.

TECHNICAL FIELD

This patent document relates to biosensors and drug delivery devices.

BACKGROUND

Sensing biological events in vitro and in vivo can provide real-time detection of physiologically relevant compounds, such as monitoring of metabolites, electrolytes, biochemicals, neurotransmitters, medically relevant molecules, cancer biomarkers, and pathogenic microorganisms. Devices that perform such biological event sensing are known as biosensors, which can provide real-time detection of physiological substances and processes in living things. A biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Examples can include evaluating physiologic and pathologic activity within a tissue, as well as drug discovery and drug screening. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

SUMMARY

Techniques, systems, and devices are disclosed for biosensing and therapeutic interventions.

In one aspect of the disclosed technology, a device includes an array of hollowed needles, in which each needle includes a protruded needle structure including an exterior wall forming a hollow interior and an opening at a terminal end of the protruded needle structure exposing the hollow interior, and a probe inside the exterior wall to interact with one or more chemical or biological substances that come in contact with the probe via the opening to produce a probe sensing signal, and an array of wires that are coupled to the probes of the array of hollowed needles, respectively, each wire being electrically conductive to transmit the probe sensing signal produced by a respective probe.

Implementations can optionally include one or more of the following features. For example, the one or more of the probes can include a functionalized coating configured to interact with an analyte within a fluid. An electrochemical interaction between the analyte and the coating on one of the one or more functionalized probes can be detected using at least one of amperometry, voltammetry, or potentiometry. The device can further include a processing unit in communication with the array of wires that receives the probe sensing signals and uses the probe sensing signals as data. The processing unit can compare the data to a threshold value to determine whether the analyte concentration reflects a healthy or disease state. The processing unit can determine a pattern in the data that indicates whether the analyte concentration reflects a healthy or disease state. The processing unit can multiplex the received probe sensing signals from the probes. The device can be integrated into an adhesive patch for placement on skin to detect the analyte residing in transdermal fluid.

In another aspect of the disclosed technology, a device includes a substrate that includes a microneedle with a hollowed interior located on one side of the substrate, in which the microneedle includes a wall with an opening to the hollowed interior, an electrode including a probe, in which the probe is disposed inside the hollowed interior, and a wire that is connected to the probe, in which the electrode is functionalized by a coating over the probe to interact with an analyte to produce an electrical signal.

Implementations can optionally include one or more of the following features. For example, an electrochemical interaction between the analyte and the coating on the functionalized electrode can be detected using at least one of amperometry, voltammetry, or potentiometry. The device can further include a processing unit in communication with the wire that receives the electrical signal and uses the electrical signal as data. The processing unit can compare the data to a threshold value to determines whether the analyte concentration reflects a healthy or disease state. The processing unit can determine a pattern in the data that indicates whether the analyte concentration reflects a healthy or disease state. The device can be integrated into an adhesive patch for placement on skin to detect the analyte residing in transdermal fluid. The device can further can include a polymer film having pores of a reversibly tunable porosity, in which the polymer film is attached to an opposite side of the substrate, a protrusion structure configured on the one side of the substrate, in which the protrusion structure has a channel between an opening in the substrate exposing the polymer film and an opening at a terminal end of the protrusion structure, a containment structure that contains a chemical substance, in which the containment structure includes one or more openings attached to the polymer film positioned above the protrusion structure, and an electrode attached to the polymer film, in which the electrode provides an electrical stimulus to trigger an expansion of the pores of the polymer film to an open state or a contraction the pores of the polymer film to a closed state. The processing unit can be in communication with the wire that receives the electrical signal to use as data and in communication with the electrode to generate the electrical stimulus. The processing unit can process the data to determine whether the analyte concentration reflects a healthy or disease state. The processing unit can actuate the electrode to apply an electrical stimulus to the polymer film to alter its permeability from the closed state to the open state, thereby releasing the chemical substance from the device. The processing unit can multiplex the received electrical signals and the actuation of the electrical stimuli.

In another aspect, a method to sense an analyte and deliver a therapeutic agent includes detecting a signal produced by an analyte at an interface with a chemically functionalized probe configured to electrochemically interact with the analyte within a biological fluid, in which the signal is transduced to an electrical signal by the chemically functionalized probe, processing the electrical signal to determine a parameter of the analyte, and based on the determined parameter, applying an electrical stimulus to a valve comprising a porous polymer film having pores of a reversibly tunable porosity, the valve attached to a container containing a therapeutic agent, in which the electrical stimulus alters the permeability of the pores from a closed state to an open state, thereby releasing the therapeutic agent into the biological fluid.

In another aspect, a device includes a substrate that includes a plurality of microneedles with a hollowed interior located on one side of the substrate, in which each of the microneedles includes a wall with an opening to the hollowed interior, a biosensor module, an actuator module, and a processing unit in communication with the plurality of wires to receive the electrical signal and use the received electrical signal as data, in which the processing unit is in communication with the actuator electrode to generate the electrical stimulus based on the data. The biosensor module includes a plurality of sensing electrodes disposed inside the hollowed interior of a first group of the plurality of microneedles, the sensing electrodes including a probe, in which the probe includes a functionalized coating configured to interact with an analyte within a fluid to produce an electrical signal, and a plurality of wires, in which one wire of the plurality of wires is connected to the probe of the sensing electrodes. The actuator module includes a polymer film having pores of a reversibly tunable porosity, in which the polymer film is attached to an opposite side of the substrate, a plurality of protrusion structures disposed inside the hollowed interior of a second group of the plurality of microneedles, in which the protrusion structures includes a channel between an opening in the substrate exposing the polymer film and an opening at a terminal end of the protrusion structure, a containment structure that contains a chemical substance positioned above the polymer film, in which the containment structure includes one or more openings coupled to the polymer film positioned above the protrusion structure, and an actuator electrode attached to the polymer film, in which the actuator electrode provides an electrical stimulus to trigger an expansion of the pores of the polymer film to an open state or a contraction the pores of the polymer film to a closed state.

Implementations can optionally include one or more of the following features. For example, the processing unit can compare the data to a threshold value to determines whether the analyte concentration reflects a healthy or disease state. The processing unit can determine a pattern in the data that indicates whether the analyte concentration reflects a healthy or disease state. The processing unit can actuate the actuator electrode to apply the electrical stimulus to the polymer film to alter its permeability from the closed state to the open state, thereby releasing the chemical substance into the fluid. The processing unit can multiplex the received electrical signals from the probe and the actuation of the electrical stimuli to the actuator electrode. The processing unit can include logic gates configured on the substrate. The device can be integrated into an adhesive patch for placement on skin to detect the analyte residing in transdermal fluid.

The subject matter described in this patent document can be implemented in specific ways that provide one or more of the following features. Microneedle array devices and techniques are described for performing multiplexed sensing applications and/or drug delivery in an autonomous, minimally-invasive, and controlled manner. For example, the disclosed technology can be implemented to detect analytes in living things via electrochemical methods using microneedle arrays that can be integrated into a patch and applied to the skin. Biosensing can be implemented directly at the microneedle-transdermal interface without the uptake and subsequent processing of biological fluids. Potentiometric, voltammetric, and amperometric techniques can be used to transduce physiological and biochemical information using the microneedle array platform, which can be integrated into one, all-inclusive platform to enable direct biosensing of multiple analytes in bodily fluids. Additionally, the biosensing functionality can be coupled with actuation functionality. For example, a therapeutic agent (e.g., drugs, vaccines, insulin, hormones, vitamins, anti-oxidants, and other pharmacological agents) delivery feature can be initiated by stimuli-responsive conducting polymer nanoactuators. The biosensor-actuator platform can be integrated on an adhesive patch to monitor key physiological/biochemical parameters and/or deliver a therapeutic intervention on demand. The adhesive patch can be integrated with electronics to allow signal transduction and communication. The technology can be used as a "sense" constituent and as a "treat" constituent in an exemplary "Sense-Act-Treat" feedback loop process, which can be utilized in a variety of applications that can include, at least, wireless healthcare, personalized medicine, health profiling, performance/health monitoring, and athlete/warfighter monitoring.

For example, the disclosed technology can have wide-ranging applications within a multitude of fields and disciplines where the assessment of health in real-time is desired. For example, the technology can be easily applied for use in the generalized healthcare, fitness, sport, remote monitoring, wireless healthcare, personalized medicine, performance/health monitoring, and warfighter monitoring domains. The minimally-invasive nature of the technology, combined with its robust architecture, can make the technology well-suited for diverse biomedical monitoring applications, e.g., obtaining biomarker signatures for health profiling, or patterns of bioanalytes as a measure of performance/fitness. As another example, cancer cells, such as melanoma, are known to undergo increased levels of glycolysis which cause localized environments of decreased pH and glucose concentrations, and increased lactate concentrations; thus the disclosed technology can simultaneously and locally detect glucose, lactate, and pH, thereby can be used as a point-of-care clinical diagnostic device to determine if skin cells are cancerous and give immediate data before a lengthy biopsy can be performed. For example, when the technology is used as the "sense" constituent in the exemplary 'Sense-Act-Treat' feedback loop, the technology can be employed as an element of a smart patch that is able to trend pertinent physiological/biochemical information for high-risk patients (e.g., stroke, cardiac, etc.). Moreover, for example, this feature of the technology can be adapted as a "battlefield hospital-on-a-patch" that is able to determine the occurrence of acute injury/trauma and alert the appropriate personnel to instigate a rapid evacuation of the individual and begin a targeted treatment regimen. When the technology is used as the "treat" constituent in the exemplary 'Sense-Act-Treat' feedback loop, the technology can be employed as an element of the smart patch that is able to provide a targeted therapy for acute events experienced by high-risk patients (stroke, cardiac, etc.). These exemplary features can be adapted as a "battlefield hospital-on-a-patch" that is able to begin a treatment regimen in combat situations where the rapid evacuation and treatment of injured personnel is not feasible.

BRIEF DESCRIPTION OF THE DRAWINGS

FIGS. 1D-1F show images of an exemplary microneedle and microneedle array.

FIGS. 1G-1I show images of an exemplary microneedle array device on an adhesive patch implemented on a living being.

FIGS. 4A and 4B show exemplary microneedle arrays fabricated using screen printing and stencil processes to create a pattern.

FIG. 5A shows an illustration of an exemplary process to fabricate an exemplary bicomponent microneedle electrode array using solid and hollow microneedle constituents.

FIG. 5B shows a schematic of the exemplary bicomponent microneedle electrode array fully-assembled.

FIG. 5C shows an illustration of an exemplary process to grow a glutamate oxidase (GluOx)-functionalized poly(o-phenylenediamine) (PPD) film at the solid microneedle surface.

FIG. 5D shows an illustration of the biocatalytic behavior of the exemplary electropolymerized glutamate oxidase-poly(o-phenylenediamine) film.

FIGS. 18A-18D show illustrative schematics showing processing steps for the assembly of an exemplary microneedle array device.

FIGS. 19A and 19B show optical images of an array of carbon fiber electrodes and a single carbon fiber electrode.

DETAILED DESCRIPTION

Figure 1A:
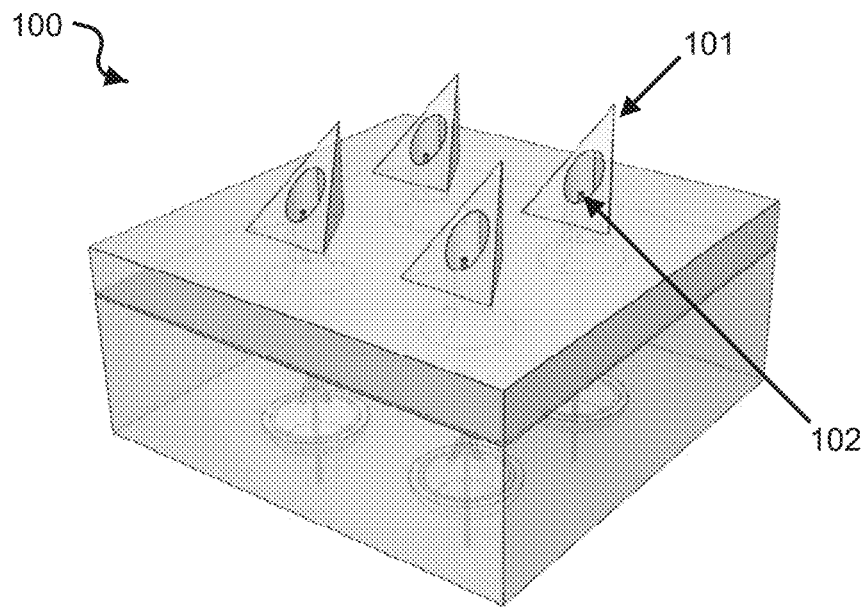
FIGS. 1A-1C show schematics of an exemplary microneedle array device.

Techniques, systems, and devices are disclosed for the detection of analytes and delivery of therapeutic compounds in living things using microneedle array based biosensors and actuators.

In one aspect, the present technology includes a device using an array of microscale structures that penetrate the surface of a biological tissue to detect fluctuations in certain biomarkers in tissue fluids and/or extracellular fluids. By detecting such fluctuations, the devices can be used to monitor progression of diseases, illnesses, and acute injuries, among other conditions. For example, this can be implemented by loading the microstructures with electrochemical transducers in the form of microscale needles, e.g., also referred to as microneedles, microprobes, electrodes, or probes, which can have different chemical functionalities towards biochemical and physiological analytes, e.g., such as a biochemical, metabolite, electrolyte, ion, pathogen, microorganism, etc. For example, the device can employ various electrochemical techniques to perform electrochemical reactions directly at the microneedle/fluid interface and transduce that biochemical information into an electrical signal (e.g., voltammetric, potentiometric, amperometric, conductometric, and/or impedimetric), which can be further processed. For example, each microneedle in an array can be configured to detect a different analyte and multiplexed to be addressed by one or more transduction modalities, e.g., such as an N-array of microneedle elements, in which each element N1 senses glucose, N2 senses lactate, element N3 senses fatty acids, etc., and each analyte is transduced using any or all of voltammetric, potentiometric, amperometric, conductometric, and/or impedimetric techniques.

The device can also be used to implement a therapeutic intervention that utilizes the microneedles to release a chemical agent (e.g., a drug) into the fluid in a controlled manner at a particular localized area in which the microneedle has been applied. The delivery of a targeted therapeutic intervention can be implemented in response to an acute event or based on a chronic condition, e.g., monitored by the sensing contingent of the device. The microneedle array can be configured in conjunction with a permeability-tunable conducting polymer material to control the porosity of the polymer. For example, the device can be configured to include one or more reservoirs containing the chemical agents(s) coupled to the permeability-tunable conducting polymer material that is positioned between the reservoir(s) and the substrate of the microneedle array. Under certain electrochemical stimuli, the polymer material can selectively be made porous (e.g., change the porosity of the polymer material), which can effectively act as a valve that can be selectively opened or closed to transport the chemical agent from the reservoir through the microneedle (lumen) and subsequently into the tissue fluid. The chemical agent release mechanism is electrochemically enabled, e.g., without moveable parts or microelectromechanical (MEMS) components.

The actuation of the therapeutic contingent of the exemplary device can be controlled using an integrated logic system or processing unit, which can provide an electrical stimulus based on feedback from the sensing contingent of the exemplary device. For example, the described sensing contingent of the exemplary device can continuously monitor a concentration level (e.g., based on fluctuations in an average level, a maximum or minimum threshold level, etc.) of a particular analyte associated with normal function or dysfunction indicative of diseases, illnesses, and acute injuries or other conditions and transduce the detected biochemical information associated with the analyte into an electrical signal. The electrical signal can be processed using a processing unit, which can include, at least, a processor and a memory coupled to the processor. For example, the memory may encode one or more programs that cause the processor to perform one or more of the method acts described in this patent document, e.g., including storing the detected signals, analyzing the detected and/or stored signals against other stored values (e.g., such as analyte threshold values indicative of a healthy or dysfunctional state) and/or determining whether or not to release a chemical agent using the therapeutic contingent of the exemplary device. For example, the processing unit may determine the detected analyte level has exceeded a threshold value stored in the memory, and subsequently activate the described actuator to release a drug in response to the determined analyte level. For example, this can be performed by applying a suitable redox potential, the exemplary device can "open" and "close" the described polymer in a reversible manner by changing the intrinsic porosity of the matrix, thus triggering the flux of medication from an on-body reservoir directly into the transdermal fluid. Multivariate/multiplexed drug delivery can be used to implement a therapy in a unique manner, where drugs can be delivered at each microneedle constituent of the array. For example, owing to the arrayed nature of the microneedle structures, multivariate/multiplexed drug delivery can be realized, and a unique analyte can be detected at each microneedle constituent of the array or multiple analytes can be detected at each individual needle through an array of electrodes within a needle. Moreover, the arrayed nature of an exemplary system can enable the device to tailor the cocktail of drugs to mitigate various forms of injury/trauma. Furthermore, the ability to selectively control the porosity of the membrane by adjusting the applied redox potential can imply that the flux rate, and hence the dosage, can be controlled as needed via the integrated biosensor and/or the logic-gate sensing and processing unit.

In some examples, the described microneedle biosensor-actuator technology can be implemented transdermally by applying an exemplary microneedle device to the skin. In other examples, the described microneedle biosensor-actuator technology can be implemented in vivo to other organs within the body, e.g., including the liver, the sclera of the eye, etc. In an example of the biosensing functionality of the disclosed technology, a device can include an array of microneedles sensor-actuators integrated on a skin adhesive patch and applied to the skin of a living being to transdermally monitor physiological and biochemical parameters (e.g., glucose). In an example of blood glucose monitoring, the microneedles can be functionalized with glucose oxidase enzyme (a biocatalyst) that is entrapped within a conducting polymer, e.g., in which the electrode component is conductive and functionalized (e.g., coated) to include the biocatalyst. Upon application of the patch to the skin, the microneedles penetrate the skin so that extracellular fluid (e.g., blood) can diffuse into the microneedle. The biocatalyst, as glucose diffuses into, can convert the glucose substrate into gluconic acid. In the meantime, since the conversion of glucose into gluconic acid is an oxidation-reduction (redox) reaction (e.g., oxidizing glucose), reduction also occurs to oxygen and water naturally present in the blood to form hydrogen peroxide. Hydrogen peroxide is an electrochemically active species, which can be oxidized or reduced at certain potentials at the electrode. For example, this can be done amperometrically, in which a potential is applied and current is monitored, or voltammetrically, in which the potential is changed and current change is monitored. For example, as the hydrogen peroxide changes at the electrode in which a potential is applied, the corresponding current change is monitored as an electrical signal that can be further processed using signal processing techniques.

In one embodiment, a minimally-invasive multi-component microneedle device for detecting an analyte and delivering a therapeutic compound can include a microneedle array in conjunction with electrodes, e.g., which can be chemically-functionalized, enzyme-functionalized, and/or ion-selective electrodes, to perform multiplexed sensing and actuating applications in an autonomous, minimally-invasive, and controlled manner.

Figure 1B:
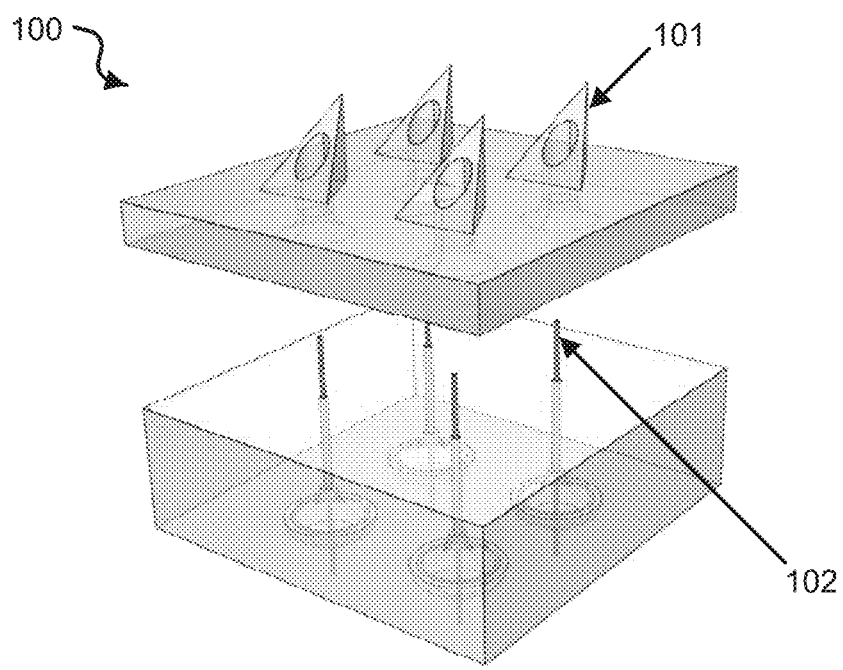

FIGS. 1A and 1B show schematics of an exemplary device based on hollowed needles with probes. FIG. 1A shows a schematic of an exemplary microneedle array device 100, and FIG. 1B shows an exemplary schematic of the device unassembled. The microneedle array 100 includes an array of hollowed microscale-sized needles 101, in which each needle 101 comprises a protruded needle structure having an exterior wall forming a hollow interior and an opening at the terminal end of the protruded needle structure to expose the hollow interior, and a probe 102 formed inside the exterior wall to interact with one or more chemical or biological substances that come in contact with the probe 102 via the opening to produce a probe signal (e.g., such as a sensing signal).

Figure 1C:
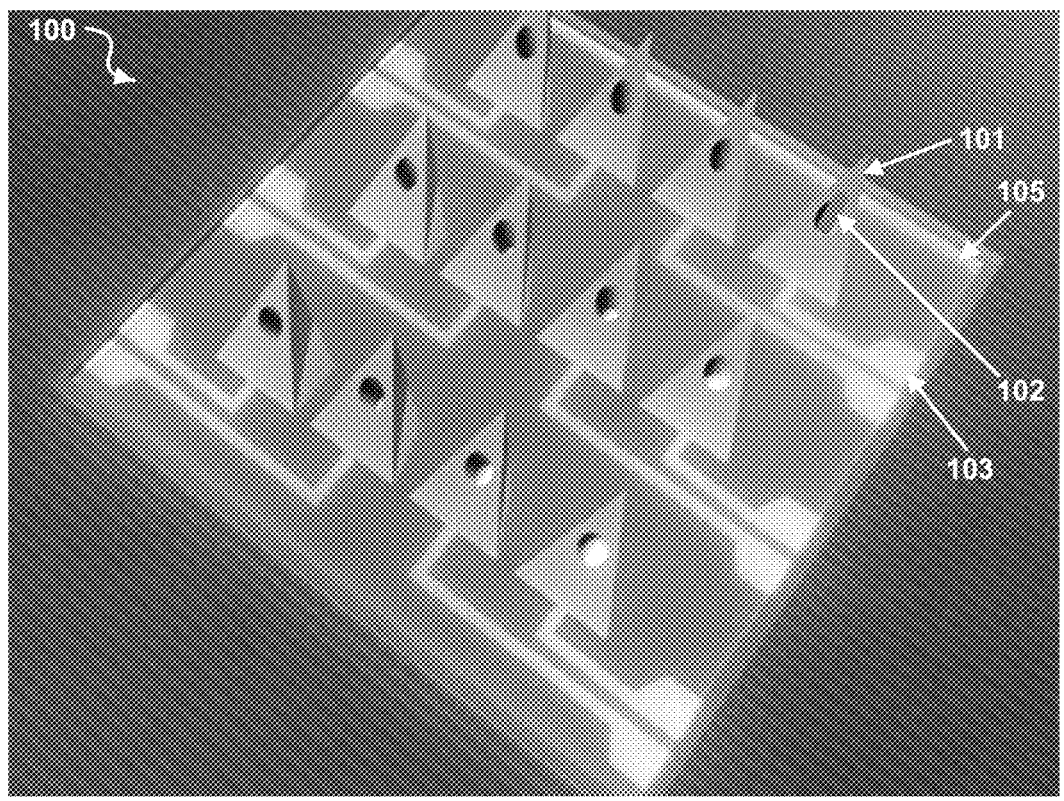

FIG. 1C shows the exemplary microneedle array 100 including an array of wires 103 that are coupled to corresponding probes 102 of the array of hollowed needles 101, respectively, e.g., which can provide an array of individually addressable microneedle sensing electrodes. The array of wires 103 can be configured within a substrate 105, e.g., such as an insulative material, which in some examples can be flexible and adhesive to biological tissue. Each wire of the array of wires 103 is electrically conductive to transmit the probe sensing signal produced by a respective probe to a sensor circuit, in which the probe sensing signals are processed.

Figure 1D:
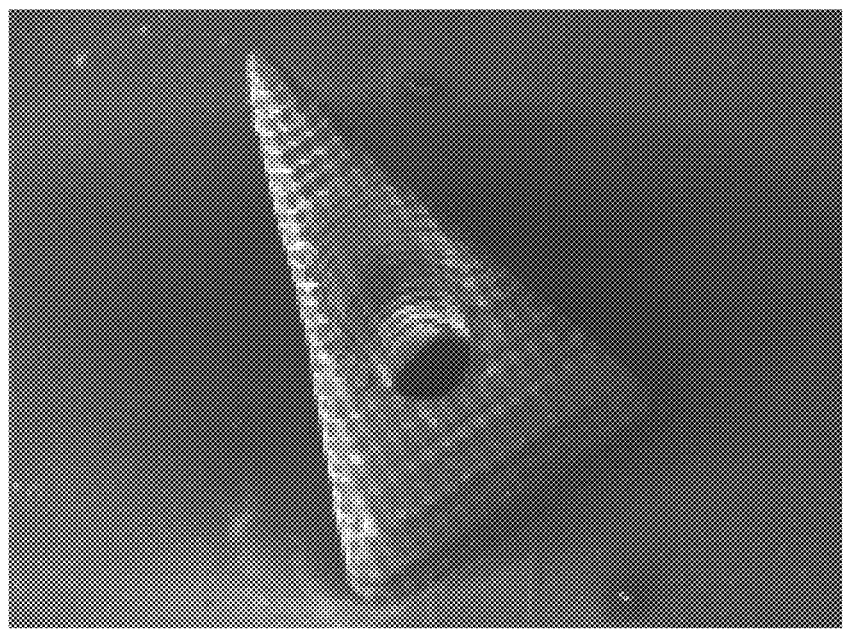

FIG. 1D shows an image of an exemplary microneedle imaged by scanning electron microscopy. FIG. 1E shows an image of an exemplary microneedle array near objects, such as a penny or an electronic circuit on a printed circuit board, to provide size scaling of the exemplary microneedle array. FIG. 1F shows a zoomed view of the image of the exemplary microneedle array.

The exemplary microneedle array based sensor actuator device can involve techniques in microfabrication, electrochemistry, enzyme-immobilized electrodes, and ion-selective electrodes. Potentiometric, voltammetric, amperometric, conductometric, and/or impedimetric detection methodologies can be integrated into one all-inclusive platform, e.g., in order to enable the direct biosensing of multiple analytes residing in bodily fluids (e.g., such as key biomarkers occupying the transdermal fluid). For example, the microneedle array platform can be integrated on an adhesive patch that is placed on the skin in order to monitor key physiological and biochemical parameters transdermally. The exemplary adhesive patch can further be integrated with electronics to allow communication and signal transduction. For example, because the chemical information can be converted to the electrical domain via electrochemistry, the device can be interfaced with electronic readout, e.g., which can be analogous to continuous-monitoring blood glucose devices. In this fashion, for example, the disclosed technology can miniaturize and integrate multiple laboratory-based tests into a single arrayed microneedle sensing platform and provide the ability to deliver an autonomous therapeutic intervention in a controlled and minimally-invasive fashion, as well as to tailor a cocktail of drugs for different forms of injury/trauma.

FIGS. 1G-1I show images of an exemplary microneedle array device on an adhesive patch implemented on living beings. FIG. 1G shows an image of an exemplary adhesive patch employing the microneedle array sensor-actuator device being worn on a human arm. FIG. 1H shows an image of another exemplary adhesive patch employing the microneedle array sensor-actuator device being worn on an animal. FIG. 1I shows an enlarged image of the exemplary device after the adhesive patch has been removed from the animal's skin, e.g., showing the exemplary microneedles intact.

Figure 1J:
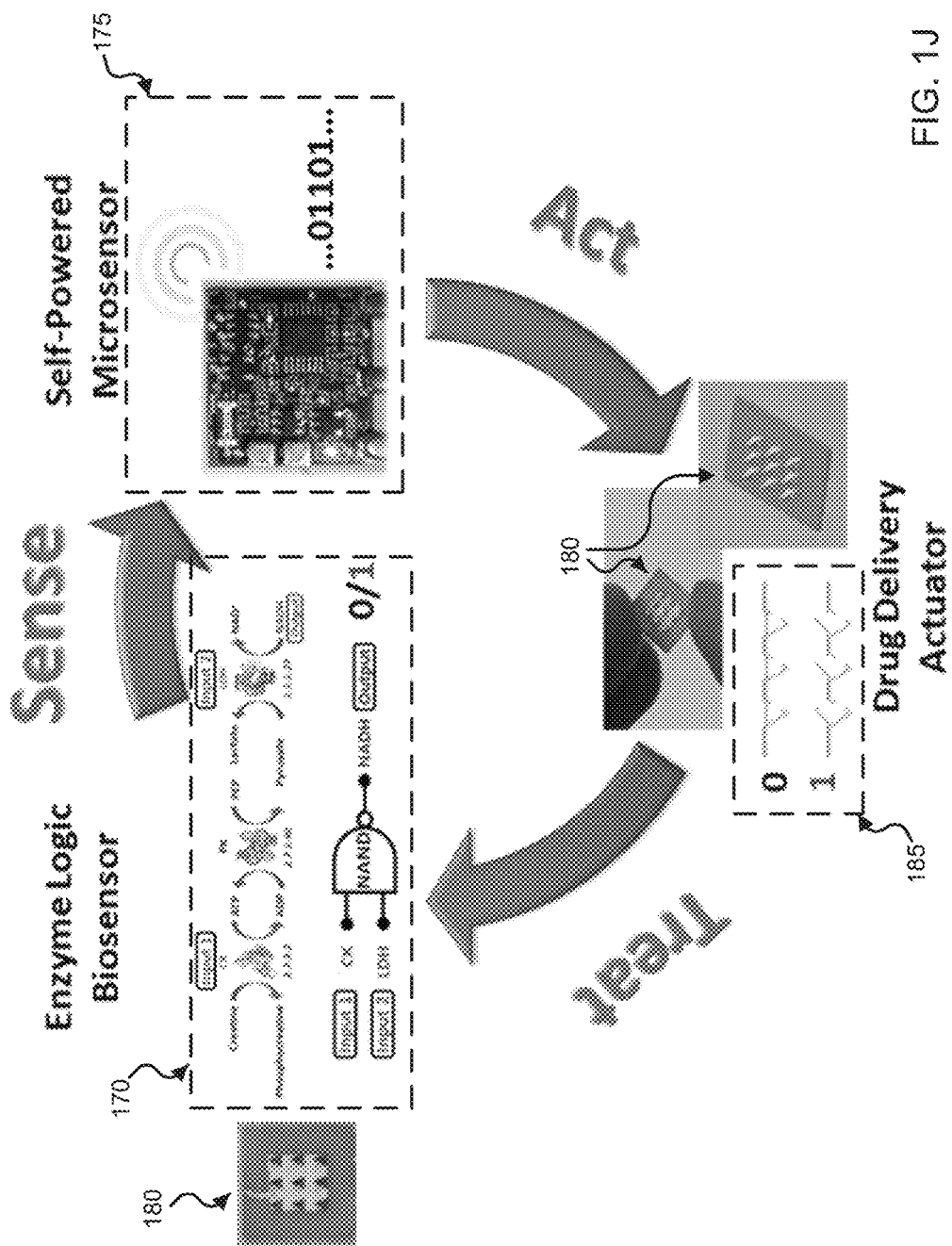
FIG. 1J shows an exemplary diagram of a 'Sense-Act-Treat' feedback loop.

The disclosed biosensor-actuator technology can be used to extract relevant physiological information and provide a controlled therapeutic response based on the detected physiological and biochemical information. FIG. 1J shows an exemplary diagram of a "Sense-Act-Treat" feedback loop where the sensed information is used to control the actuator to adjust the drug delivery. The information from the sensing operation enables the drug delivery to be tailored according to the sensed information. A biosensor-actuator device 180 in FIG. 1J can include a multiplexed array of microneedles (e.g., which can be configured in a manner as the exemplary microneedle array 100), in which some microneedles of the array are configured for sensing and other microneedles of the array are configured for therapeutic intervention.

The "Sense-Act-Treat" feedback loop, as shown in FIG. 1J, includes the sensing contingent of the biosensor-actuator device 180 to extract the physiological information of an analyte from a biological fluid (e.g., such as transdermal fluid). The exemplary sensing feature can include individually addressable microneedles functionalized as an electrochemical transducer that can detect patterns of biomarker changes, e.g., such as acute conditions or chronic disease conditions. A unique analyte can be detected at each microneedle within the sensing array, or multiple analytes can be detected by several electrodes housed in one microneedle. For example, various catalysts, biocatalysts, substrates, reagents, cofactors, and/or coreagents can be immobilized within the transducers to impart selectivity towards the analyte of interest. Likewise, ion-selective membranes (or solid state ion selective components) can be employed with electrochemical measurements to impart selectivity towards the ions of interest. In some examples, the sensing contingent of the biosensor-actuator device 180 can also include analyte logic-gate sensing for direct processing of the sensed analyte information, as shown in an exemplary diagram 170. For example, the diagram 170 shows two exemplary inputs (e.g., Input 1 and Input 2) of the analyte sensing logic, in which the Input 1 is a detected signal generated at a microneedle probe configured to detect a first reaction, and the Input 2 is a detected signal generated at another microneedle probe configured to detect a second reaction. The diagram 170 shows the two exemplary input signals passed through a logic gate (e.g., a single NAND gate in this example), in which the output of the logic gate can be used as a signal to control a microneedle actuator (e.g., in which the logic gate output signal is interfaced with an exemplary conducting polymer to control the porosity of a drug stored in a reservoir). In other examples, the sensed analyte information can be processed by a processing unit.

For example, the input biomarkers for a soft tissue injury (STI) can include creatine kinase (CK) and lactate dehydrogenase (LDH), which are incident on a biocatalytic cascade, and can be representative of the Input 1 and Input 2, respectively, as shown in the diagram 170. For example, CK converts the creatine substrate into phosphocreatine, which simultaneously causes the compound to convert ATP to ADP. In the presence of phosphoenolpyruvate (PEP), pyruvate kinase (PK) can give rise to pyruvate. If lactate dehydrogenase is present, the pyruvate can be converted to lactate while NADH is simultaneously oxidized to NAD+. Thus, the decrease in NADH can be monitored with respect to time in an amperometric fashion. For example, since only the presence of both CK and LDH causes a concomitant decrease in NADH, monitoring Input 1 and Input 2 using the exemplary biosensor-actuator device 180 can effectively function as a NAND Boolean logic gate.

The "Sense-Act-Treat" feedback loop, as shown in FIG. 1J, includes an exemplary image of a processing unit 175 to process the sensed analyte information as data and employ logic and/or instructions to control the actuator contingent of the biosensor-actuator device 180 to release, not release, or adjust the release of a therapeutic agent. For example, the processing unit 175 can include a processor and a memory coupled to the processor. The processing unit 175 can include a power supply, e.g., including battery sources, renewable energy sources (e.g., solar power sources), or self-powering sources (e.g., motion feedback power sources). The processing unit 175 can include an input/output (I/O) unit, coupled to the processor and memory, which can also be connected to an external interface, source of data storage, or display device. Various types of wired or wireless interfaces compatible with typical data communication standards, e.g., including, but not limited to Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement the I/O unit. For examples, the I/O unit of the processing unit 175 can be in communication with the biosensor-actuator device 180 using a wired configuration. In other examples, the I/O unit of the processing unit 175 can include wireless communication functionalities to receive data from the sensing contingent and transmit control data to the actuator contingent of the biosensor-actuator device 180. In such examples, the biosensor-actuator device 180 can include a wireless transmitter/receiver on or remotely tethered (e.g., using wires) to the substrate facilitating the sensor-actuator microneedle arrays. In such examples, the wireless transmitter/receiver can be interfaced with multiplexing capabilities to multiplex the sensing signals and control signals that are transmitted and received.

The "Sense-Act-Treat" feedback loop, as shown in FIG. 1J, includes the actuator contingent of the biosensor-actuator device 180 to deliver one or more drugs to the region penetrated by the microneedles based on the processed analyte information (sensed by the sensing contingent). The exemplary drug delivery feature can enable the autonomous delivery of a targeted therapeutic intervention in response to the detected acute or chronic condition. For example, the permeability of the conducting polymer nanoactuators can be tunable through an autonomous porosity change controlled by the integrated sensing or enzyme logic system (e.g., processed by the processing unit 175), which in turn can control release of the drug, as illustrated in a diagram 185 of the drug delivery actuator in FIG. 1J. The diagram 185 shows that a processed signal represented by 0 does not actuate the release of the drug (e.g., the porosity of the exemplary conducting polymer remains in an effectively closed stat). The diagram 185 also shows that a processed signal represented by 1 does actuate the release of the drug (e.g., the porosity of the exemplary conducting polymer is triggered to be in an open state, thereby allowing the drug to pass through the pores of the polymer and exit the microneedles into the tissue fluid). The arrayed microneedle structure can allow multivariate/multiplexed drug delivery, and a unique therapy can be delivered at each microneedle constituent of the array, as shown in FIGS. 1K and 1L.

Figure 1K:
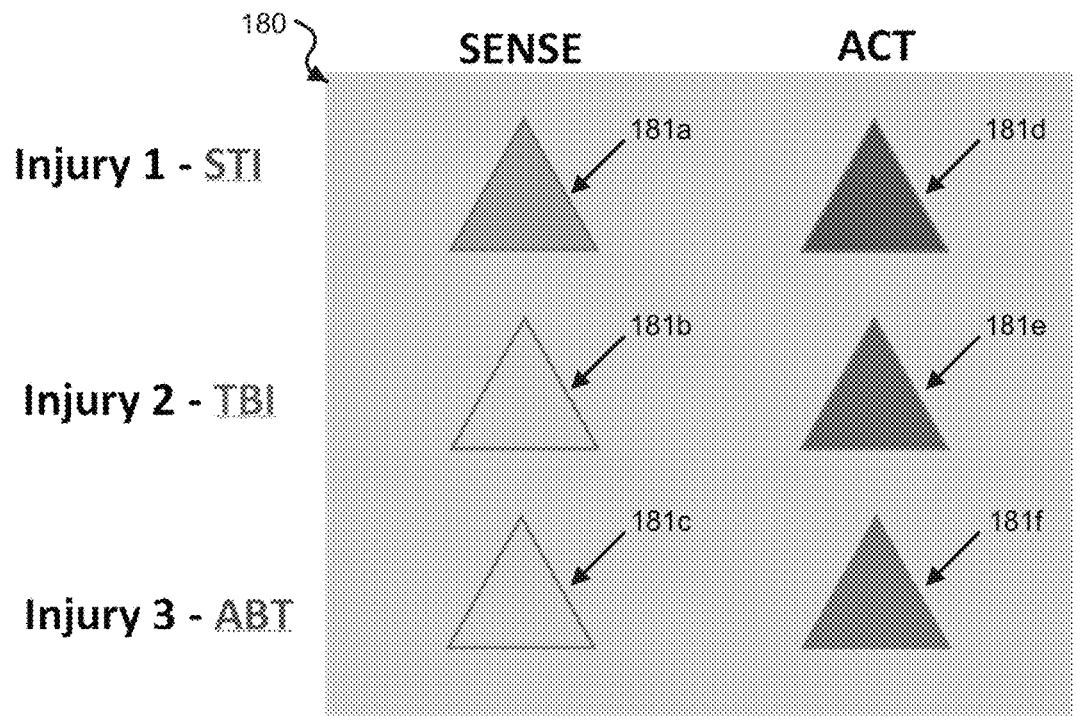
FIG. 1K shows a diagram of an exemplary microneedle array sensor-actuator featuring individually-addressable microneedles to monitor for different dysfunctions and individually-addressable microneedles to deliver a therapeutic agent in response to detection of the dysfunctions.

FIG. 1K shows a diagram of the exemplary microneedle array sensor-actuator 180 featuring individually-addressable microneedles to monitor for different dysfunctions and individually-addressable microneedles to deliver a therapeutic agent in response to detection of the dysfunctions. The diagram of the biosensor-actuator device 180, as shown in FIG. 1K, includes microneedles of the array that are configured for sensing (e.g., microneedles 181$a$, 181$b$, and 181$c$) and other microneedles of the array that are configured for therapeutic intervention (e.g., microneedles 181$d$, 181$e$, and 181$f$). In this example, the microneedle 181$a$ is configured for sensing an analyte associated with soft tissue injury (STI), the microneedle 181$b$ is configured for sensing an analyte associated with traumatic brain injury (TBI), and the microneedle 181$c$ is configured for sensing an analyte associated with abdominal trauma (ABT). Also in this example, the microneedle 181$d$ is configured for delivering a drug associated with treating STI, the microneedle 181$e$ is configured for delivering a drug associated with treating TBI, and the microneedle 181$f$ is configured for delivering a drug associated with treating ABT.

For example, exemplary analytes associated with STI that can be detected (e.g., using the sensor-actuator 180) include creatine kinase, lactate, and lactate dehydrogenase; e.g., ameliorated with glucocorticoids, NSAIDs. Exemplary analytes associated with TBI that can be detected include glutamate, ceruloplasmin; e.g., ameliorated with acetaminophen. Exemplary analytes associated with ABT that can be detected include lactate, lactate dehydrogenase; e.g., ameliorated with acetylsalicylic acid or iso-butyl-propanoic-phenolic acid.

Figure 1L:
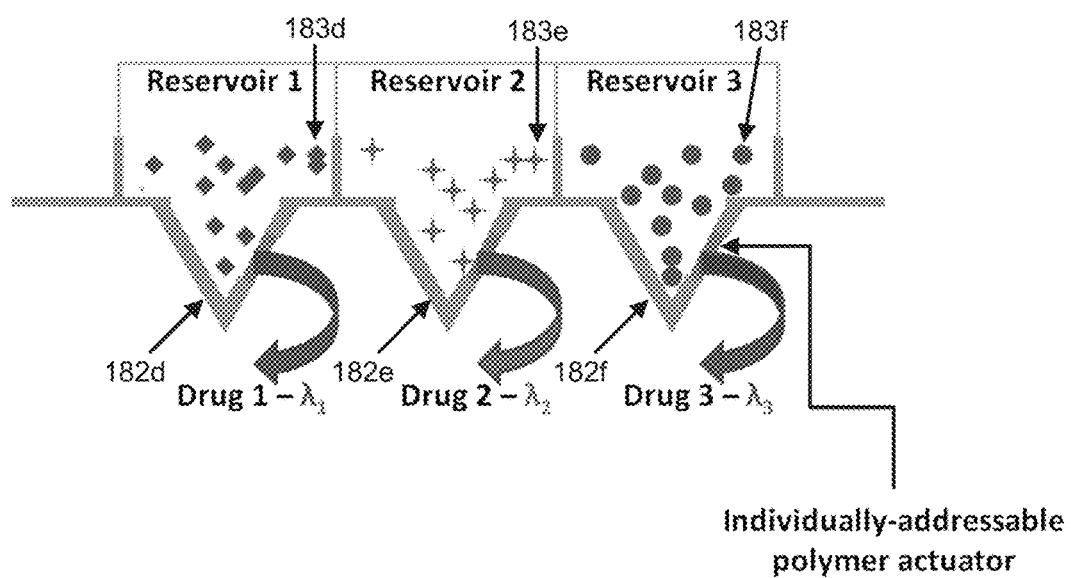
FIG. 1L shows an illustration of an exemplary multiplexed controlled release of targeted therapeutic agents.

FIG. 1L shows an illustrative diagram of a multiplexed controlled release of a targeted therapeutic cocktail, e.g., where the polymer actuator(s) is individually addressable for on-demand release for targeted therapeutic intervention. The diagram of FIG. 1L shows exemplary microneedles of the actuator contingent (e.g., microneedles 182$d$, 182$e$, and 182$f$) that are configured for therapeutic intervention. In this example, the microneedle 182$d$ is configured for controlled release of a drug 183$d$ that is stored in Reservoir 1, the microneedle 182$e$ is configured for controlled release of a drug 183$e$ that is stored in Reservoir 2, and the microneedle 182$f$ is configured for controlled release of a drug 183$f$ that is stored in Reservoir 3. For example, based on a control signal received from the processing unit (e.g., like that shown in the diagram 185 in FIG. 1L), the release of any or all of drugs 183$d$, 183$e$, and/or 183$f$ can be controlled (e.g., using multiplexing) to produce a targeted therapeutic cocktail, e.g., in which the individually-addressable polymer actuator(s) are actuated in a manner that can control the size of the porosity (e.g., and thereby the flow), as well as the duration of the open state, controlling concentration of each of the released drugs.

Figure 2A:
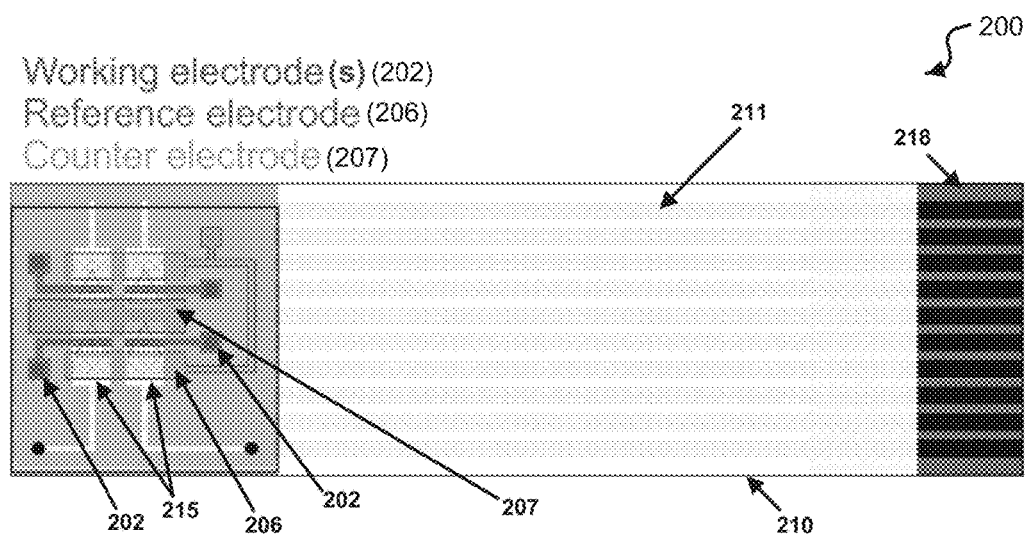
FIGS. 2A-2C show schematics of an exemplary microneedle array strip system.
Figure 2B:
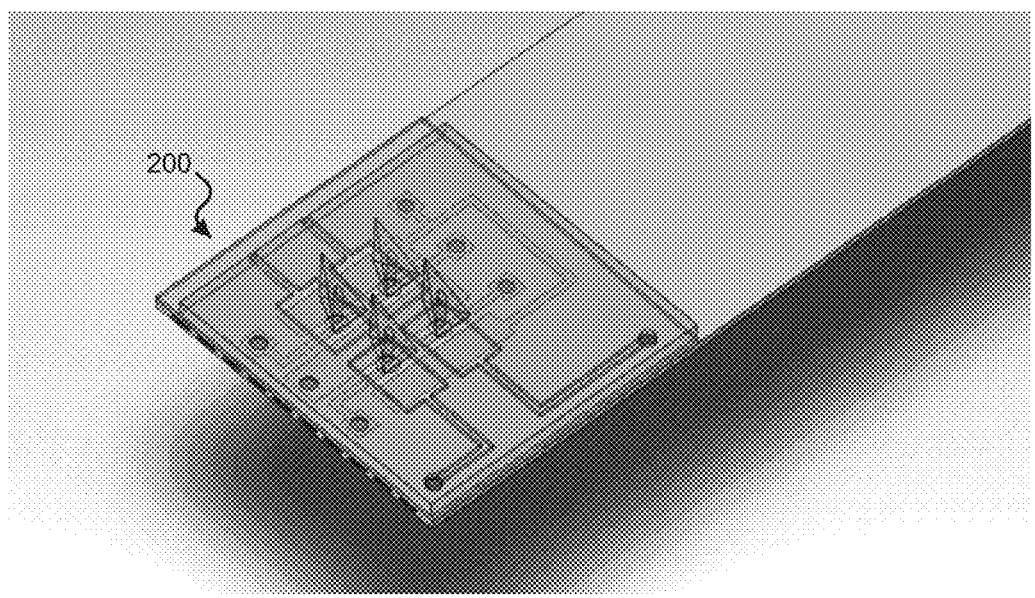
Figure 2C:
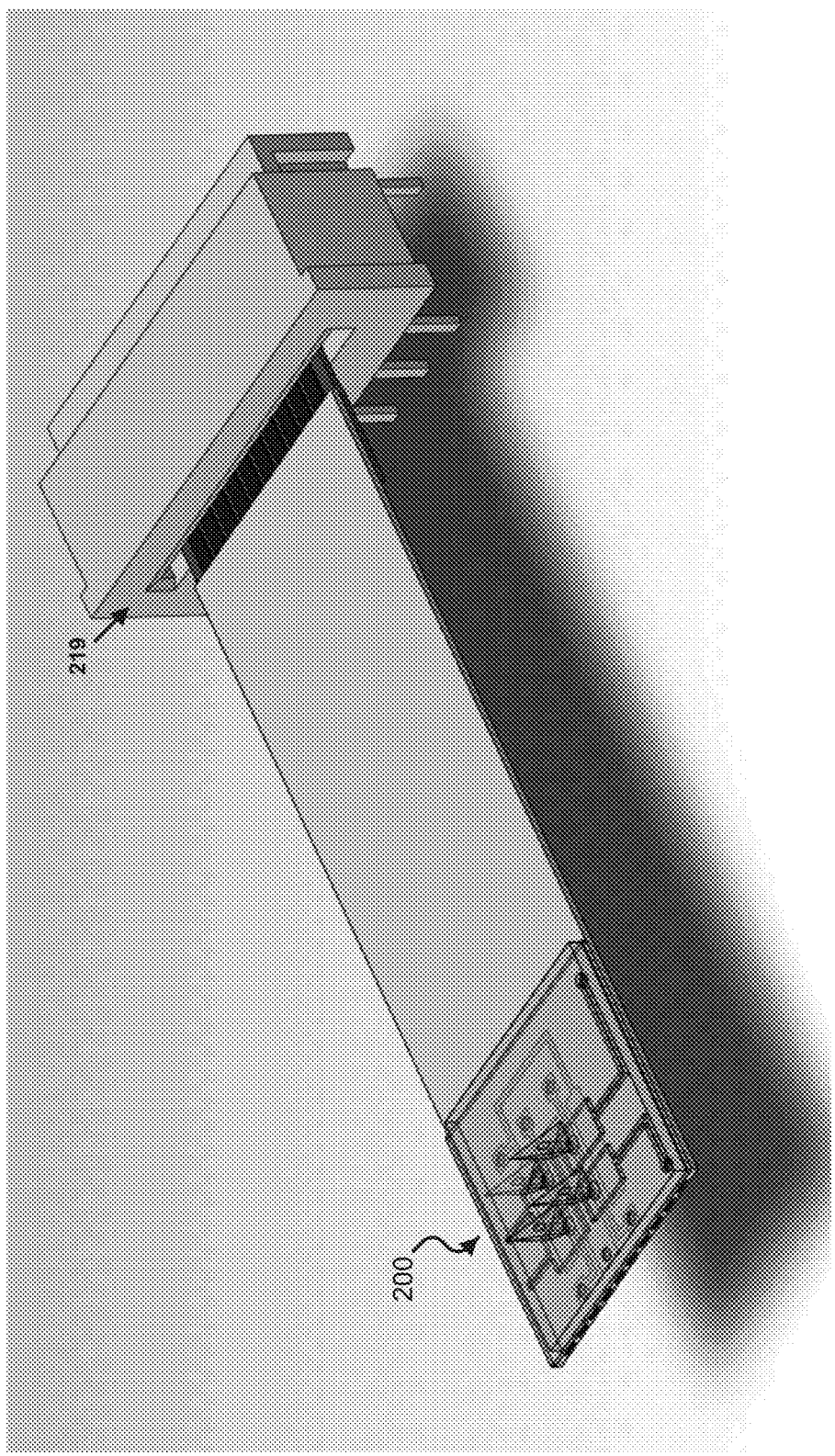

FIGS. 2A-2C show schematics of an exemplary microneedle array strip system 200. In this example, the system can include a flat flex cable (FFC) 210 that includes a plurality of conductors 211 (e.g., ten copper conductors) that interconnect the microneedle array to a connector region 218, e.g., in which the conductors 211 can be 1.5" length and interface (e.g., right end (re)connected) to a circuit board, e.g., via a zero insertion force (ZIF) connector. For example, the exemplary microneedle array strip system can be configured on a FFC sized to be 11.0 mm by 38.1 mm. Holes can be opened using laser ablation at the left end to expose underlying traces. Metal electrodes, e.g., four working electrodes 202 and one counter electrode 207 and one or more reference electrode(s) 206, can be sputter deposited on the surface over the openings. Four vented fluidic chambers 215 can be made from laser ablated Mylar with a pressure sensitive adhesive. The adhesive layer can also bond microneedle array(s) to the FFC. FIG. 2A shows a top view of the schematic of the microneedle array strip system 200. FIG. 2B shows a three dimensional view of the schematic of the microneedle array strip system 200. FIG. 2C shows another three dimensional view of the schematic of the microneedle array strip system 200 inserted into a circuit board connector 219.

In another example, individually addressable electrodes (microneedles) can be loaded with a carbon paste, carbon fiber, or conducting polymer transducer and be employed for the detection of patterns of biomarker changes that reflect optimal health and/or performance. Using potentiometry, amperometry, or voltammetry, various catalysts, biocatalysts, substrates, reagents, cofactors, and/or coreagents can be immobilized within the transducers to impart selectivity towards the analyte of interest. Likewise, ion-selective membranes (or solid state ion selective components) can be employed with electrochemical measurements to impart selectivity towards the ions of interest. Significant predictive and diagnostic information can be available in monitoring multiple biomarkers and in measuring the dynamical pattern of those species as a measure of the overall health/performance/fitness of the subject. Patterns in multiple biomarkers can be integrated and changes in those markers can be assessed over extended time periods in order to provide a more detailed and accurate temporal characterization of the negative effects of stress and overtraining in addition to a plethora of diseases and illnesses.

For example, arraying the microneedles can allow for measuring patterns in multiple bioanalytes. Moreover, an analyte or multiple analytes, such as a catalyst/biocatalyst or other analyte or biomarker substance, can be immobilized by robust means that can include electropolymerization/polymer entrapment, electrostatic interactions, covalent attachment, and direct adsorption. In one example, a planar solid-state transducer can be an electrode, for example, use of carbon fiber, carbon paste, and conducting polymers to form the electrochemical transducer.

The exemplary device can be utilized in the following manner. A transdermal microneedle array can be employed; each microneedle constituent can contain a bored cylindrical vacancy inside which a three-electrode electrochemical sensing element is housed (e.g., such as potentiometric, voltammetric, amperometric, conductometric, impedometric, etc. sensing elements). In one example, an enzyme (with affinity to a particular biochemical moiety) can be immobilized on the working electrode of the three-electrode contingent and amperometry can be performed. In another example, an ion-selective membrane (with suitable ionophore) or solid state functionalization can be applied to the working electrode and potentiometry or voltammetry is performed. The presence of the analyte, metabolite, electrolyte, or ion of interest can result in perturbations in the detected current (enzyme electrode) or potential (ion-selective electrode), respectively.

Figures 3A, 3B, 3C:
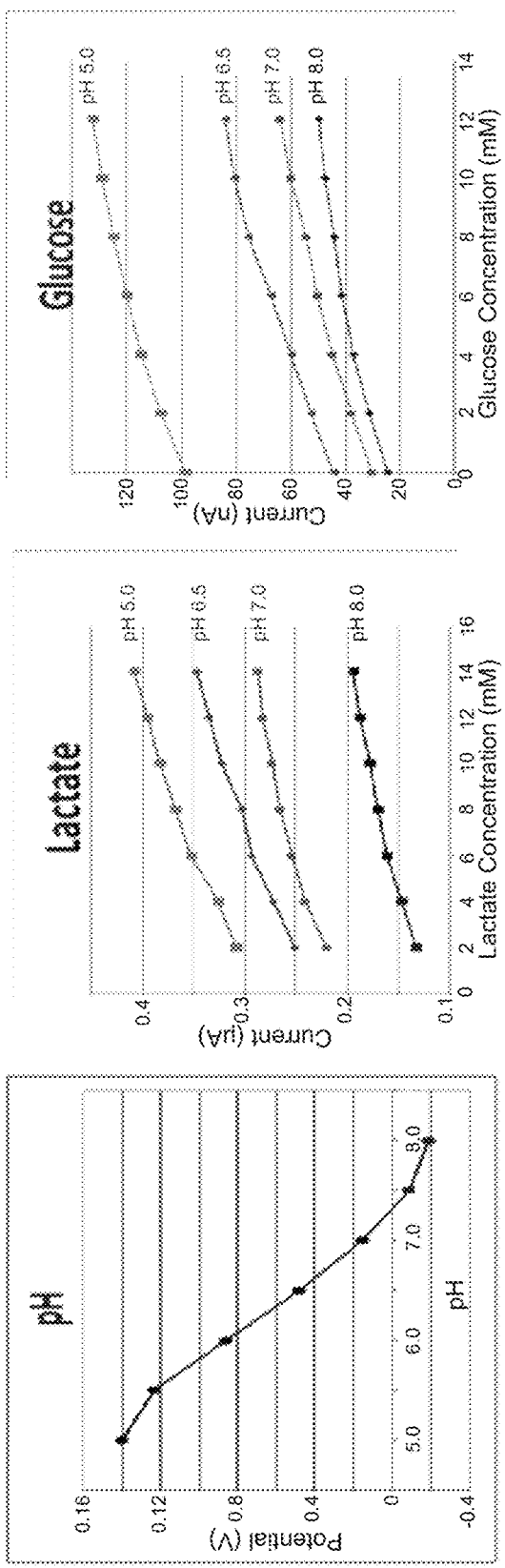
FIGS. 3A-3C show data plots of exemplary results of multiplexed detection of various biomarkers on an electrochemical array strip using individual microneedles.

FIGS. 3A-3C show data plots of exemplary results of multiplexed detection of various biomarkers on an electrochemical array strip using individual microneedles. FIG. 3A shows a data plot of multiplexed detection of pH; FIG. 3B shows a data plot of multiplexed detection of lactate; and FIG. 3C shows a data plot of multiplexed detection of glucose.

FIGS. 4A and 4B show exemplary individual microneedle microsensors that can be addressable through a microelectrode array mated with the reverse side of the device. For example, the array(s) can be fabricated using a number of techniques including photolithography, inkjet printing, and screen printing, among other techniques. An example of a screen printed microneedle array is shown in FIG. 4A, and a microneedle array fabricated by a stenciling process used to define the pattern is shown in FIG. 4B.

In another embodiment of the disclosed technology, a minimally-invasive multi-component microneedle device for electrochemical monitoring and biosensing is described. This embodiment can comprise the same embodiment(s) like those previously described, and can therefore implement the entirety of functionalities of the individual embodiments on a single embodiment. For example, the disclosed technology can be implemented for the electrochemical monitoring and biosensing of the excitatory neurotransmitter glutamate and glucose. In this exemplary embodiment, a device can include tight integration of solid and hollow microneedles into a single biosensor array device containing multiple microcavities. Such microcavities can facilitate the electropolymeric entrapment of the recognition enzyme within each microrecess. The resulting microneedle biosensor array can be employed as an on-body minimally-invasive transdermal patch, e.g., eliminating extraction/sampling of the biological fluid, thereby simplifying device requirements.

Exemplary implementations were performed to demonstrate various functionalities of the device, e.g., including the electropolymeric entrapment of glutamate oxidase and glucose oxidase within a poly(o-phenylenediamine) (PPD) thin film. For example, the PPD-based enzyme entrapment methodology can enable the effective rejection of coexisting electroactive interferents without compromising the sensitivity or response time of the device. The resulting microneedle-based glutamate and glucose biosensor can exhibit high selectivity, sensitivity, speed, and stability in both buffer and untreated human serum. For example, high-fidelity glutamate measurements (e.g., down to the 10 µM level) were obtained in undiluted human serum. The exemplary recess design can also protect the enzyme layer upon insertion into the skin. The described robust microneedle design can be well-suited for diverse biosensing applications in which real-time metabolite monitoring is a core requirement.

The exemplary microneedle-based glutamate and glucose biosensor were implemented in ways that demonstrate clinical application of microdevices for the on-body monitoring of relevant bioanalytes by minimally-invasive electrochemical biosensors. In this regard, the microneedle arrays can be configured to provide pain-free biosensing and, being highly integrated biocompatible devices, these devices can be fabricated on an industrial scale and at low cost. For example, the described microneedle arrays can perform monitoring and biosensing applications without involving fluid sampling/extraction. For example, a feature of the technology is that the uptake of bodily fluids (e.g., such as transdermal fluid) is not required, as is in conventional microfluidic sensing systems. Through the execution of electrochemistry at the microneedle-transdermal fluid interface, useful chemical information can be extracted and directly transduced to the electronic domain. In this manner, sophisticated and costly mechanical devices that regulate flow to a detector array/separate sensing unit can be eliminated from implementation.

The exemplary microneedle sensing array device can employ a recess-based microcavity structure that can be designed to confine the recognition enzyme and protect it upon penetration of the skin. For example, a bicomponent microneedle biosensor can include an array of platinum-coated solid microneedles, which can serve as the working electrode, and a hollow microneedle cover, which can provide a microcavity that surrounds each solid microneedle. This exemplary bicomponent microneedle biosensor is shown in FIGS. 5A-5D. FIGS. 5A-5D also illustrate a process to fabricate the exemplary bicomponent microneedle biosensor.

FIG. 5A shows a solid microneedle constituent 501 and a hollow microneedle constituent 503 of an exemplary array of bicomponent microneedle electrodes 500. The solid microneedle constituent can be coated with a conductive material to form a working electrode, e.g., such as a platinum working electrode 502. FIG. 5A also shows a process to assemble the platinum-coated solid microneedles 502 with the hollow microneedle cover 503. In some examples, the assembly includes applying a sealing agent (e.g., epoxy) to the non-detecting, non-recessed regions between the solid microneedle constituent 501 and the hollow microneedle constituent 503. FIG. 5B shows the bicomponent microneedle array electrode 500 fully-assembled. As shown in FIG. 5B, each bicomponent microneedle electrode 500 in the array includes a recess region that exposes the needles (e.g., the platinum-coated electrodes 502) of the solid microneedle constituent 501, e.g., such that the recess can facilitate enzyme immobilization. FIG. 5C shows the growth of the glutamate oxidase (GluOx)-functionalized PPD film 504 at the solid microneedle surface within the recess region of the microneedle electrode 500 from the o-phenylenediamine (o-PD) monomer of a o-PD-GluOx solution. For example, fabrication of the array of bicomponent microneedle electrodes 500 can include applying a GluOx-PPD thin film to the platinum working electrodes 502 by immersing the microneedles in an o-PD-GluOx solution. FIG. 5D shows the biocatalytic behavior of the electropolymerized glutamate oxidase-poly(o-phenylenediamine) film 504 (illustrated in purple), e.g., enabling the quantification of glutamate levels within the transdermal fluid. In these exemplary figures, glucose oxidase (GOx) becomes substituted in place of GluOx for the quantification of glucose.

The recess-based microneedle electrodes 500 can enable electropolymeric entrapment of the enzyme within the individual microcavities. As a result, direct transdermal biosensing can be accomplished without requiring the uptake of the transdermal fluid, e.g., thereby simplifying device requirements and the sensing process. The bicomponent recess geometry of the microneedle biosensor can also provide a greater surface area for enzyme immobilization with microneedles containing embedded planar electrodes.

The recess-based microneedle electrodes 500 can include electropolymerized PPD thin films that can be employed for the confinement of enzymes into miniaturized electrode transducers, e.g., while imparting remarkable permselective properties and a stable response. In one example, PPD can be used for entrapping different oxidase enzymes such as glucose oxidase, lactate oxidase, and glutamate oxidase, along with permselective detection of the liberated hydrogen peroxide product. As a consequence of their remarkable permselective properties, PPD films can impart high selectivity and stability through exclusion of co-existing electroactive interferences and proteins normally present within bodily fluids. The described biosensor devices, which can employ PPD films, can thus facilitate the amperometric detection of hydrogen peroxide with high substrate selectivity, excellent sensitivity, operational stability, and rapid response time. In this manner, the described biosensor devices that employ enzyme-functionalized PPD films can exhibit considerable sensing advantages when compared with those based on other immobilization techniques, as described herein.

For example, to illustrate the versatility of the disclosed bicomponent microneedle array platform, an exemplary biosensor device for amperometric glutamate biosensing is demonstrated. This exemplary platform can be subsequently extended to glucose monitoring for the management of diabetes mellitus. For example, an excitatory neurotransmitter, glutamate, can be implicated in a number of pathologic medical conditions such as ischemic neuronal injury, hypoglycemic injury, epilepsy, Alzheimer's disease, and traumatic brain injury. In addition, elevated glutamate levels in the circulatory system can be associated with excitotoxicity. Blood glutamate levels have risen from an average value of 37.5 µM among healthy patients to 141.3 µM among patients who have sustained moderate to severe trauma related to intracranial injury. As such, serum glutamate levels can provide useful insight into the overall condition of the central nervous system following brain trauma.

For example, the described biosensing platform can be advantageous over biosensors that quantify glutamate levels with a high degree of invasiveness, e.g., such as by uptaking the cerebrospinal fluid (CSF) via a catheter or a microdialysis probe for further analysis. Also for example, the described biosensing platform can be advantageous over biosensors that typically are clinically implemented in a hospital setting, e.g., as such clinical analysis can be a painful, time-consuming, and costly proposition. In addition, the described biosensing platform can be amenable to on-body continuous monitoring, especially when access to the CSF is not feasible. As blood glutamate levels correlate well with the levels found in the CSF, its extraction from this hard-to-access bodily fluid is unnecessary under the disclosed embodiment.

An exemplary demonstration of the described biosensor device involves the enzymes glutamate oxidase (GluOx) and glucose oxidase (GOx) that can be entrapped within the microcavities of the exemplary microneedle device using different PPD growth processes, each with its own specific advantage that can be tailored to specific applications. The PPD-based confinement of the enzymes within the microneedle cavities can enable the efficient quantification of glutamate and glucose at pathophysiological levels within buffer solutions and undiluted human serum. For example, the minimally-invasive nature of the exemplary device, combined with its convenient means to achieve enzyme entrapment and protection, as well as its attractive electroanalytical performance, can demonstrate its applicability as a practical patch-type on-body biosensor.

Exemplary materials and methods to implement the disclosed embodiment of the technology are presented. The following chemicals and reagents were used in the described implementations, which included glutamate oxidase (GluOx, E.C. 1.4.3.11) from *E. coli* (recombinant), glucose oxidase (GOx, E.C. 1.1.3.4) from *Aspergillus niger*, 1,2-phenylenediamine (o-Pd), L-glutamatic acid (GLU), D-(+)-glucose (GLC), L-ascorbic acid (AA), uric acid (UA), L-cysteine (CYS), acetaminophen (ACT), sodium sulfate, ethylenediaminetetraacetic acid (EDTA), potassium phosphate monobasic, potassium phosphate dibasic, and serum from human male (type AB). The exemplary implementations (with the exception of the serum calibration) were performed in 0.1 M phosphate buffer (pH 7.40) with 0.5 mM EDTA. Ultrapure water (18.2 M$\Omega$·cm) was employed in all exemplary implementations.

The instrumentation used in the described implementations included the following, which was utilized in exemplary demonstrations and implementations of the disclosed embodiment under exemplary conditions disclosed herein. A CH Instruments (Austin, Tex.) model 1232A electrochemical analyzer was employed for electrochemical measurements. An external Ag/AgCl reference electrode (CH Instruments CHI111) and a 0.5 mm diameter platinum wire counter electrode (BASi, West Lafayette, Ind.) were used to establish a three-electrode electrochemical system. Voltammetric and chronoamperometric studies were used to evaluate the electrochemical behavior of the microneedle array electrode at room temperature (22° C.). In these exemplary electrochemical implementations, glutamate (or glucose) was added into 2 mL of phosphate buffer solution or serum (stirred) in order to obtain the desired concentration. Chronoamperometric currents were sampled for 15 s following the application of the potential step. The morphology of the bicomponent microneedle array was examined using a field emission scanning electron microscope (SEM) (Philips XL30, Amsterdam, the Netherlands). Specimens were coated with chromium prior to SEM analysis using a sputtering instrument (Energy Beam Sciences Emitech K575X, E. Granby, Conn.). A deposition current of 130 mA was applied for 30 s to deposit ~15 nm of chromium on the sample surface.

The exemplary solid and hollow microneedle arrays used in the exemplary implementations were developed in the following manner. The microneedle designs were prepared using a CAD software, e.g., Solidworks (Dassualt Systemes S.A., Velizy, France). Substrate support structures were created with Magics RP 13 (Materialise NV, Leuven, Belgium). For example, the solid needles were designed and fabricated with a conical in shape and possess a base diameter of 390±14 μm and a height of 818±35 μm. The hollow needles were pyramidal in shape with a triangular base. The dimensions of each hollow microneedle were as follows: an edge length of 1174±13 μm, a height of 1366±15 μm, and a vertical cylindrical bore of 342±5 μm diameter on one of the faces of the pyramid structure. Both the solid and hollow needles were arranged into 3×3 square arrays with 2 mm periodicity. Substrates for the microneedle arrays were 10 mm×10 mm in extent and possessed thickness values of 2000 μm and 500 μm for solid and hollow variants, respectively. The three-dimensional computer models were transferred to a Perfactory® SXGA Standard UV rapid prototyping system (EnvisionTEC GmbH, Gladbeck, Germany) for fabrication. This system used computer models to precisely guide light from a 150 W halogen bulb over a photocurable material, e.g., resulting in the selective polymerization of the exposed material. In some aspects, Eshell 200 acrylate-based polymer (EnvisionTEC GmbH) can be utilized as the constituent material to fabricate the microneedle arrays since the resin selectively polymerizes under visible light and exhibits a Young's modulus of elasticity of 3050±90 MPa. Moreover, the polymer features Class-IIa biocompatibility per ISO 10993. A 550 mW output power beam (step size=50 μm) with a zero-degree tilt was employed for the polymerization of the resin. Following the fabrication routine, the arrays were rinsed with isopropanol to remove the unpolymerized material. The arrays were placed in an Otoflash post curing system (EnvisionTEC); and post-build curing was performed for 50 s. A Compex 201 krypton-fluoride (KrF) excimer laser (Coherent, Santa Clara, Calif.), which can be operated with a 10 Hz repetition rate and a wavelength of 248 nm, was used to ablate a commercially-obtained high purity Pt target. This process resulted in the deposition of thin films of Pt (~12 nm) on the surface of the solid microneedle array. A background pressure of 5 μTorr was maintained during the 2 min pulsed laser deposition (PLD) routine, performed at room temperature.

Adhesive non-conducting epoxy can be applied to the periphery of the solid microneedle substrate. The hollow microneedle cover can then be placed over the solid microneedle substrate. This exemplary procedure is diagrammatically represented in FIGS. 5A and 5B. For example, the two components (e.g., the solid microneedle substrate and the hollow microneedle cover) can be arranged under an optical microscope to align the solid microneedles within the hollow microneedle aperture. This can form the bicomponent microneedle array electrode (BMAE), as shown in FIG. 5C, e.g., which can be mated with a 3 mL syringe (BD Biosciences, Franklin Lakes, N.J.). For example, the nozzle portion of the syringe can be removed to facilitate the attachment of the BMAE, which can be affixed using adhesive epoxy to the syringe tip for easier handling. A copper wire can be subsequently inserted into the open end of the syringe in order to create an electrical contact to the Pt working electrode. A poly(o-phenylenediamine) (PPD) film can be electropolymerized from a solution of the o-phenylenediamine (o-Pd) monomer, as shown in FIG. 5C, e.g., to immobilize the GluOx and GOx enzymes on the electrode surface and reject potential electroactive interferents. For example, a 0.1 M phosphate buffer (pH 7.40) solution containing 10 mM o-Pd, 5 mM sodium sulfate, and 100 U/mL GOx can be purged with nitrogen for 20 minutes at room temperature, which can be used to form the GOx-functionalized electrode. For example, the BMAE, Ag/AgCl reference, and platinum counter electrodes can then be immersed in the solution; a potential of 0.75 V vs. Ag/AgCl can subsequently be applied for 20 min in order to grow the GOx-entrapped PPD film, as represented in FIG. 5C. This exemplary process represents a rapid means to immobilize enzymes and is appropriate for applications in which the enzyme is of sufficiently low cost such that the entire extent of the electrode can be immersed in the enzyme-o-PD solution.

In other examples, a slight variant of the aforementioned process can be used, e.g., to conserve the costly GluOx enzyme during the electropolymerization process. In this alternative exemplary process, the BMAE, Ag/AgCl reference, and platinum counter electrodes can be immersed in a solution of 0.1 M phosphate buffer (pH 7.40) containing 10 mM o-Pd and 5 mM sodium sulfate; and a potential of 0.75 V vs. Ag/AgCl can subsequently be applied for 5 min. The electrode can then be rinsed and dried at room temperature. A 0.5 μL aliquot solution of 7.5 U/mL GluOx in 0.1 M phosphate buffer (pH 7.40) can then be dispensed in each recess of the BMAE; this step can be repeated an additional six times on each microneedle using a low-retention micropipette. Following this process, the solution can be allowed to dry at room temperature. The drop-casting procedure can be repeated five additional times. Subsequently, a solution of 0.1 M phosphate buffer (pH 7.4) containing 10 mM o-Pd, 5 mM sodium sulfate, and 1 U/mL GluOx can be dispensed on each microcavity of the microneedle array. A potential of 0.75 V vs. Ag/AgCl can subsequently be applied for 15 min in order to electropolymerize the GluOx-entrapped-PPD film. For example, whereas the previous described process can be adapted for simplicity at the expense of increased enzyme usage, this implementation can facilitate the electropolymerization of more costly enzymes.

Following each electropolymerization process, the BMAE can be rinsed and immersed in a 0.1 M phosphate buffer solution (pH 7.4) for 30 min to remove monomeric residue from the microneedle structure as well as any non-bound enzyme. When not in use, the BMAE can be stored in phosphate buffer at 4° C. This exemplary process, which is diagrammatically represented in FIG. 5D, can enable the quantification of glutamate and glucose, as well as other analytes.

Figure 6A:
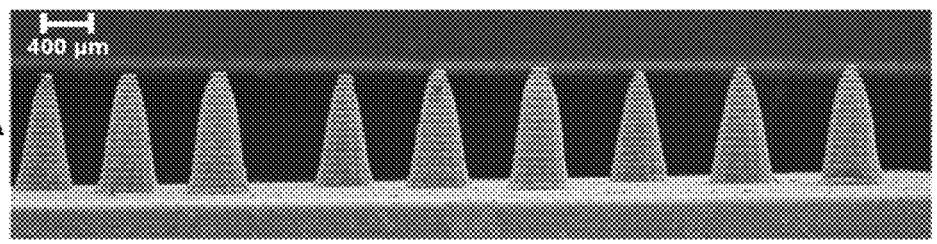
FIGS. 6A and 6B show scanning electron microscopy (SEM) images of exemplary solid and hollow microneedle arrays, respectively.
Figure 6B:
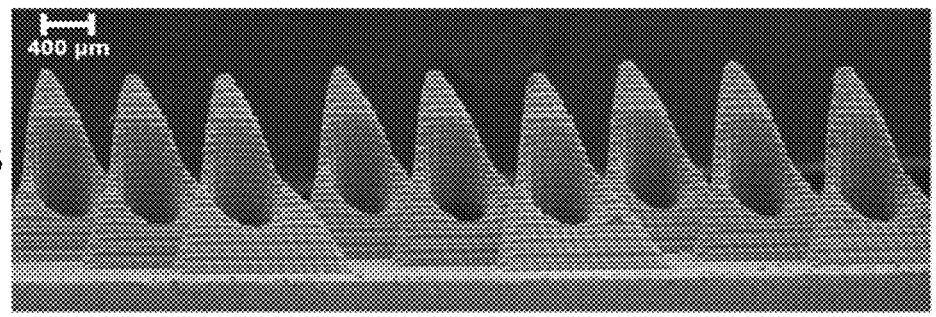

The exemplary implementations of the described microneedle array biosensor device included an evaluation of the surface morphology of the BMAE which was performed to ascertain the electrode geometry and surface features. A close examination of the BMAE surface morphology was executed using SEM. FIG. 6A shows exemplary scanning electron micrographs of the solid microneedle arrays. FIG. 6B shows exemplary scanning electron micrographs of the hollow microneedle arrays. As shown in the SEM images, the features of the exemplary microneedles closely corresponded with those specified in the exemplary computer-aided design file. For example, a uniform distribution of the solid and hollow microneedles can be observed at the microneedle array. With respect to the exemplary solid microneedle (FIG. 6A), a notable observation is the ribbed structure, which can be attributed to the layer-by-layer approach that was utilized to polymerize the E-shell 200 resin. A uniform pyramidal structure and a triangular base can be observed at each component of the hollow microneedle array (FIG. 6B), along with apertures of uniform size distribution. Minimal to no microneedle-to-microneedle geometric variation was observed.

Figure 7:
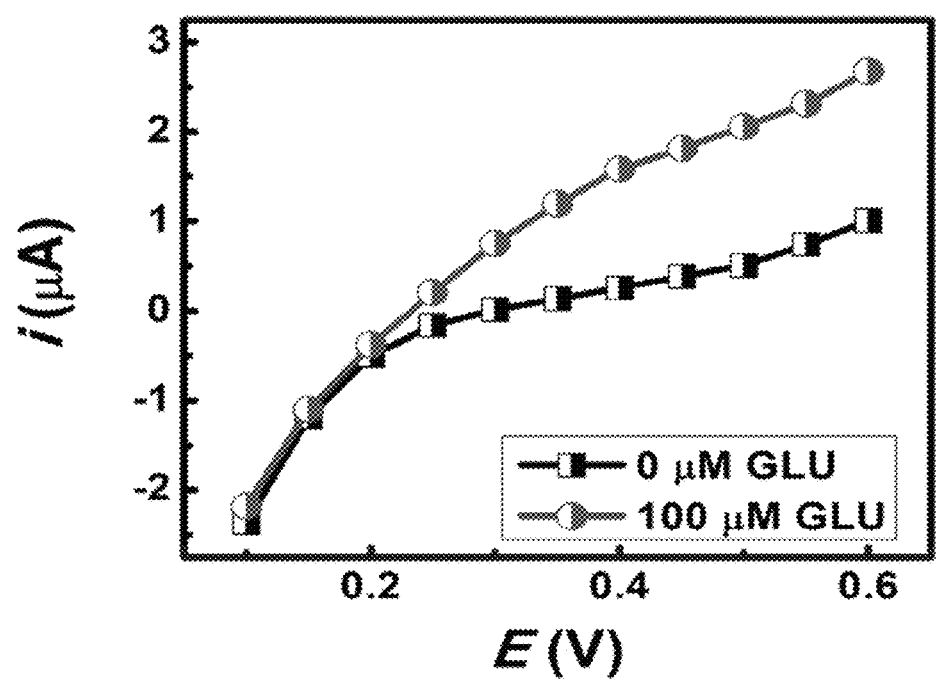
FIG. 7 shows a hydrodynamic voltammogram data plot of exemplary glutamate bicomponent microneedle array electrodes.

The exemplary implementations of the described microneedle array biosensor device included electrochemical characterizations of the bicomponent microneedle electrode towards the amperometric detection of glutamate. The initial electrochemical characterization of the BMAE was aimed at constructing hydrodynamic voltammograms (HDVs), e.g., to select an optimal detection potential. For example, an HDV can be obtained using chronoamperometry at varying potentials between 0.1 and 0.6 V vs. Ag/AgCl (in 50 mV increments). These exemplary characterizations were performed in the blank buffer solution containing 100 µM of glutamate. The redox currents was sampled at 15 s following the potential step. An identical procedure can be followed using GOx-BMAE for the detection of 10 mM glucose. FIG. 7 shows exemplary hydrodynamic voltammograms of the glutamate bicomponent microneedle array electrodes, e.g., in which redox currents were sampled at t=15 s following the potential step. As is evident from the figure, the presence of glutamate caused a concomitant rise in the anodic current, corresponding to the oxidation of the $H_2O_2$ enzymatic product. The onset of the peroxide oxidation can occur at ~0.25 V vs. Ag/AgCl. To minimize the potential oxidation of interferents in real samples, a potential of 0.40 V vs. Ag/AgCl can be selected for further electrochemical implementations of the BMAE biosensor.

Figure 8A:
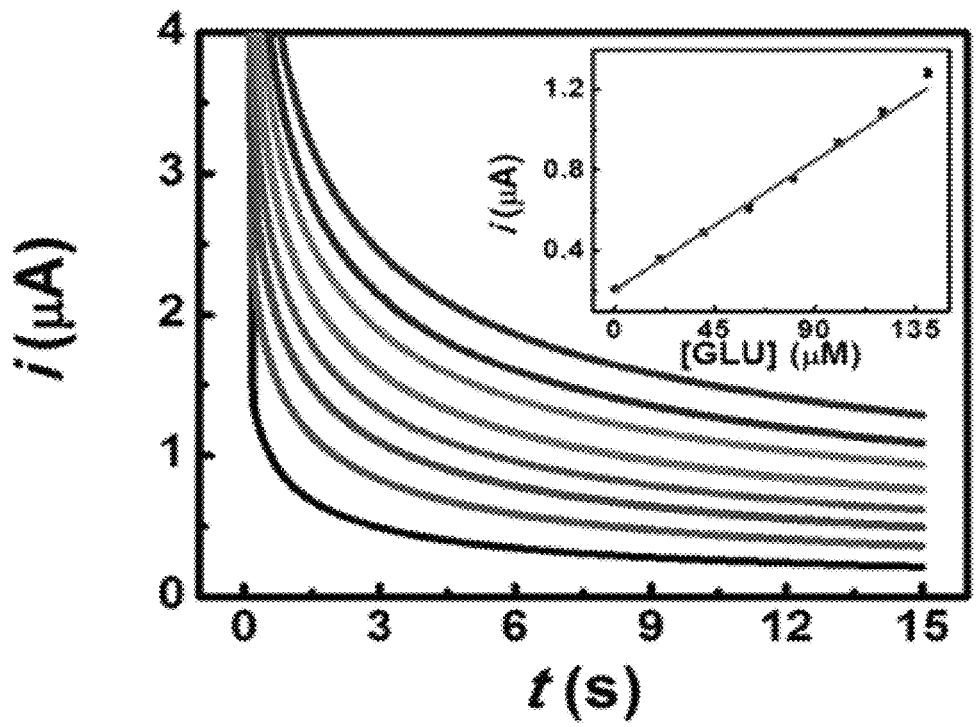
FIGS. 8A and 8B show exemplary chronoamperogram data plots recorded for increasing concentrations of glutamate.

Examples are described for biosensing of glutamate in a buffer matrix and human serum at the bicomponent microneedle array electrode. The sensitivity of the exemplary BMAE biosensor was evaluated using chronoamperometric potential steps to the selected potential of 0.40 V vs. Ag/AgCl. FIG. 8A shows a data plot of the average of triplicate chronoamperometric experiments for increasing levels of glutamate over the entire pathophysiological range (e.g., 0-140 µM in 20 µM increments, sampled at t=15 s) in a buffer matrix. A linear calibration plot ($R^2$=0.995) can be observed (as shown in the inset of FIG. 8A) over the entire range under investigation. The exemplary calibration plot exhibits high sensitivity ($s_x$=7.129 nA/µM) and a low deviation (RSD=3.51%); a limit-of-detection (LOD) of 3 µM can be estimated based on the signal-to-noise characteristics of the experimental data (S/N=3). The LOD lies well below normal physiological levels, reflecting the ability of the microneedle sensor to detect physiologic levels of glutamate.

Figure 8B:
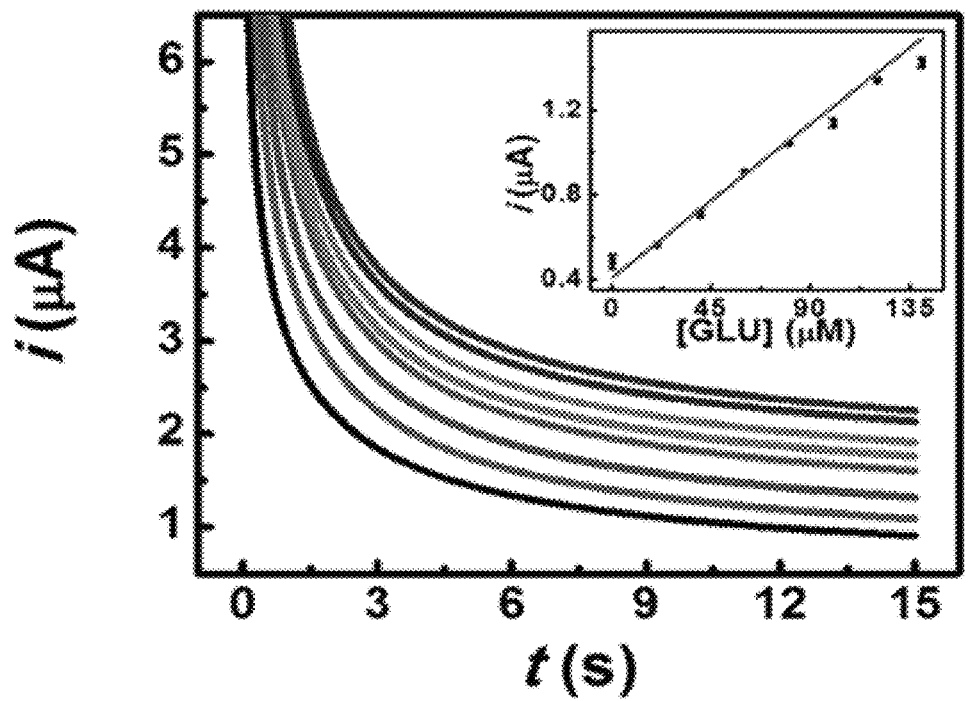

Following the calibration experiments in the buffer solution, exemplary implementations of the described BMAE biosensor was evaluated by quantification of glutamate in undiluted human serum samples. FIG. 8B shows a data plot of the average of triplicate chronoamperometric calibration experiments in human serum for increasing levels of glutamate over the 0-140 µM range (e.g., in 20 µM increments). As with the exemplary buffer study, a linear calibration plot can be observed (as shown in the inset of FIG. 8B; $R^2$=0.992) over the entire range. In addition, for example, the calibration data exhibit high sensitivity ($s_x$=8.077 nA/µM) and low deviation (RSD=6.53%). An LOD of 10 µM can be estimated based on the signal-to-noise characteristics of these data (S/N=3). As with the exemplary buffer experiments, the LOD obtained from the experimental data resides below the limit of normal physiological levels. The attractive behavior of the BMAE in untreated serum samples reflects the protective ability of the PPD film. Furthermore, the similar sensitivity obtained for both the buffer- and serum-based trials again can underscore the robustness of the PPD immobilization scheme despite the prolonged exposure of the biosensor to protein-rich serum medium.

Figure 9:
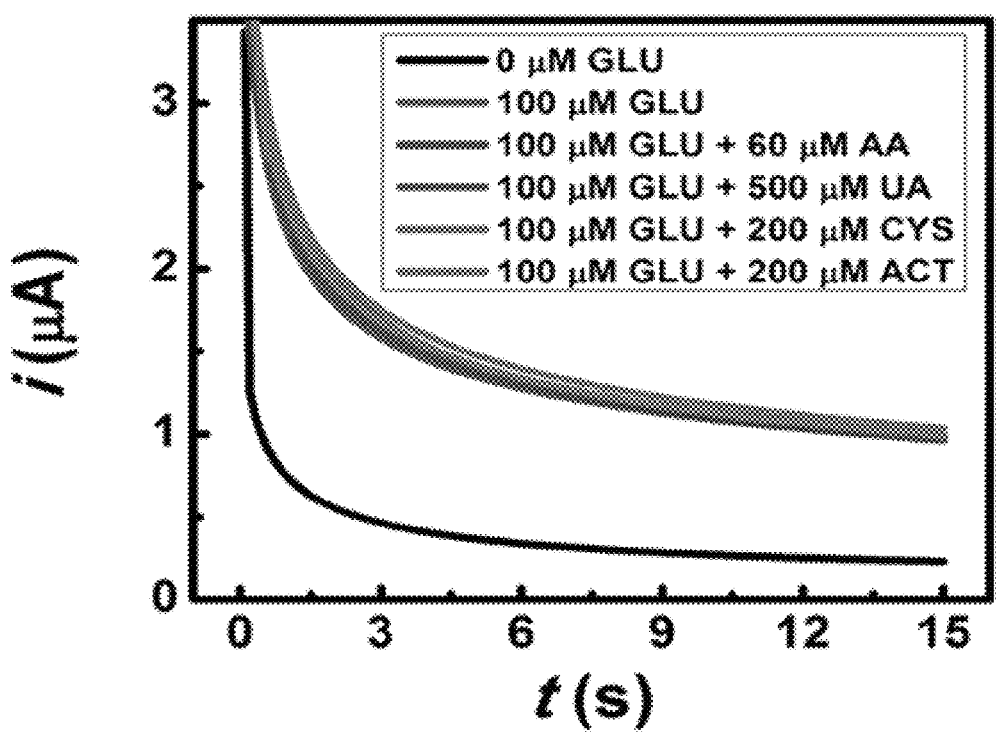
FIG. 9 shows exemplary chronoamperogram data plots recorded in 0.1 M phosphate buffer.

Examples are described for interference investigation(s) employing physiologically-relevant electroactive compounds. For example, another advantageous feature of the PPD coating includes its ability to reject coexisting electroactive interferents even at moderate oxidation potentials. Accordingly, the selectivity of the response was examined in the presence of physiological levels of ascorbic acid (60 µM), uric acid (500 µM), cysteine (200 µM), and acetaminophen (200 µM). FIG. 9 shows a data plot of exemplary chronoamperograms recorded in 0.1 M phosphate buffer (pH 7.40) for the blank buffer solution, 100 µM glutamate, and 100 µM glutamate in the presence of the electroactive physiological interferents ascorbic acid (AA, 60 µM), uric acid (UA, 500 µM), cysteine (CYS, 200 µM), and acetaminophen (ACT, 200 µM). The exemplary implementations were carried out under the same conditions as those represented in FIGS. 8A and 8B. FIG. 9 illustrates the negligible contribution imparted by the presence of these electroactive compounds upon the current signal for 100 µM glutamate. Physiological levels of ascorbic acid, uric acid, cysteine, and acetaminophen resulted in only 0.44%, 0.31%, 1.93%, and 6.37% average deviations from the 100 µM glutamate current response, respectively. Hence, natural metabolic fluctuations in the levels of these electroactive species are not expected to interfere with the in vivo quantification of glutamate using the exemplary BMAE device as an on-body biosensor.

Figure 10:
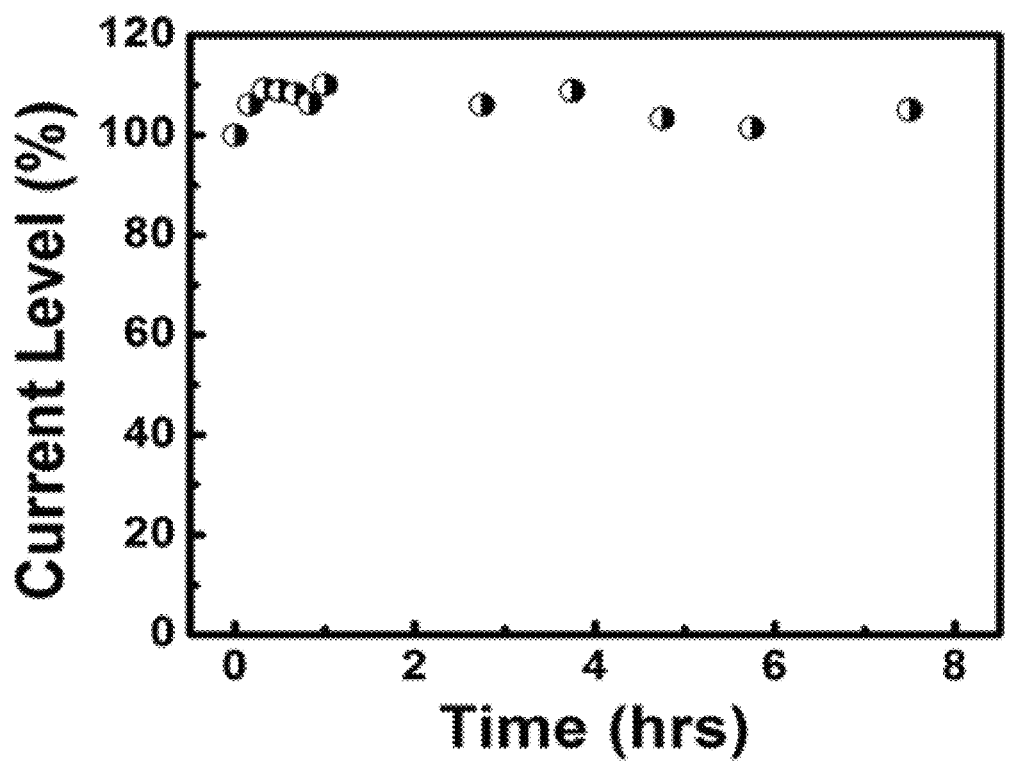
FIG. 10 shows exemplary data plots showing the stability of the glutamate response over extended time periods.

Exemplary implementations were performed for stability analysis of the exemplary bicomponent microneedle electrode array. For example, the ability to operate over prolonged periods with minimal deterioration in the current response can represent another important feature of on-body biosensors. Accordingly, the stability of the BMAE response was examined using a 100 μM glutamate solution over an eight-hour period. FIG. 10 shows a data plot showing stability of the glutamate response over extended time periods with each data item referenced to the original current level at t=0 (100%). In this exemplary implementation, data was generated from chronoamperograms recorded in 0.1 M phosphate buffer (pH 7.40 ) with 140 μM glutamate. The exemplary implementations were carried out under the same conditions as those represented in FIGS. 8A and 8B. The exemplary time-course profile of FIG. 10 indicates that the exemplary biosensor exhibits a highly stable current response, retaining 105% of the original signal level after eight hours of continuous sampling. In this example, the measured current never exceeded 110% of the original level over the entire time period. Consequently, the BMAE can be anticipated to perform reliably over extended periods associated with body-worn biosensors.

Figure 11A:
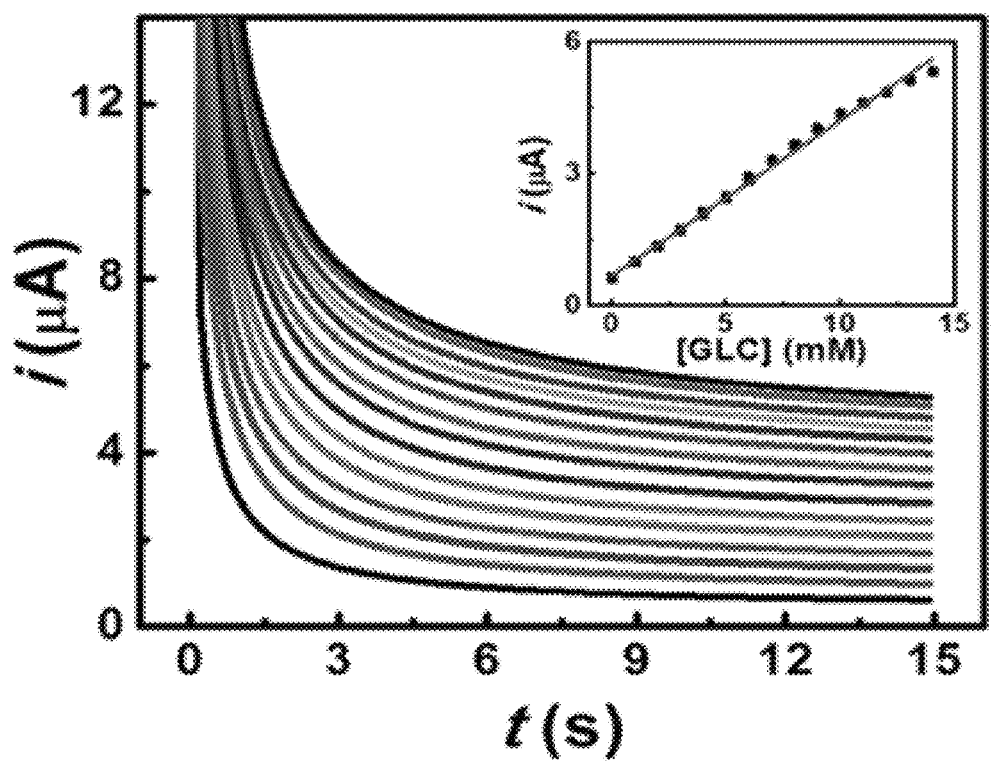
FIGS. 11A and 11B show data plots showing sensitivity of an exemplary glucose microneedle biosensor.

Examples are described for the biosensing of glucose with the exemplary bicomponent microneedle electrode array. For example, with the glutamate BMAE methodically characterized, the exemplary platform can be subsequently migrated for use as a glucose biosensor towards diabetic monitoring. GOx was confined within the BMAE cavities using a slight variant of the described GluOx immobilization process. This technique can be amenable to cost-per-quantity considerations, as stated above. FIG. 11A shows a data plot featuring chronoamperometric calibration data for increasing levels of glucose over the entire pathophysiological range (e.g., 0-14 mM in 1 mM increments) in a buffer matrix. A well-defined response can be observed over the entire range, leading to a linear calibration plot (as shown in the inset of FIG. 11A; $R^2$=0.996). In addition, these exemplary calibration data exhibit high sensitivity ($s_x$=0.353 μA/mM) and low deviation (RSD=6.44%, n=3), along with a LOD of 0.2 mM (S/N=3). It can be noted that the GOx-functionalized BMAE exhibited a lower sensitivity towards its substrate when compared with the GluOx-functionalized platform. For example, this can be attributed to the different PPD growth process, which may affect the transport properties of the substrate and product. Accordingly, the GluOx immobilization process can be followed when high sensitivity is desired.

Figure 11B:
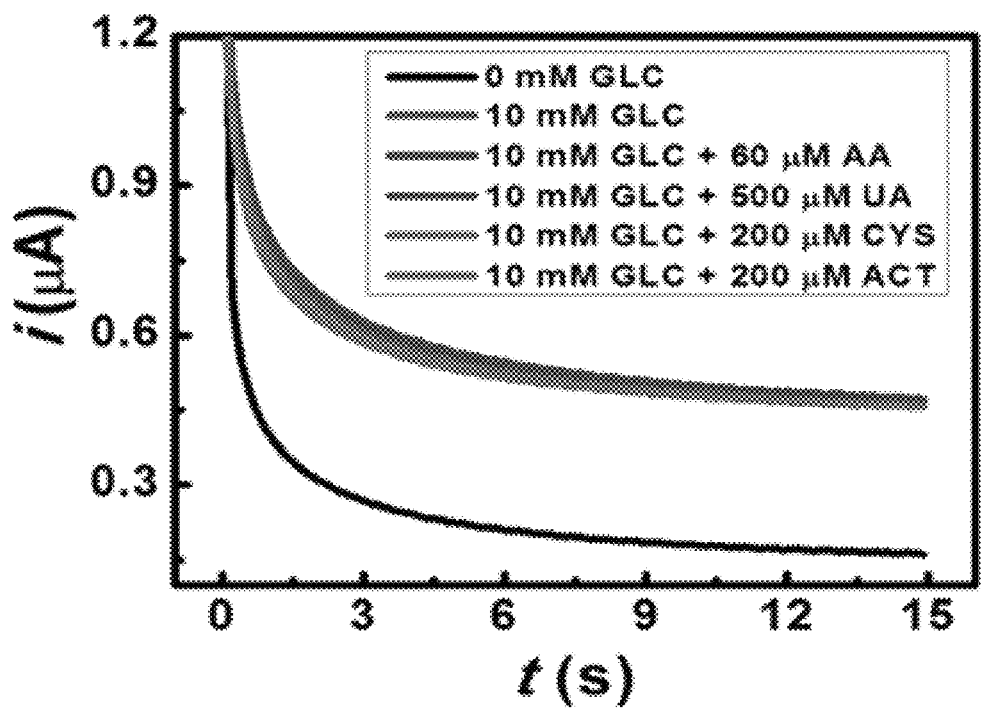

FIG. 11B demonstrates the high selectivity of the exemplary glucose microneedle biosensor. FIG. 11B shows a data plot of exemplary chronoamperograms recorded for the blank buffer solution, 10 mM glucose, and 10 mM glucose in the presence of the electroactive physiological interferents ascorbic acid (AA, 60 μM), uric acid (UA, 500 μM), cysteine (CYS, 200 μM), and acetaminophen (ACT, 200 μM). FIG. 11B illustrates the contribution imparted by the presence of potential electroactive interferents upon the current signal for 10 mM glucose. Physiological levels of ascorbic acid, uric acid, cysteine, and acetaminophen resulted in negligible deviations of 1.07%, 0.88%, 1.65%, and 2.21%, respectively, from the current response for 10 mM glucose. Consequently, as with the exemplary interference implementation conducted with the glutamate BMAE, natural metabolic fluctuations of these compounds is not be anticipated to interfere with the monitoring of glucose.

An exemplary stability evaluation of the GOx-functionalized BMAE was performed using a buffer solution containing 10 mM glucose over an 8-hour period. The GOx BMAE yields a highly stable current response, with 97% of the original signal level extracted at the conclusion of the measurement period. In this example, throughout the time period under investigation, the measured current response never fell below 87% of the original level. The similar results described earlier with the GluOx-functionalized BMAE indicate that both PPD-based immobilization schemes can yield a stable response over a prolonged period of continuous use.

The disclosed technology described for this embodiment includes a bicomponent microneedle array biosensor platform that can be used for minimally-invasive glutamate and glucose quantification. The bicomponent microneedle design merges the inherent advantages of solid and hollow microneedles in order to form a microcavity that can allow the electropolymeric entrapment of an enzyme, which can provide protection for the enzyme layer upon skin penetration, and can eliminate the need for the extraction of biological fluids. Using a poly(o-phenylenediamine) thin-film for entrapping the enzymes glutamate and glucose oxidase can enable the highly sensitive, selective, stable, and rapid electrochemical detection of glutamate and glucose, respectively. The high fidelity detection of glutamate in undiluted human serum samples over the entire pathophysiological range can further substantiate the utility of the platform as a practical on-body biosensor. The exemplary patch-type on-body biosensor can enables the transdermal monitoring of a number of relevant metabolites.

In another embodiment of the disclosed technology, a minimally-invasive, multiplexed, multi-component microneedle actuator device that enables the controlled delivery of multiple therapeutic agents is described. This embodiment can comprise the same embodiment(s) like those previously described, and can therefore implement the entirety of functionalities of the individual embodiments on a single embodiment. In this described embodiment, a device can deliver a drug in response to injury/trauma in an autonomous, minimally-invasive, and controlled manner that leverages microneedle arrays as the delivery structure, which can be referred to as a smart NanoPharmacy-on-A-Chip. For example, microneedle array(s) can be integrated on an adhesive patch that is placed on the skin in order to deliver on demand a targeted therapeutic intervention transdermally. The exemplary technology can integrate the microneedle platform with stimuli-responsive conducting polymer nanoactuators (with tunable permeability through an autonomous porosity change controlled by an integrated sensing or enzyme-logic system). For example, the disclosed biosensor-actuator device can be used to aid in the rapid administration of multiple therapeutic agents and counteract diverse biomedical conditions.

The described embodiment includes multiple individually-addressable channels on a single microneedle array, each paired with its own reservoir and conducting polymer nanoactuator, which are used to deliver various permutations of the multiple unique chemical species. For example, upon application of suitable redox potentials to the selected actuator, the conducting polymer is able to undergo reversible volume changes, thereby serving to release a model chemical agent in a controlled fashion through the corresponding microneedle channels. Exemplary implementations of the drug delivery contingent of the disclosed biosensor-actuator device were performed and are described herein. For example, time-lapse videos were recorded and can offer direct visualization and characterization of the membrane switching capability, and, along with calibration investigations, confirmed the ability of the device to alternate the delivery of multiple reagents from individual microneedles of the array with high precision and temporal resolution. Analytical modeling is described herein, which can offers prediction of the volumetric flow rate through a single microneedle, and accordingly, can be used to assist in the design of the microneedle arrays.

In some examples, conducting polymers such as polypyrrole (PPy), polyaniline (PANI), and poly(3,4-ethylenedioxythiophene) (PEDOT) can be employed for utilization in the described controlled release systems and drug delivery actuators. These exemplary materials include unique properties (e.g., PPy in particular), which include their reversible mechanical behavior as "artificial muscles" and their ability to change porosity and undergo volume changes in response to applied electrochemical stimuli. The disclosed actuator technology engineers these exemplary materials in devices and systems to provide a means to deliver medications in an effective and minimally-invasive manner, e.g., which can be implemented in practical body-worn devices for the amelioration of disease and injury in the acute phase, amenable to extended durations of pain-free wear.

Figure 12A:
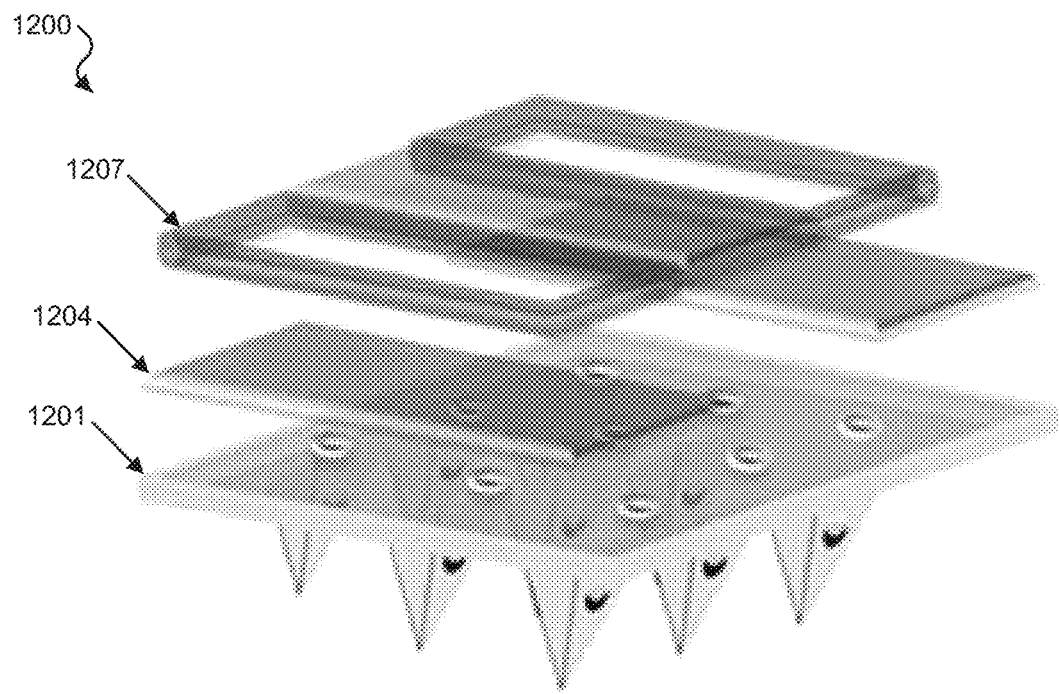
FIGS. 12A and 12B show a schematic illustration of an exemplary microneedle-based multi-channel, multiplexed drug delivery actuator device.

FIG. 12A shows a schematic illustration of an exemplary microneedle-based multi-channel, multiplexed drug delivery actuator device 1200. The device 1200 includes a hollow microneedle array 1201. The device 1200 includes a gold-sputtered polycarbonate membrane 1204, which can be functionalized with sodium dodecylbenzenesulfonate-doped polypyrrole (PC/Au/PPy/DBS). The device 1200 includes a polydimethylsiloxane (PDMS) reservoir 1207 that can include multiple reservoirs to store chemical (therapeutic) agents.

Figure 12B:
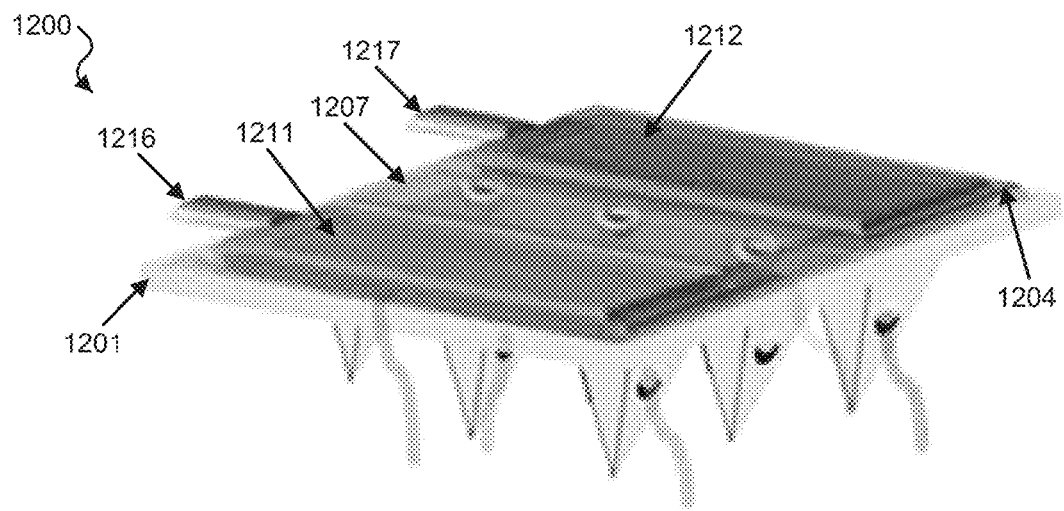

FIG. 12B shows a schematic illustration of the assembled multiple-channel drug delivery actuator device 1200, in which the reservoir 1207 is configured to have two exemplary reservoirs containing two different drugs, e.g., drug 1211 and drug 1212. The schematic in FIG. 12B also shows the assembled multiple-channel drug delivery actuator device 1200 including electrode connections 1216 and 1217 corresponding to the two reservoirs containing the drug 1211 and 1212, respectively.

The disclosed biosensor-actuator device enables the controlled and switchable delivery of multiple therapeutic agents. Exemplary implementations of the described device utilized still-frame imaging and real-time video capture to show the alternating release of dye from different microneedles from the same array platform. For example, image analysis software (e.g., such as ImageJ) and ultraviolet-visible (UV-Vis) spectrophotometry were employed to demonstrate the switching accuracy and repeatability of the microneedle volumetric flow rate. These exemplary results were correlated with an analytical model that assesses the fluid flow characteristics through a single microneedle, which can subsequently be used to assist in the design and development of other embodiments of the disclosed multi-section microneedle arrays technology, e.g., which can be applied for practical body-worn devices that can deliver on demand different therapeutic agents.

By employing the disclosed biosensor-actuator technology, a unique drug therapy can be released at each microneedle constituent of the array, thereby enabling custom-tailored dosages of medications. The described biosensor-actuator technology includes an active solid-state device that requires no moving parts or integrated microelectromechanical systems (MEMS). Thus, this simplifies low-profile device design and eliminates the need for sophisticated microfluidics-based components, which can complicate system architecture and increase both size and cost. Additionally, for example, the described microneedle multi-drug delivery technology can be implemented with implantable devices, and thus is well-positioned to serve as the core component in an autonomous 'wearable nanopharmacy' in connection to multiplexed microneedle sensor arrays.

Exemplary materials and methods to implement the disclosed embodiment of the technology are presented. The following chemicals and reagents were used in the described implementations, which included sodium dodecylbenzenesulfonate (NaDBS), methylene green (MG), chresol red (CR), potassium phosphate monobasic ($KH_2PO_4$), and potassium phosphate dibasic ($K_2HPO_4$), e.g., which were obtained from Sigma Aldrich (St. Louis, Mo.) and were used without further purification or modification. Pyrrole was distilled daily under vacuum and stored at 4° C. prior to electropolymerization. All reagents were prepared in a 0.1 M phosphate buffer solution (pH 7.00). Ultrapure water (18.2 MΩ·cm) was employed in all of the exemplary implementations. Polydimethylsiloxane (PDMS) was obtained from Dow Corning Corp. (Midland, Mich.) and mixed by hand in a 10:1 polymer: fixing agent ratio. The suspension was then poured into a custom mold and degassed in a vacuum desiccator. Subsequently, the PDMS suspension was baked at 110° C. for 15 min. The resultant structures were exposed to UVO ozone (Jetline Co., Irvine, Calif.) at a gas flow rate of 3 sccm for 5 minutes. 25 mm-diameter black polycarbonate (PC) track etch membrane filters were procured from SPI Supplies (West Chester, Pa.); these filters possessed a pore diameter of 600 nm.

Figure 13A:
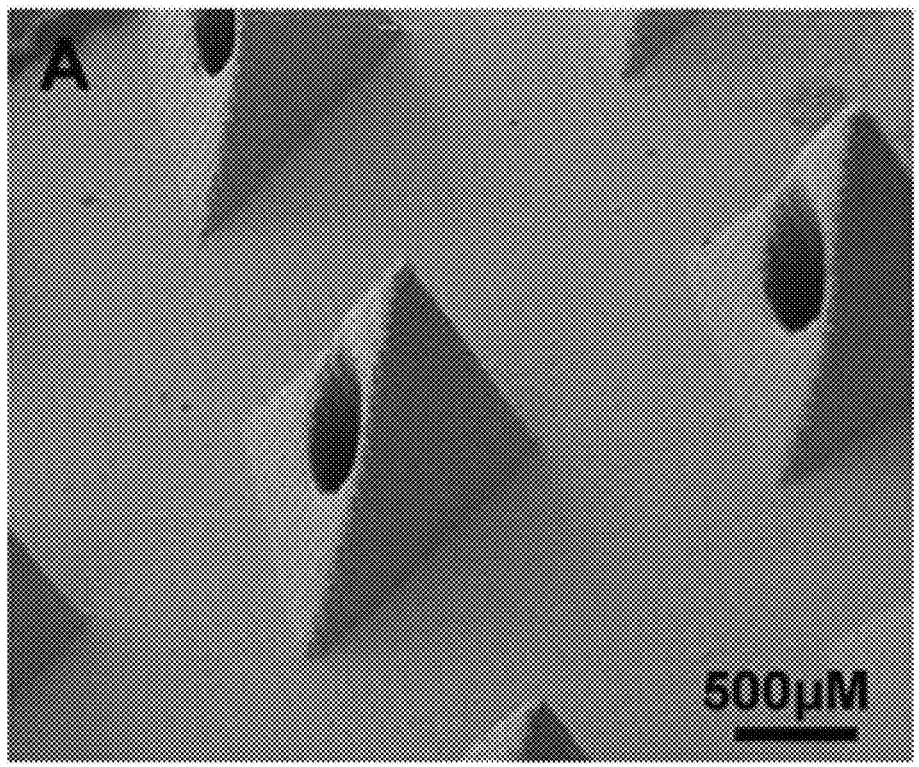
FIGS. 13A and 13B show SEM images of the surface morphology of an exemplary hollow microneedle array.
Figure 13B:
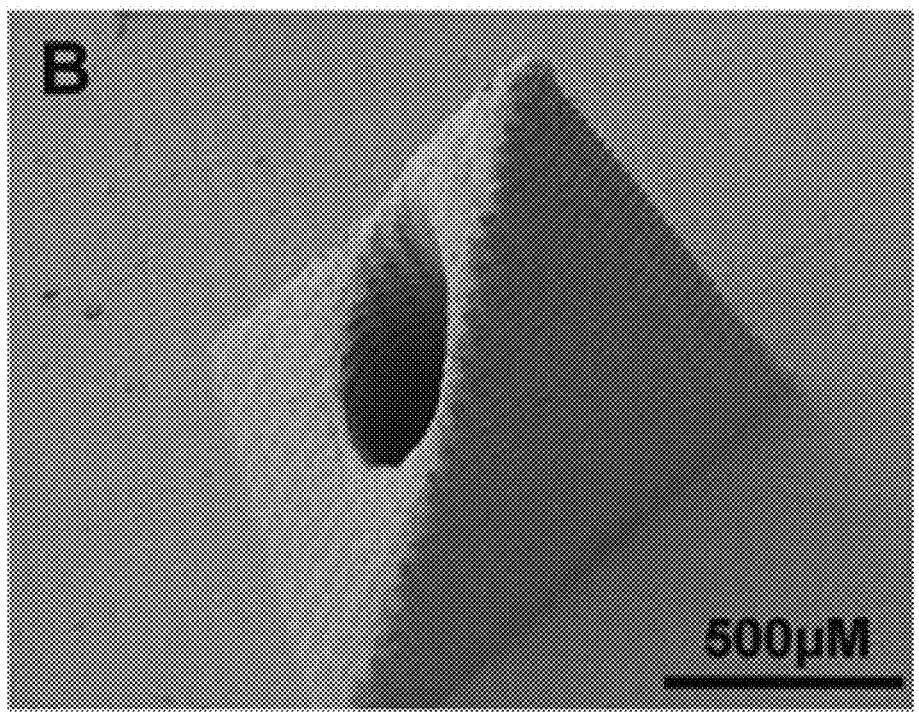

The instrumentation used in the described implementations included the following, which was utilized in exemplary demonstrations and implementations of the disclosed embodiment under exemplary conditions disclosed herein. A CH Instruments (Austin, Tex.) model 1232A electrochemical analyzer was employed for all of the electrochemical measurements. An Ag/AgCl wire reference electrode and a platinum wire counter electrode were used to establish a three-electrode electrochemical system. A Shimadzu (Kyoto, Japan) UV-2450 UV-VIS spectrophotometer was used for all of the optical measurements. A consumer digital video camera/camcorder was employed to capture the still-frame images and videos. A Philips XL30 field emission scanning electron microscope (Amsterdam, the Netherlands) was employed to investigate the surface morphology of the microneedle array. The arrays were coated with a gold film (e.g., ~15 nm) using an Emitech (East Sussex, UK) K575X sputtering instrument prior to SEM imaging. The resultant electron micrographs are shown in FIGS. 13A and 13B. FIG. 13A shows an SEM image detailing the surface morphology of an exemplary hollow microneedle array. FIG. 13B shows an enhanced view of the scanning electron micrograph of a single needle of the exemplary hollow microneedle array featuring a well-defined cylindrical lumen. The PC membranes were sputtered with a gold thin film (~75 nm) using an Emitech K 575 X sputtering instrument prior to the deposition of the NaDBS-doped PPy conducting polymer.

The fabrication of the exemplary hollow microneedle arrays used in the described implementations was performed in the following manner. The hollow microneedle arrays were fabricated, in which, the microneedle designs were originally prepared using Solidworks (Dassault Systemes S.A., Velizy, France). Substrate support structures were subsequently created with Magics RP 13 (Materialise NV, Leuven, Belgium). For example, the hollow needles were pyramidal in shape with a triangular base. For example, the dimensions of each hollow microneedle were as follows: an edge length of 1174±13 µm, a height of 1366±15 µm, and a vertical cylindrical bore of 342±5 µm diameter on one of the faces of the pyramid structure. The hollow needles were arranged into 3×3 square arrays with 2 mm periodicity. For example, substrates for the microneedle arrays were 10 mm×10 mm in extent and possessed thickness values of 500 µm.

The preparation of the exemplary electrically-actuatable nanoporous membranes (e.g., PC/Au/PPy/DBS membranes) used in the described implementations was performed in the following manner. For example, gold-sputtered PC membranes (PC/Au) (e.g., pore diameter ~600 nm, porosity ~0.2) were attached at the periphery to a copper wire using silver conductive epoxy. A solution of 0.1 M NaDBS was purged with nitrogen for 40 min after which the pyrrole monomer was added to achieve a final concentration of 0.25 M. Subsequently, the PC/Au membrane was immersed in the solution and served as the working electrode in an electrochemical cell while 0.6 V vs. Ag/AgCl was applied for 10 min. The application of this exemplary potential for the given amount of time resulted in optimal deposition of the polypyrrole polymer on the PC/Au membrane, thereby minimizing the leaching of the solution through the membrane under the 'closed' state while enabling the solution to flow at appreciable rates under the 'open' state. Following electropolymerization of polypyrrole/DBS (PPy/DBS), the PC/Au/PPy/DBS membranes were rinsed with deionized water and stabilized by cycling between −1.1 V and 0.5 V vs. Ag/AgCl for ten iterations in the buffer solution. This process enabled the membrane to swell in the reduced state (−1.1 V) and contract in the oxidized state (0.5 V) in a reversible manner. When not in use, the membranes can be stored in the buffer solution at room temperature.

The fabrication of the exemplary drug delivery actuator contingent of the disclosed biosensor-actuator device used in the described implementations was performed in the following manner. The PC/Au/PPy/DBS membranes were cut into slivers possessing dimensions of approximately 12 mm×4 mm. These slivers were subsequently affixed to the reverse side of the exemplary 3×3 microneedle array using adhesive epoxy such that one sliver completely covered a column of three microneedles. The center column of the array was obstructed using modeling clay, enabling formation of two individually-addressable electrically-actuatable channels, exemplified in the component-level schematic illustrated in FIG. 12A. Electrical leads were attached using silver epoxy to each of the two PC/Au/PPy/DBS membranes to facilitate ohmic contact with each actuator. The PDMS dual-channel reservoir was subsequently aligned over the membranes and affixed using adhesive epoxy. As shown in FIG. 12B, the reservoirs were finally loaded with ~20 µL of the model chemical agent(s).

Figure 14:
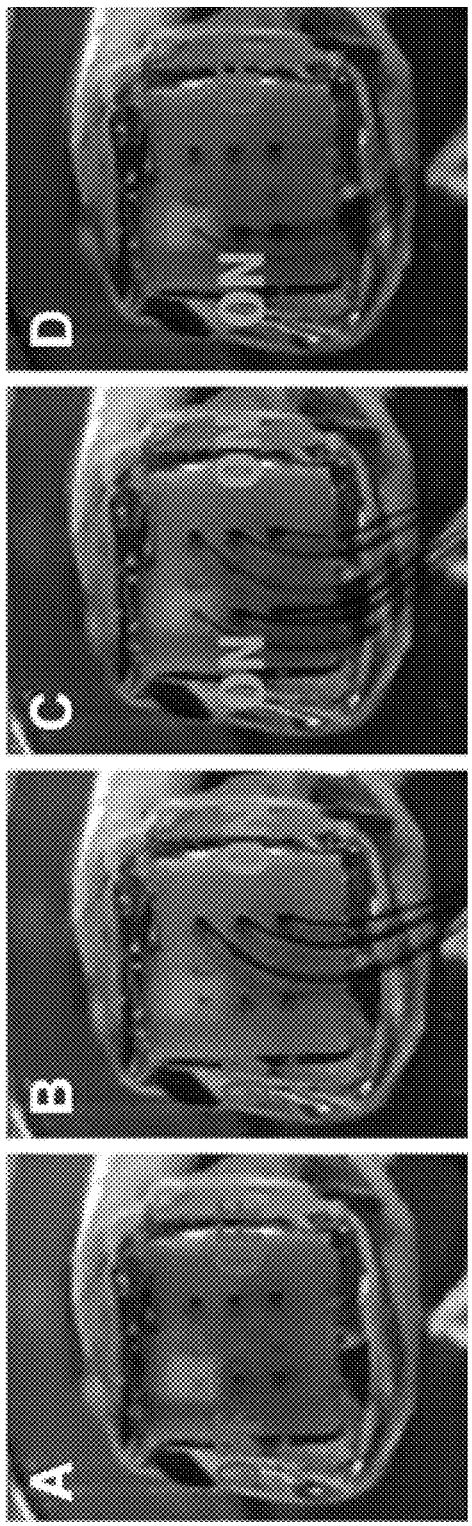
FIG. 14 shows images of triggered release of methylene green from the individually-addressable reservoirs of an exemplary microneedle-based drug delivery actuator device.

Initial implementations of the exemplary microneedle array actuator device were aimed at validating and visualizing the switching capability of the PC/Au/PPy/DBS membrane and the dual-channel operation. For example, both reservoirs in the assembled multiplexed drug delivery actuator, e.g., reservoir 1 (R1) and reservoir 2 (R2), were initially loaded with 12 mM of methylene green (MG) dye and immersed in a buffer solution along with the counter and reference electrodes. Continuous agitation at a constant speed (e.g., 140 rpm) was applied with a magnetic stirring bar. The DBS-doped PPy membrane entered the reduced state and engorged upon biasing with −1.1 V vs. Ag/AgCl, thereby obstructing the flow of the solution through the porous material. Ejection of the MG dye at either channel was not observed at this potential (represented as being in the 'OFF' state), as shown in image (A) of FIG. 14. Subsequently, the R2 membrane nanoactuator was maintained at the reduced state (−1.1 V vs. Ag/AgCl, 'OFF') and the membrane at R1 was switched to the oxidized state ('ON') by applying a potential of 0.5 V vs. Ag/AgCl. This "ON" state caused the DBS-doped PPy membrane to become oxidized and contract, thereby facilitating the flow of the solution through the nanoporous membrane and subsequently through the microneedles. As can be observed from the image (B) of FIG. 14, the emission of MG from R1 is visible whereas R2 remained closed and did not permit the release of the dye. Following this operation, R1 was kept at the oxidized state (0.5 V vs. Ag/AgCl, 'ON') while R2 was switched to the oxidized state (0.5 V vs. Ag/AgCl, 'ON'), thus releasing MG from both reservoirs (as shown in image (C) of FIG. 14). Subsequently, R1 was switched to the reduced state "OFF" and R2 was kept at the oxidized state "ON", as shown in image (D) of FIG. 14. This controlled and alternating release of MG from the individual reservoirs by switching potentials on the nanoporous membranes was illustrated in a real-time manner. The execution of repeated 'ON-OFF' cycles demonstrates that the drug delivery array maintains its ability to open and close in a cyclic fashion, e.g., even following 10 iterations or more. Furthermore, the temporal duration (~30 s) required to observe the release of MG at the tenth cycle was identical to that of the first cycle. In the exemplary implementations, the time duration for complete flow shutoff was approximately 35 s following the application of the "OFF" potential. Based on the above results, R1 was loaded with CR dye and R2 was loaded with MG dye. All four "ON/OFF" permutations were applied. The controlled ejection of dye from alternating microneedle array reservoirs was demonstrated based on the potential applied to each nanoporous membrane.

Figure 15:
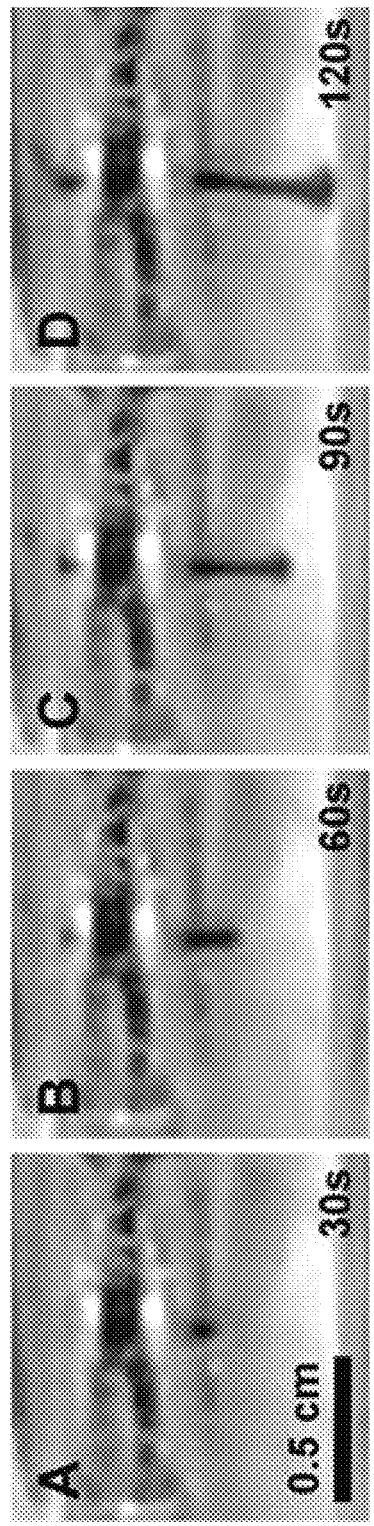
FIG. 15 shows time-lapse still frame images of the release of methylene green dye from a single microneedle of an exemplary microneedle-based drug delivery actuator device.

The exemplary implementations included image analysis and UV-Vis spectrophotometry techniques to analyze the drug delivery capability of the microneedle array by experimentally quantifying the flow rate of the MG dye from a single microneedle channel. FIG. 15 illustrates the release of MG from a single microneedle into a quiescent buffer solution at fixed time intervals of 30 s. FIG. 15 shows exemplary time-lapse still frame images of the release of methylene green (MG) from a single microneedle at distinct time intervals of 30 s (shown in image (A)), 60 s (shown in image (B)), 90 s (shown in image (C)), and 120 s (shown in image (D)). For example, a potential of 0.5 V (vs. Ag/AgCl) was applied to open the nanoporous membrane and release the dye during the implementations. The exemplary flow rate of released dye was determined to be 6.3±0.4 µL/hour (n=10) through analysis of multiple time-lapse video still-frames. After 30 s of applying this potential, the dye began to emerge from the microneedle aperture. A small column of dye was clearly observed at 60 s. A well-defined column of dye possessing a height of approximately 0.5 cm was observed after 120 s. Afterwards, the estimated experimental flow rate of the released dye was calculated by measuring its column height (h) with image processing software (e.g., ImageJ) in conjunction with the flow rate equation (Eq. 1):

$$Q = \frac{\pi d^2 h}{4(t - t_0)} \tag{1}$$

where d is the microneedle channel diameter and h is the column height associated with a particular point at time t.

Figure 16:
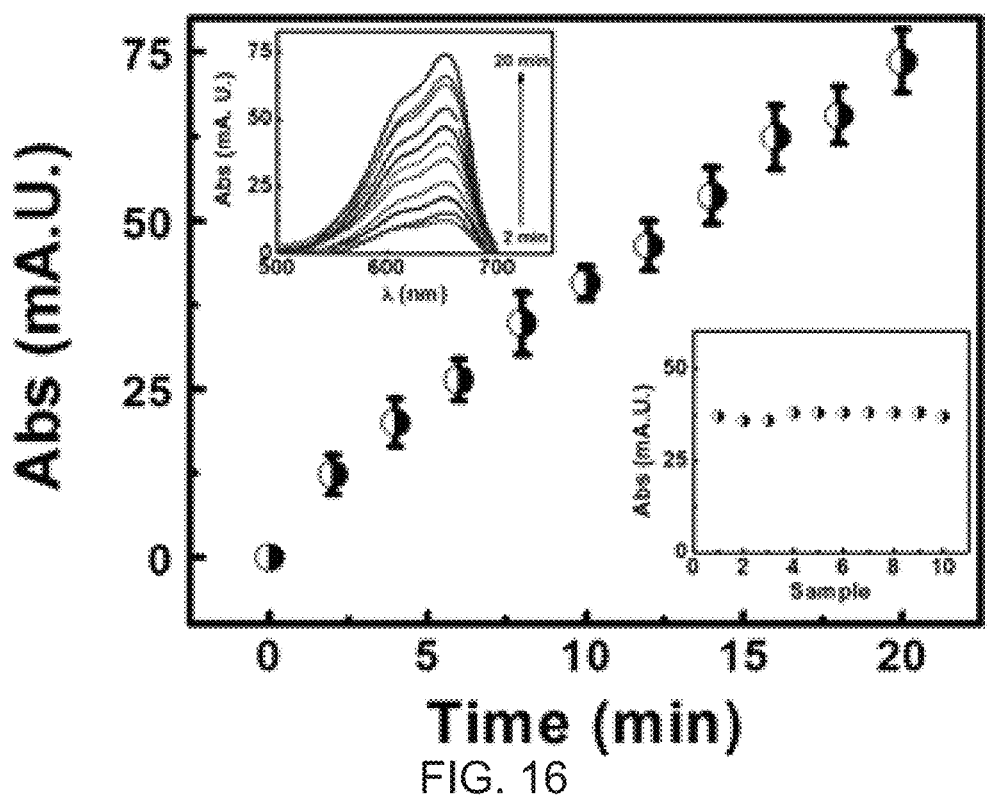
FIG. 16 shows an exemplary UV-Vis spectrum data plot illustrating the absorbance for the release of methylene green dye from an exemplary microneedle.

UV-Vis spectrophotometry was employed to quantify the amount of released dye and subsequently assess the microneedle flow rate as well as the repeatability of the release. FIG. 16 shows an exemplary UV-Vis spectrum data plot illustrating the absorbance for the release of methylene green (MG) dye from a single microneedle at a 2 minutes release interval over a 20 minute period. The upper (top left) inset data plot displays the UV-Vis spectra, and the lower (bottom right) inset data plot displays absorbance of 10 distinct experimental implementations over a constant time release. The lower (bottom right) inset data plot in FIG. 16 substantiates the reproducibility of the MG release from the drug-delivery nanoactuator over the same release time. The maximum deviation among these ten repetitions was 5.5% from the original absorbance, which was measured at the maximum wavelength. Linear regression analysis was performed on the absorbance vs. time plot, yielding a slope of 3.5 mOD min$^{-1}$ with a high coefficient of determination ($R^2$=0.993) and low relative standard deviation (RSD=2.74%, n=3); this result indicated a constant release of dye from the microneedle. From these implementations, the fluid flow rate was calculated to be 5.5±0.2 μL/hour, which is in good agreement with the image analysis data collected from the time-lapse video still-frames. The fabricated membranes exhibited excellent reproducibility, e.g., calculated flow rates deviated by less than 10% under identical electropolymerization conditions.

Figure 17:
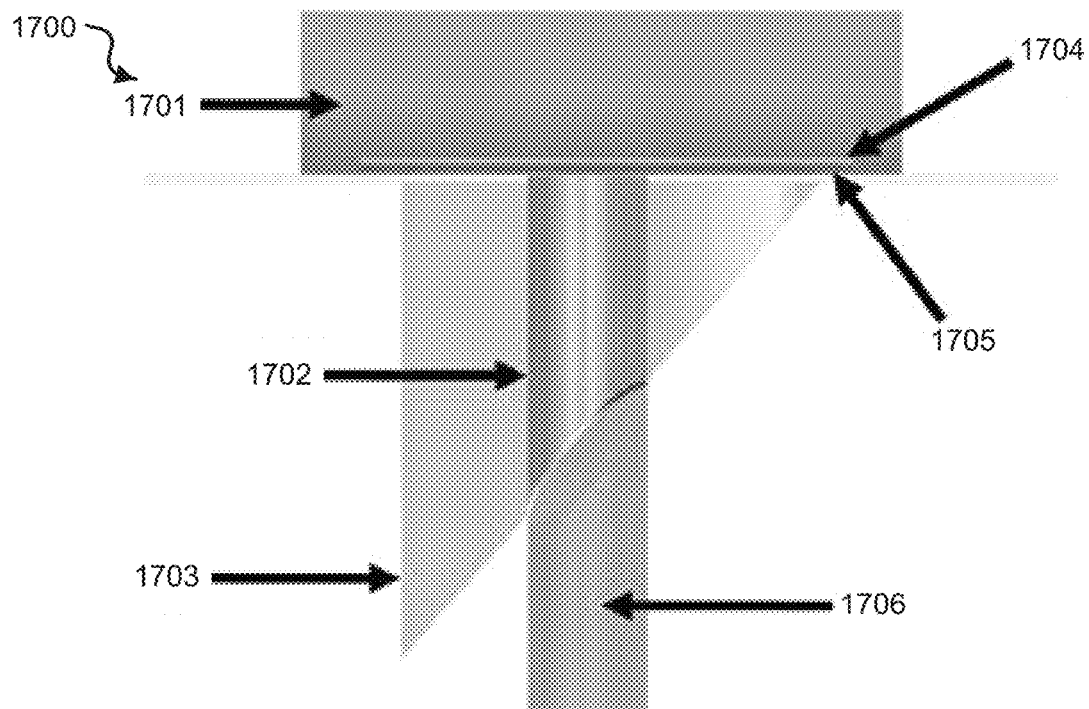
FIG. 17 shows a schematic of an exemplary microneedle during drug delivery.

The understanding of the fluid flow characteristics of the microneedle array is important for delivering the precise amount of drug to subcutaneous tissue during transdermal drug delivery. In some examples, to augment this understanding and to analytically estimate the drug delivery capability, the fluid flow characteristics of a single microneedle can be modeled via the Modified Bernoulli Equation (Eq. 2):

$$\frac{P_1}{\rho g} + \frac{V_1^2}{2g} + z_1 = \left(\frac{P_2}{\rho g} + \frac{V_2^2}{2g} + z_2\right) + \sum f \frac{LV_2^2}{D 2g} + \sum \frac{EV_2^2}{2g} \quad (2)$$

where $P_1$ and $P_2$ are the atmospheric and microneedle outlet pressure, $V_1$ and $V_2$ are the average fluid velocities, $z_1$ and $z_2$ are the heights at the top of the reservoir and microneedle outlet respectively, f is the friction factor, ρ is the fluid density, L is the channel or pore length, and D is the hydraulic diameter. FIG. 17 shows an exemplary schematic of a single microneedle 1700 during drug delivery. The schematic shows the following exemplary microneedle components including: a reservoir 1701 (e.g., which can store a chemical agent, such as a drug), a lumen structure 1702 (e.g., which can be a duct or cavity of a tubular structure, sized to a 342 μm diameter), a hollow microneedle structure 1703, an electrically-actuatable nanoporous membranes 1704 (e.g., Au/PPY/DBS nanoporous membrane), a PC membrane 1705, and the released chemical agent exiting the lumen 1706.

The second term in Eq. 2 refers to the friction losses through the actuating nanopores, polycarbonate membrane, and microneedle channel, as shown in expanded form (Eq. 3):

$$\sum f \frac{L}{D} = f_{pores} \frac{L_{pores}}{D} \frac{\tau_{pores}}{\epsilon_{pores}} + \quad (3)$$

-continued $$f_{membranes} \frac{L_{membrane}}{D} \frac{\tau_{membrand}}{\epsilon_{membrane}} + f_{microneedle} \frac{L_{microneedle}}{D}$$

where τ and ε represent the tortuosity and porosity of the nanopores and polycarbonate membranes, respectively and D is the diameter of a single microchannel (e.g., 342 μm). The porosity of the PC membrane 1705 can be configured to 0.1 and the porosity of the actuating nanopores can be configured to 0.4, e.g., due to the pore narrowing created by the Au/PPy/DBS functionalization. For example, an approximate tortuosity value of 1.5 was assigned to the PC membrane and the actuating nanopores to take into account the increased channel curvature created by the nanopores. The respective friction factors were calculated according to Stokes flow theory for water flow in microchannels, where the product of the friction factor and Reynolds number (fRe=64) utilized for macroscale laminar flow in circular channels is employed. The friction factors for each flow section can be obtained by the Reynolds numbers obtained for fluid flow in each of the three flow sections of the microneedle channel, as shown in Table 1. Table 1 shows dimensions and flow characteristics of a single microneedle channel.

TABLE 1

| Flow Section | Length (μm) | Total Cross Sectional Area | Re |
|---|---|---|---|
| Microneedle Channel | 1366 | $A_c$ | 6 × 10$^{-3}$ |
| Polycarbonate Membrane | 7 | (0.2) $A_c$ | 5 × 10$^{-5}$ |
| Nanoporous Membrane | 0.75 | (0.4) $A_c$ | 9 × 10$^{-5}$ |

The values presented in Table 1 are calculated according to the following exemplary considerations. For example, $A_c$ is the cross sectional area of the microneedle [$\pi(D_{microneedle})^4/2$]. The Reynolds number (Re=ρVD/μ) was calculated using the density (ρ=1000 kg/m$^3$) and viscosity (μ=1.000 N s/m$^2$) of water at room temperature. The velocity used to estimate the Reynolds number for fluid exiting the microneedle channel was determined a priori by averaging the experimental velocities obtained by image analysis and UV-Vis spectrophotometry. Furthermore, the a priori velocities for the polycarbonate membrane and the nanoporous membrane were obtained by utilizing Conservation of Mass for incompressible fluids ($V_1 A_1 = V_2 A_2$) in conjunction with the average experimental velocity to calculate the corresponding Reynolds numbers.

The last term (ΣK) in Equation (2) represents the sum of minor losses due to the inlet, exit, and hydrodynamic development length, which is shown in expanded form below:

$$\Sigma K = K_{inlet} + K_{outlet} \quad (4)$$

where $K_{inlet}$ and $K_{outlet}$ are loss coefficient factors for a square edge inlet (0.5) and for an exit (1) typically associated with hollow microneedles.

An expression (Eq. 5) for the theoretical flow rate of the fluid exiting the microneedle channel can be formed by assuming quiescent flow at the top of the reservoirs ($V_1$=0), and negligible pressure gradients throughout the flow network ($\Delta P = P_1 - P_2 = 0$):

$$Q_2 = A_o \sqrt{\frac{3g(z_1 - z_2)}{\Sigma f \frac{L}{D} + \Sigma K}} \quad (5)$$

The theoretical flow rate calculated by Eq. 4 and the experimental flow rates obtained through image analysis and UV-Vis spectrophotometry were in good agreement, e.g., validating the veracity of the microneedle fluid flow model presented herein, as shown in Table 2. Table 2 exhibits a comparison of calculated theoretical and experimental microneedle flow rates.

TABLE 2

|  | Flow Rate ($Q_2$) (μl/hr) |
| --- | --- |
| Theoretical Model | 6.4 |
| Image Analysis | 6.3 ± 0.4 |
| UV-Vis Spectrophotometry | 5.5 ± 0.2 |

The ability to transdermally release multiple drugs may be important for the autonomous treatment of metabolic syndromes (e.g., a combination of hypertriglyceridemia, hypertension, and insulin dependent diabetes mellitus), human immunodeficiency virus, and other chronic medical conditions. The disclosed embodiment presents a self-contained multiplexed drug delivery system that utilizes arrays of microneedles coupled with conducting polymer nanoactuators for the controlled release of fluidic agents. The ability of the exemplary PPy/DBS conducting polymer to undergo volumetric changes with applied electrical potentials permits the release of fluid in a controlled and switchable fashion, e.g., without the need for moving parts or integrated microelectromechanical systems. These nanopore-actuated microneedle arrays are well suited for integration into wearable drug delivery devices, in which cost and power constraints must be minimized.

For example, a method to sense an analyte and deliver a therapeutic agent is described, e.g., which can be implemented using the described devices and systems of the disclosed embodiment. The exemplary method can include a process to detect a signal produced by an analyte at an interface with a functionalized probe configured to electrochemically interact with the analyte within a biological fluid, in which the signal is transduced to an electrical signal by the functionalized probe. For example, the functionalized probe can be one of an array of multiple functionalized probes, and the functionalized probe can be chemically functionalized to interact with one or more target analytes in the fluid. For example, the biological fluid can include at least one of transdermal fluid, intraocular fluid, vitreous humor, cerebrospinal fluid, extracellular fluid, interstitial fluid, plasma, serum, lacrimal fluid, saliva, perspiration, mucus, or blood, among other biological fluids in a living organism. The exemplary method can include a process to process (e.g., implementing signal processing techniques) the electrical signal to determine a parameter of the analyte (e.g., such as the concentration of the analyte). The exemplary method can include a process to, e.g., based on the determined parameter, apply an electrical stimulus to a valve (e.g., in which the valve can be a porous polymer film having pores of a reversibly tunable porosity, as described herein), in which the valve attached to a container containing a therapeutic agent. The exemplary method includes the electrical stimulus altering the permeability of the pores, e.g., from a closed state to an open state, thereby releasing the therapeutic agent into the biological fluid. For example, the therapeutic agent can include, but is not limited to, a drug, vaccine, hormone, vitamin, anti-oxidant, or pharmacological agent.

The disclosed multiple-drug delivery microsystem can be integrated with the described microneedle sensor array, e.g., coupling multiplexed analyte detection with the corresponding therapeutic intervention. This can enable a closed-loop sensing/drug delivery microneedle paradigm that is well-positioned to precisely deliver multiple therapeutic agents in an on-demand basis. This type of autonomous "Sense-Act-Treat" system, devices, and methods can provide an avenue for responding to biomarker fluctuations with a targeted therapy, as well as provide self-regulating drug delivery that can adjust patient dosage based on the severity of the injury or the disease process. The development of such responsive multiplexed drug-delivering systems can be implemented to transform outpatient, home-based civilian medical treatments as well as military medical care.

In another embodiment of the disclosed technology, a minimally-invasive multi-component microneedle device with carbon paste electrodes within a hollow microneedle array for electrochemical monitoring and biosensing, which can be fabricated using a digital micromirror device-based stereolithography techniques, is described. This embodiment can comprise the same embodiment(s) like those previously described, and can therefore implement the entirety of functionalities of the individual embodiments on a single embodiment. In this embodiment, a rapid prototyping method to fabricate exemplary microneedle biosensor-actuator devices is described that uses a dynamic mask (e.g., such as a Digital Micromirror Device (DMD)). In some examples, the exemplary method can employ the dynamic mask for selective polymerization of a photosensitive acrylate-based polymer resin into an exemplary microneedle sensor-actuator device. Exemplary implementations were performed that demonstrated that the hollow microneedles remained intact after puncturing the outermost layer of skin in a living organism. For example, in these exemplary implementations, the carbon fibers underwent chemical modification in order to enable detection of hydrogen peroxide and ascorbic acid; electrochemical measurements were demonstrated using integrated electrode-hollow microneedle devices. The disclosed technology includes an approach for implementing real-time, minimally invasive point-of-care sensing using an exemplary device capable of obtaining biological samples (e.g., interstitial fluid) through the skin while protecting the sensing transducer from biofouling elements. Such devices can be used as in vivo sensors to provide real-time detection of physiological processes, such as monitoring of a neurotransmitters, medically-relevant molecules, cancer biomarkers, and pathogenic microorganisms.

Exemplary materials to fabricate and implement the disclosed embodiment of the technology are presented. For example, a variety of materials can be used for microneedle fabrication, including silicon, glass, metal (e.g., stainless steel and nickel), and resorbable polymers (e.g., polyglycolic acid and polylactic acid). In one example, an acrylate-based polymer, e.g., e-Shell 200, was utilized for microneedle fabrication. The material is a Class-IIa biocompatible, water-resistant material; it has been used in thin-walled hearing aid shells, solid microneedle arrays, as well as nonmedical applications. e-Shell 200 contains 0.5-1.5% wt phenylbis(2,4,6 trimethylbenzoyl)-phosphine oxide photoinitiator, 15-30% wt propylated 2) neopentyl glycoldiacrylate, and 60-80% wt urethane dimethacrylate. Energy-dispersive X-ray spectroscopy indicated that e-Shell 200 contains carbon, oxygen, and titanium; these elements are known to possess excellent biocompatibility. e-Shell 200 exhibits a water absorption value of 0.12% (D570-98 test method) and a glass transition temperature of 109° C. (E1545-00 test method). It exhibits tensile strength of 57.8 MPa (D638M test method), flexural strength of 103 MPa (D790M test method), and elongation at yield of 3.2% (D638M test method).

For example, a method of fabrication included use of a Digital Micromirror Device-stereolithography instrument to fabricate hollow microneedles and the integration of carbon fiber electrodes within the bores of these hollow microneedles. The carbon fibers can be chemically modified to enable detection of two medically significant molecules, hydrogen peroxide and ascorbic acid. Electrochemical characterization was performed on the chemically modified electrode-hollow microneedle devices. For example, hydrogen peroxide ($H_2O_2$) is a reactive oxygen species that is monitored in many common enzyme-based electrochemical sensors. For example, $H_2O_2$ and gluconolacone are produced in reactions between glucose and glucose oxidase; monitoring of released hydrogen peroxide is used for quantification of glucose. For example, monitoring of released hydrogen peroxide may also be used for quantification of glutamate in brain dialysate; hydrogen peroxide is produced in reactions between glutamate and glutamate oxidase. Glutamate is an excitatory neurotransmitter, e.g., which has been linked with aggressive activity. Ascorbic acid can be an indicator of oxidative stress that is experienced by cells.

The following processes were implemented to demonstrate the disclosed embodiment of a microneedle array device and fabrication methods thereof Exemplary implementations included proliferation of human dermal fibroblasts and neonatal human epidermal keratinocytes on e-Shell 200 surfaces, which was evaluated using the MTT (3-(4,5-dimethylthiazol-2-yl)2,5-diphenyl tetrazolium bromide) assay, e.g., which involves reduction of a yellow tetrazolium salt to a purple formazan dye by mitochondrial succinic dehydrogenase. In the described exemplary implementations, e-Shell 200 wafers (diameter=15 mm, thickness=2 mm) were compared against glass cover slips (diameter=15 mm). The cover slips and e-Shell 200 wafers were rinsed and sterilized in two 30 minute rinses of 70% ethanol; the materials were subsequently rinsed in sterile deionized water. The e-Shell 200 wafers were placed in sterile Petri dishes in a laminar flow cabinet and sterilized with ultraviolet B light, e.g., both surfaces were exposed to ultraviolet B light. The materials were rotated 90 degrees after a minimum of two hours light exposure. Polymers were transferred to sterile 24-well culture plates, rinsed twice in sterile Hank's Balanced Salt solution, and once in the appropriate cell culture medium. The e-Shell 200 wafers were placed in 2 mL of the appropriate cell culture medium and held in the incubator until seeded.

Cryopreserved neonatal human epidermal keratinocytes (HEK) and human dermal fibroblasts (HDF) were obtained, and fibroblast growth media (FGM-2) and keratinocyte growth media (KGM-2) were also obtained (e.g., Lonza, Walkersville, Md.). The human dermal fibroblasts and neonatal human epidermal keratinocytes were propagated in 75 $cm^2$ flasks, e.g., grown to 75% confluency, and subsequently harvested. The cells were seeded (e.g., concentration=40,000 cells per well) in a 24-well plate on e-Shell wafers 200 (n=4), glass cover slips (n=4), and polystyrene well plates (n=4). Material rinsing and all media changes were performed by moving the test materials from one solution to the other using a forceps. The materials were placed in fresh medium after 48 hours; this time point corresponded with 80% confluency for human dermal fibroblasts and neonatal human epidermal keratinocytes. MTT viability was assessed 24 hours later. The materials with cells were rinsed using Hank's Balanced Salt solution; desorption using isopropyl alcohol and agitation were subsequently performed. Isopropyl alcohol (e.g., quantity=100 μL) was transferred to a new 96-well plate. Absorbance was determined (e.g., $\lambda$=550 nm) with a Multiskan RC plate reader (Labsystems Inc., Franklin, Mass.). The mean values for percent viability were calculated. Significant differences (p<0.05) were determined using the PROC GLM Procedure (SAS 9.1 for Windows) (SAS Institute, Cary, N.C.). When significant differences were found, then multiple comparisons were performed using Tukey's Studentized Range HSD (Honestly Significant Difference) test at p<0.05 level of significance.

Arrays of hollow microneedles were fabricated from three-dimensional drawings that were created using Solidworks (Dassualt Systemes S.A., Velizy, France). Support structures were fabricated from three-dimensional drawings that were created using Magics RP 13 (Materialise NV, Leuven, Belgium). In the tetrahedron-shaped microneedle design, two faces of the microneedle exhibit a vertical orientation with respect to the substrate. The microneedle input dimensions included a triangular base with 1.2 mm sides, a height of 1.5 mm, and a vertical cylindrical channel (diameter=400 μm). The needles were arranged into a 2×2 square array with 2 mm inter-microneedle spacing. The substrate input dimensions included lateral dimensions of 1 cm×1 cm and a thickness of 500 μm. Rapid prototyping of the microneedle array was performed using a Perfactory III SXGA+instrument (EnvisionTEC GmbH, Gladbeck, Germany). A 150-W halogen bulb was used as the light source for polymerization of liquid e-Shell 200 resin. Selective polymerization of the resin in the X-Y plane was achieved using Digital Micromirror Device (DMD) optics (Texas instruments, Dallas, Tex.), specifically a DMD SXGA+ guidance chip with 1280×1024-pixel resolution. This instrument contains a build envelope of 90 mm×67.5 mm. After fabrication, the microneedle array was washed in isopropanol in order to remove unpolymerized material. Post-building curing was accomplished using an Otoflash Post Curing System instrument (EnvisionTEC GmbH, Gladbeck, Germany), which contains two photo-flash lamps and provides light exposure over a wavelength range of 300-700 nm.

A Hitachi S-3200 (Hitachi, Tokyo, Japan) variable pressure scanning electron microscope with a Robinson back-scattered electron detector was used for imaging the exemplary microneedle arrays. The exemplary microneedle arrays were coated with 60% gold-40% palladium using a Technics Hummer II instrument (Anatech, Battle Creek, Mich.) prior to imaging. Skin penetration testing was performed with full-thickness cadaveric porcine skin since human skin and porcine skin exhibit similar structures. Trypan blue (Mediatech, Inc., Manassas, Va.), a toluidine-based dye, was used to assess the transdermal drug delivery functionality of the hollow microneedle arrays. Cadaveric full-thickness weanling Yorkshire/Landrace skin was stored at 3° C. until testing was performed. Hollow microneedle arrays were inserted into full-thickness porcine skin. After removal of the arrays, Trypan blue was applied to the insertion site; the site was subsequently washed with isopropanol swabs. The Trypan blue-treated skin was subsequently imaged using optical microscopy. Images of a microneedle device before insertion into porcine skin and after insertion into porcine skin were obtained using optical microscopy.

FIGS. 18A-18D show illustrative schematics showing processing steps for assembly of an exemplary microneedle array device of the disclosed embodiment. In this embodiment, the disclosed microneedle array device includes two layers. An upper layer includes the microneedle array, and the lower layer provides support for the carbon fibers and facilitates alignment of the carbon fibers to the microneedle array. For example, the support component can be fabricated from a 1.6 mm thick poly-(methylmethacrylate) (PMMA) piece. An array of holes can be laser drilled through the PMMA piece using a Model PLS instrument, including a 6.75 60-watt $CO_2$ laser and a computer-controlled XY stage (Universal Laser Systems, Scottsdale, Ariz.), as shown in FIG. 18A. The holes can be placed in a square pattern with 2 mm spacing. For example, using a Model HPDFO high power density focusing optics lens (Universal Laser Systems, Scottsdale, Ariz.), the diameter of the exemplary hole at the exit surface was measured at ~45 µm. For example, to control the carbon fiber length beyond the support surface, the support component was placed on top (exit-side down) of a well with a depth of 100 µm. The carbon fiber can be inserted into each of the holes (entrance-side) and allowed to rest at the bottom of the well, as shown in FIG. 18B. The fibers can be secured in place with acrylic adhesive on the entrance side after a desired well depth has been achieved, as shown in FIG. 18C. FIGS. 19A and 19B show optical images of an array of carbon fiber electrodes and a single carbon fiber electrode in focus, respectively. The support layer and microneedle layer can be brought together in such a manner that the carbon fibers are positioned within the hollow shafts of the microneedles. The layers can be subsequently adhered to each other. For example, metallic epoxy can be applied to the back of the fibers in order to create the connection for the working electrode, as shown in FIG. 18D.

The exemplary implementations included 7 µm carbon fibers (Alfa Aesar, St. Louis, Mo.) that were activated in a KOH solution (concentration=0.1 M) at a pH of 13 and at a potential of 1.3 V for five minutes. In situ diazotation of 2-amino-4-nitrophenol was performed by mixing a solution of 8 mM sodium nitrite and 6 mM 2-amino-4-nitrophenol on ice for 5 minutes to create the corresponding diazonium salt. After five minutes, the activated carbon fibers were inserted. Two cyclic voltammetry (CV) scans were run from 0.4 V to −0.8 V at 0.1 V/s to enable electrochemical grafting of the 2-nitrophenol and subsequent reduction to the aminophenol. The carbon fibers were modified with palladium to enable detection of hydrogen peroxide. Activated carbon fiber bundles were placed in a solution of 1 mM palladium (II) chloride; Pd was deposited by applying a potential of −0.8 V for 120 s. The electrochemical measurements were obtained using a PGSTAT12 Autolab electrochemical instrument (EcoChemie, Utrecht, the Netherlands). Data was acquired versus an Ag/AgCl reference and a Pt counter electrode.

Figure 20A:
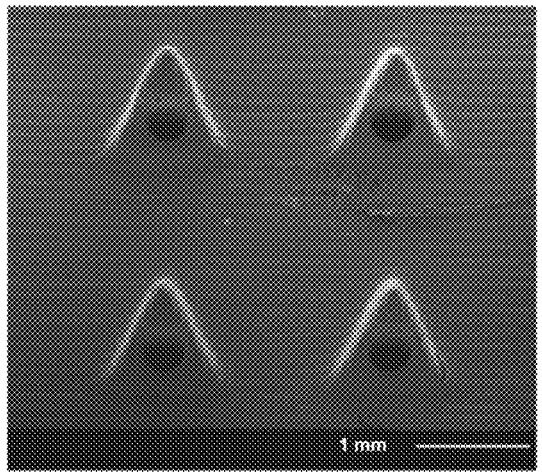
FIGS. 20A and 20B show SEM images of an exemplary hollow microneedle array.
Figure 20B:
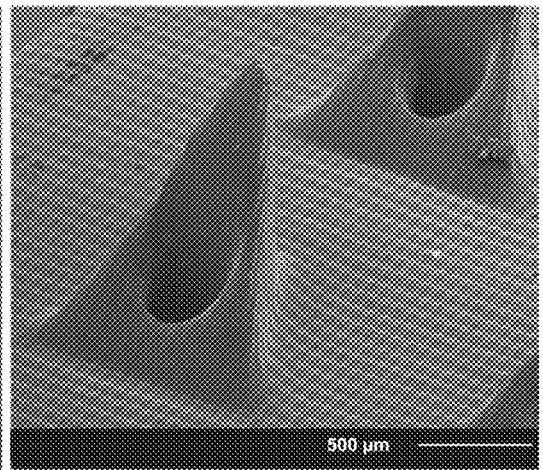

The Digital Micromirror Device-based stereolithography instrument was employed for the fabrication of approximately 200 arrays over a three-hour period. FIGS. 20A and 20B show SEM images of an exemplary hollow microneedle array and an exemplary single hollow microneedle of the disclosed embodiment prior to incorporation of carbon fiber electrodes, respectively. Measurements obtained from the SEM images showed that the exemplary microneedles exhibited heights of ~1030 µm, triangular bases with side lengths of ~1120 µm, and bore diameters of ~375 µm. Good microneedle-to-microneedle uniformity was noted among the microneedles in the microneedle array. In this exemplary implementation, it is noted that differences between input and measured dimensions may be attributed to translation of the computer-aided design drawing by the software. For example, Digital Micromirror Device-based stereolithography and other rapid prototyping techniques involve tessellation, conversion of the surface of the computer-aided design drawing into a series of polygons. This polygon series is converted into a series of cross-sectional layers, which is subsequently used for layer-by-layer fabrication of the microneedle device. It is not possible to predict how the computer-aided design drawing is manipulated by the software.

Figure 21A:
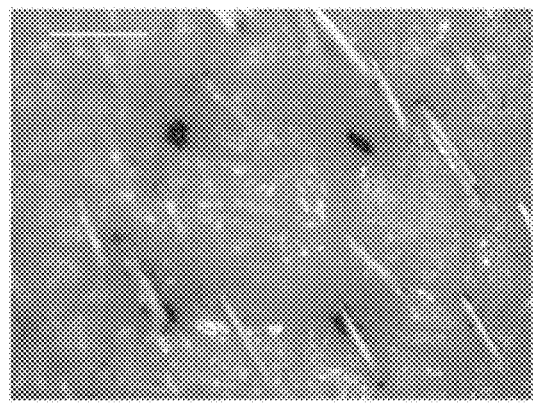
FIG. 21A shows an image of skin after application of an exemplary microneedle array.
Figure 21B:
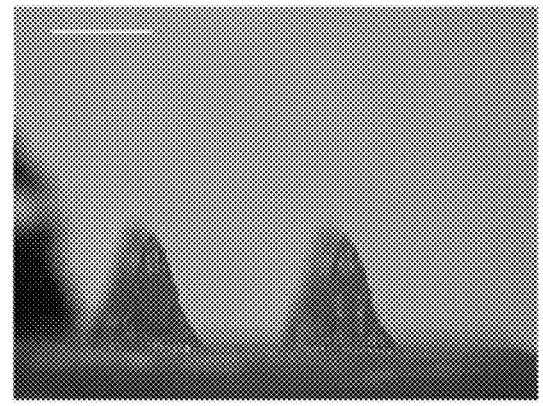
FIG. 21B and FIG. 21C show optical micrographs of hollow microneedles before and after insertion into skin.
Figure 21C:
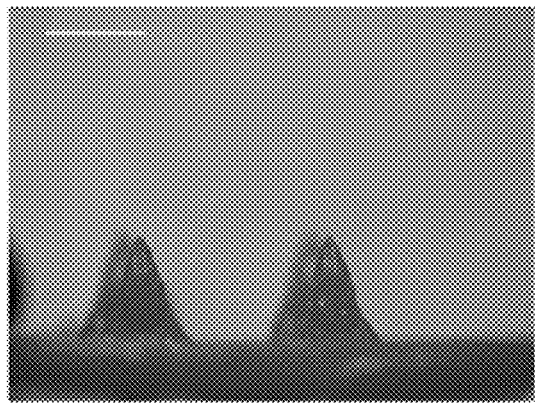

For example, microneedles undergo bending forces, compressive forces, shear forces, and skin resistance during skin insertion; the pressure necessary for human skin penetration can exceed $3.0 \times 10^6$ Pa. The skin penetration properties of the microneedle devices were evaluated using cadaveric porcine skin, which has been previously used as a model for assessing microneedle functionality. FIG. 21A shows an image of porcine skin after application of the microneedle array, removal of the microneedle array, and application of Trypan blue. The Trypan blue spots indicate penetration through the stratum corneum layer (outermost layer) of the epidermis by the microneedle array and localization of Trypan Blue within microneedle-generated pores. FIG. 21B and FIG. 21C show optical micrographs of hollow microneedles before insertion into porcine skin and after insertion into porcine skin, respectively. These exemplary images indicate that the microneedles remain intact after skin insertion.

Figure 22A:
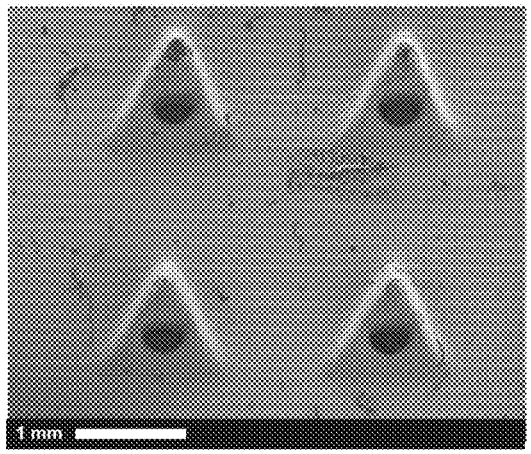
FIGS. 22A and 22B show SEM images of an exemplary hollow microneedle array.
Figure 22B:
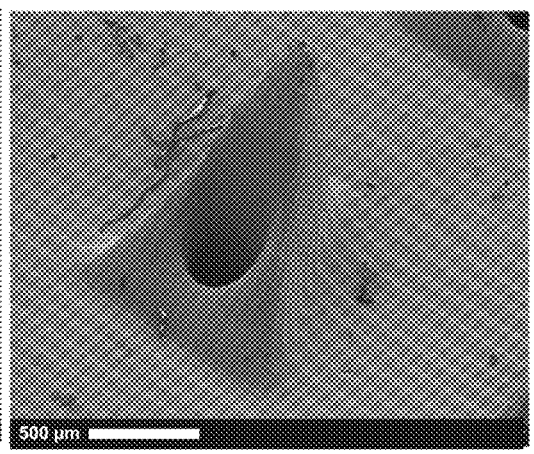

For example, the positioning of the exemplary carbon fiber electrodes within the microneedle device can facilitate interactions with the biological sample and minimize carbon fiber exposure to stresses associated with microneedle insertion into skin and movement at the microneedle device-skin interface. To facilitate interactions between the biological sample and the carbon fiber electrodes, the carbon fiber electrodes can be positioned at the centers of the microneedle bores. In addition, dead space between the carbon fiber electrodes and the microneedle sidewalls may allow for infiltration of the biological sample. FIG. 22A shows an SEM image of a hollow microneedle array, and FIG. 22B shows an SEM image of a single hollow microneedle after incorporation of carbon fiber electrodes. The exemplary SEM image of FIG. 22B reveals that the carbon fiber electrodes do not extend beyond the tip of the microneedle bore. Placement of carbon fibers within the microneedle bores included precise alignment of the microneedle bores and the carbon fibers, e.g., the positions of the laser-ablated holes in the lower layer of the microneedle device were coordinated with the positions of the microneedle bores in the upper layer of the microneedle device.

Figure 23:
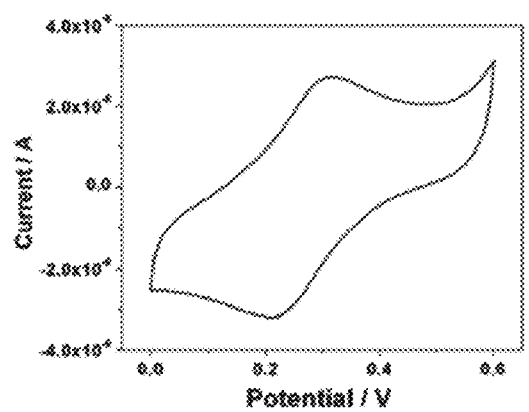
FIG. 23 shows a data plot of a cyclic voltammetric scan of ferricyanide in KCl versus Ag/AgCl reference and Pt counter electrodes.

The exemplary implementation included the evaluation of the electrochemical response of the exemplary carbon fibers within the electrode-hollow microneedle device towards 5 mM $Fe(CN)_6^{3-/4-}$/1 M KCl. FIG. 23 shows a data plot of a cyclic voltammetric scan of 5 mM ferricyanide in 1 M KCl versus Ag/AgCl and Pt reference counter electrodes, respectively, e.g., at a scan rate of 100 mV/s. For example, well defined oxidation/reduction waves were observed, indicating interaction between the carbon fiber electrodes and the test solution as a result of permeation of the microneedle bore by the test solution. The average formal potential ($E^{o'}$) for $Fe(CN)_6^{3-/4-}$ was measured at 220 mV vs. Ag/AgCl reference and platinum counter electrodes, respectively. The average peak separation was $\Delta E_p = 125$ mV. These exemplary results indicate that the carbon fibers within the electrode-hollow microneedle device were capable of providing electrochemical measurements.

Figure 24:
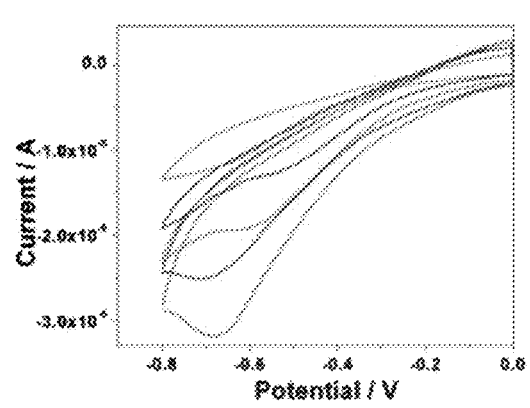
FIG. 24 shows a data plot of cyclic voltammetric scans of hydrogen peroxide versus Ag/AgCl reference and Pt counter electrodes.

The exemplary implementation included the evaluation of palladium-catalyzed oxidation of hydrogen peroxide on the carbon fibers within the exemplary electrode-hollow microneedle devices. For example, palladium was deposited onto the carbon fibers by applying a potential of −0.8V for 120 sec in 1 mM Pd/0.5M HCl prior to insertion into the microneedle device. FIG. 24 shows a data plot of cyclic voltammetric scans of 0, 50, 100, 300, and 500 μM hydrogen peroxide, e.g., as shown represented by pink, black, green, blue, and red curves, respectively, versus Ag/AgCl and Pt reference counter electrodes, respectively, at a scan rate of 100 mV/s. This exemplary data shown in FIG. 24 shows an increase in reductive currents after additions of 0, 50, 100, 300, and 500 μM hydrogen peroxide, exhibiting a linear range of 100-500 μM and a detection limit of ~15 μM (based on the response of 50 μM hydrogen peroxide; S/N=3).

Figure 25:
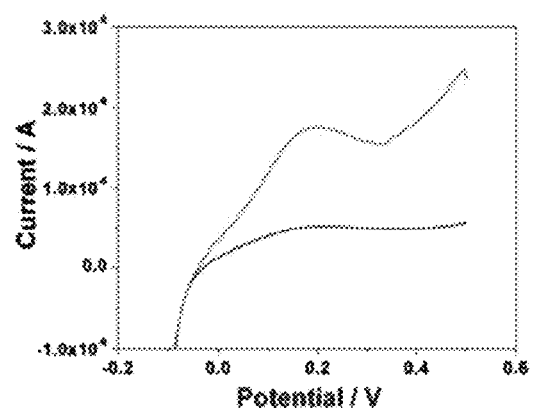
FIG. 25 shows a data plot of voltammetric scans of buffer solution and ascorbic acid in buffer versus Ag/AgCl reference and Pt counter electrodes.

For example, the carbon fibers were modified with aminophenol (o-AP) groups following in-situ diazotination and electrografting of the corresponding diazonium salt. Modification of the carbon fiber electrode with o-AP can result in electrocatalytic oxidation of ascorbic acid and selective oxidation of ascorbic acid in the presence of common interferents, e.g., such as uric and citric acid. Uric acid is a well-known interferent in electrochemical analysis of ascorbic acid, e.g., which can be attributed to the fact that uric acid and ascorbic acid possess similar oxidation potential values. Linear sweep voltammograms of 100 mM phosphate buffer (blank solution) and 1 mM ascorbic acid in 100 mM phosphate buffer (pH=7) versus Ag/AgCl and Pt reference counter electrodes, respectively, at a scan rate of 100 mV/s are shown in FIG. 25. This exemplary result indicates that the carbon fibers within the electrode-hollow microneedle device are able to detect the ascorbate analyte with the low potential oxidation of ascorbic acid at 195 mV. Electrochemical measurements by the carbon fibers within the electrode-hollow microneedle device of the disclosed embodiment were demonstrated. In addition, chemical modification of the exemplary carbon fibers for selective analytes was shown, and detection of hydrogen peroxide and ascorbic acid using these modified carbon fibers was demonstrated.

In another embodiment of the disclosed technology, a minimally-invasive multi-component microneedle device with carbon paste electrodes (CPEs) for electrochemical monitoring and biosensing is described. This embodiment can comprise the same embodiment(s) like those previously described, and can therefore implement the entirety of functionalities of the individual embodiments on a single embodiment. The exemplary carbon paste electrodes can exhibit a renewable nature or functionality that enables the packing of the exemplary hollow non-planar microneedles with pastes that contain assorted catalysts and biocatalysts. For example, smoothing the surface can result in microelectrode-to-microelectrode uniformity. Optical and scanning electron micrographs show the surface morphology at the microneedle apertures. Exemplary implementations of the disclosed microneedle electrode arrays included low-potential detection of hydrogen peroxide at rhodium-dispersed carbon paste microneedles in vitro and lactate biosensing by the inclusion of lactate oxidase in the metallized carbon paste matrix. The exemplary implementations demonstrated highly repeatable sensing, e.g., for following consecutive cycles of packing/unpacking the carbon paste. For example, the operational stability of the exemplary array was demonstrated, as well as the interference-free detection of lactate in the presence of physiologically relevant levels of ascorbic acid, uric acid, and acetaminophen. The described microneedle design can be well-suited for diverse biosensing applications, e.g., including subcutaneous electrochemical monitoring of a number of physiologically-relevant analytes.

For example, carbon paste can be characterized by a high degree of moldability that is essential for optimal packing and can be employed in electroanalysis. CPEs can include the advantages of low background current, low cost, as well as convenient surface renewal and modification (e.g., via the inclusion of the modifiers within the paste). Exemplary microneedle arrays of the disclosed embodiment can include a nine-element arrays of pyramidal-shaped hollow microneedles, which possess a 425 μm-diameter aperture through which the modified carbon paste is extruded and can act as a transducer. For example, rhodium-dispersed carbon paste, which can be used for low-potential detection of hydrogen peroxide, can be packed within the microneedles to minimize the contribution of co-existing electroactive interferents. The described microneedle array CPE sensor device obviates the need for integrated microchannels and extraction of the interstitial fluid.

Exemplary materials and methods to implement the disclosed embodiment of the technology are presented. The following chemicals and reagents were used in the described implementations, which included lactate oxidase from *Pediococcus* sp. (LOx, E. C. 1.13.12.4), rhodium on carbon (5% Rh weight), polyethyleneimine (PEI), mineral oil (e.g., d=0.838 g/mL), L-lactic acid, hydrogen peroxide ($H_2O_2$), L-ascorbic acid (AA), uric acid (UA), acetaminophen (AC), ethyl alcohol, potassium phosphate monobasic, and potassium phosphate dibasic were obtained from Sigma Aldrich (St. Louis, Mo.) and were used without further purification or modification. All experiments were performed with 0.1 M phosphate buffer (pH 7.0). Ultrapure water (e.g., 18.2 MΩ·cm) was employed in the exemplary implementations.

The exemplary solid and hollow microneedle arrays used in the exemplary implementations were developed in the following manner. The hollow microneedle arrays were fabricated with the aid of Solidworks (Dassualt Systemes S.A., Velizy, France) computer models. Substrate structures were designed with Magics RP 13 (Materialise NV, Leuven, Belgium). For example, the needles were pyramidal in shape with a triangular base. For example, the dimensions of each microneedle were as follows: an edge length of 1250 μm, a height of 1500 μm, and a vertical cylindrical bore of 425 μm in diameter on one of the faces of the pyramid structure. The exemplary needles were arranged into 3×3 square arrays with 2 mm periodicity. Substrates for the microneedle arrays were 10 mm×10 mm in extent and possessed a thickness of 500 μm. The three-dimensional computer models were transferred to a Perfactory® SXGA Standard UV rapid prototyping system (EnvisionTEC GmbH, Gladbeck, Germany) for production. This system uses these computer models to precisely guide light from a 150 W halogen bulb over a photocurable material, resulting in the selective polymerization of the exposed material. Eshell 200 acrylate-based polymer (EnvisionTEC GmbH, Gladbeck, Germany) was utilized as the constituent material to fabricate the microneedle arrays since the resin selectively polymerizes under visible light and exhibits a Young's modulus of elasticity of 3050±90 MPa. The polymer also offers Class-IIa biocompatibility per ISO 10993. A 550 mW output power beam (e.g., step size=50 μm) with a zero-degree tilt was employed for the polymerization of the resin. Following fabrication, the arrays were rinsed with isopropanol for removal of the unpolymerized material and subsequently placed in an Otoflash post curing system (EnvisionTEC GmbH, Gladbeck, Germany) for post-build curing.

The exemplary enzyme-functionalized rhodium-dispersed carbon paste microelectrode array was prepared in the following manner. For example, 100 mg of Rh-on-carbon and 10 mg of LOx were thoroughly homogenized via 10 alternating 5-min cycles of vortexing and ultrasonication. The mixture was then vortexed for an additional 1 hr. Following the homogenization process, 125 mg of the mineral oil pasting liquid and 15 mg of the PEI enzyme stabilizer were added to the solid mixture. Homogenization of the resulting paste mixture was accomplished by grinding the mixture with a mortar and pestle for an additional 1 hr.

For example, a 3 mL syringe (BD Biosciences, Franklin Lakes, N.J.) can be utilized as the support to extrude the metallized carbon paste through the microneedle array. The nozzle portion of the syringe was removed to facilitate the attachment of the microneedle array, which was affixed (e.g., using adhesive epoxy) to this cleaved end for durability. A copper wire was subsequently inserted into the back end of the syringe barrel in order to create an electrical contact to the microneedle transducer. Following this exemplary procedure, the carbon paste mixture was loaded into the syringe from the back end and then extruded with a plunger until the paste began to expel through the microneedle microholes. Excess paste was removed from the openings; the surface was later smoothed using wax paper. In order to investigate the repeatability of the response after repacking the microneedles with new paste, the array was carefully removed from the syringe and subsequently immersed in ethanol under ultrasonication in order to remove the extraneous carbon paste residue. A 0.15 mm diameter iridium wire was used to facilitate removal of the paste from the microhole. The aforementioned assembly and packing protocols were then followed in order to generate a new electrode from the cleaned microneedle array.

The instrumentation used in the described implementations included the following, which was utilized in exemplary demonstrations and implementations of the disclosed embodiment under exemplary conditions disclosed herein. A CH Instruments (Austin, Tex.) model 1232A electrochemical analyzer was employed for electrochemical measurements. An external Ag/AgCl reference electrode (CH Instruments CHI111) and a 0.5 mm diameter platinum wire counter electrode were used to establish a three-electrode electrochemical system. The electrochemical experiments were performed in a 7 mL cell at room temperature (22° C.). Voltammetric and chronoamperometric studies were used to evaluate the electrochemical behavior of the exemplary carbon paste microneedle array electrode. In these electrochemical implementations, either $H_2O_2$ or lactate was added into 5 mL of potassium phosphate buffer solution in order to obtain the desired concentration. Chronoamperometric currents were sampled at 15 s following the potential step. In order to obtain hydrodynamic voltammograms, fixed potential amperograms were recorded in a stirred phosphate buffer solution containing the desired $H_2O_2$ concentration by varying the potential between −0.20 and +0.60 V vs. Ag/AgCl (e.g., in 0.05V increments). The solution was continuously stirred using a magnetic stirrer at a rate of 100 rpm. The morphology of the carbon paste microneedle array was examined using a field emission scanning electron microscope (Philips XL30, Amsterdam, The Netherlands). All of the specimens were coated with chromium prior to analysis using a sputtering instrument (Energy Beam Sciences Emitech K575X, East Granby, Conn.). A deposition current of 130 mA was applied for 30 s to deposit ~15 nm of chromium on the sample surface.

Figure 26A:
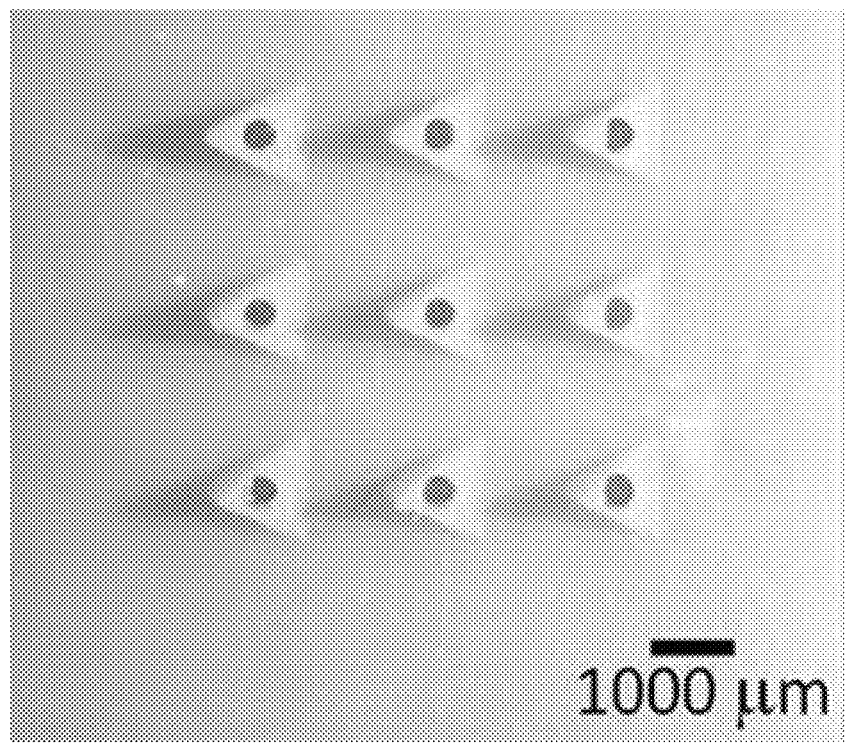
FIGS. 26A and 26B show optical micrographs of the unpacked and Rh-carbon paste packed microneedle array.
Figure 26B:
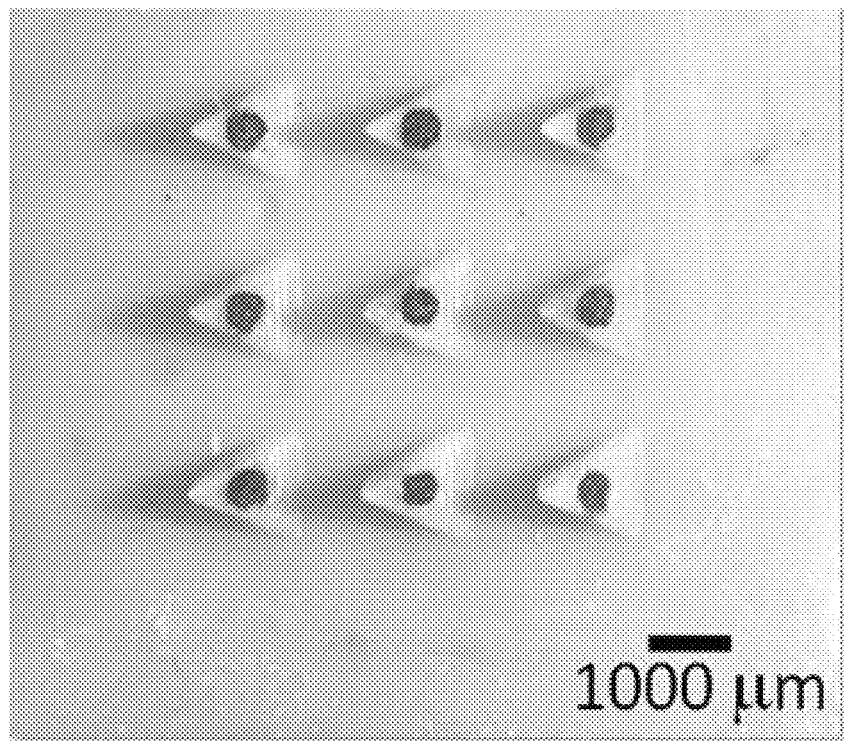

Exemplary implementations of the disclosed embodiment included characterization of the surface morphology of the carbon paste microelectrode array. For example, unmodified and modified carbon pastes can readily conform with the non-planar features of microneedle array devices. Initial implementations were aimed at characterizing the morphology of the carbon paste-loaded microneedle array and were initiated with a close examination of the microelectrode surface. FIGS. 26A and 26B show optical micrographs of the unpacked and Rh-carbon paste packed microneedle array, respectively. An optical micrograph of the exemplary unpacked microneedle array is shown in FIG. 26A. This image shows uniform pyramidal microneedle structures (with triangular bases) possessing a height of 1500 μm as well as the cylindrical openings (425 μm diameter). FIG. 26B depicts an exemplary microneedle array that has been packed with carbon paste and subsequently polished. It indicates that the surface has been smoothly polished to obtain a highly reproducible exposed area, thereby facilitating reliable electrochemical sensing. As shown in the figures, microelectrode-to-microelectrode uniformity can be observed.

Figure 27A:
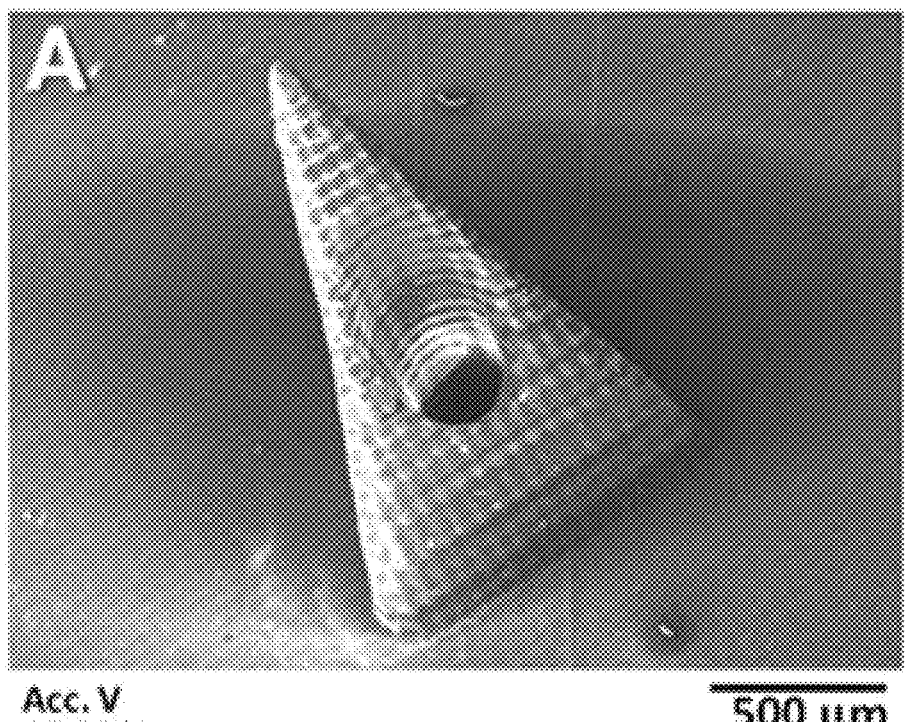
FIGS. 27A and 27B show SEM images of the unpacked and Rh-carbon paste packed microneedle constituent of the array.
Figure 27B:
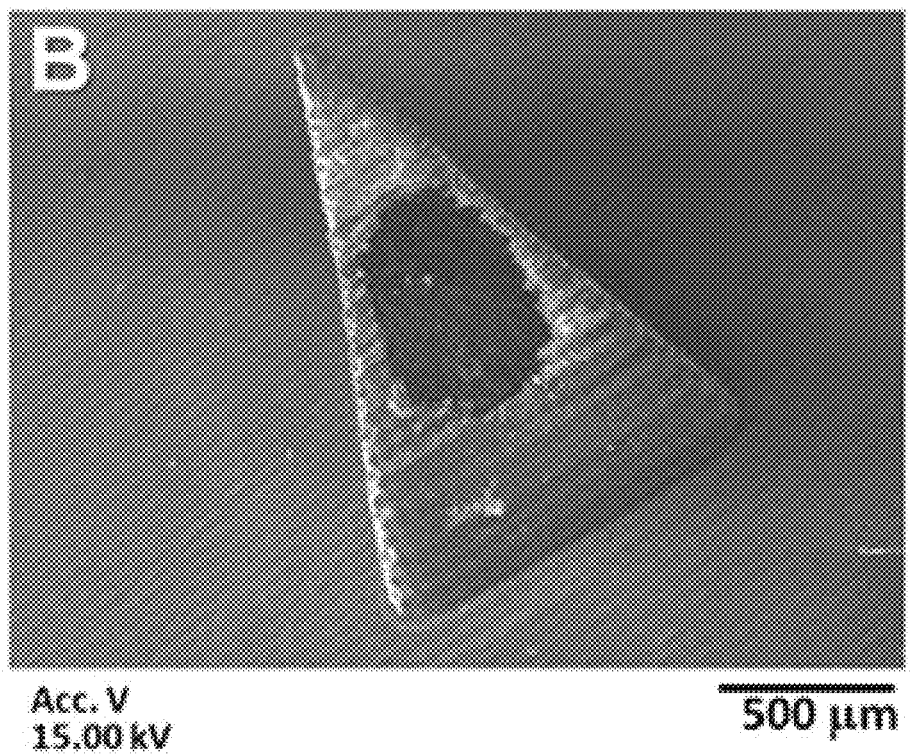

Pursuant to the characterization of the surface morphology, SEM imaging of the microneedle was performed. FIGS. 27A and 27B show SEM images of the unpacked and Rh-carbon paste packed microneedle constituent of the array. FIG. 27A shows an electron micrograph of a single microneedle. The structure of the microneedle can be observed, e.g., the bored cylindrical vacancy and the ribbed structure created by rastering of the light source over the polymer resin. FIG. 27B shows the surface details of a single microneedle packed with the carbon paste. For example, as shown in the figure, a well-formed surface, a relatively smooth morphology, and defined edges can be observed, e.g., reflecting the effective filling of the cylindrical microhole. Such surface quality can be achieved by extruding excess paste and later polishing the surface. It should be noted that the microneedle and the opening appear to be elongated due to the oblique angle at which the SEM image was acquired.

Figure 28A:
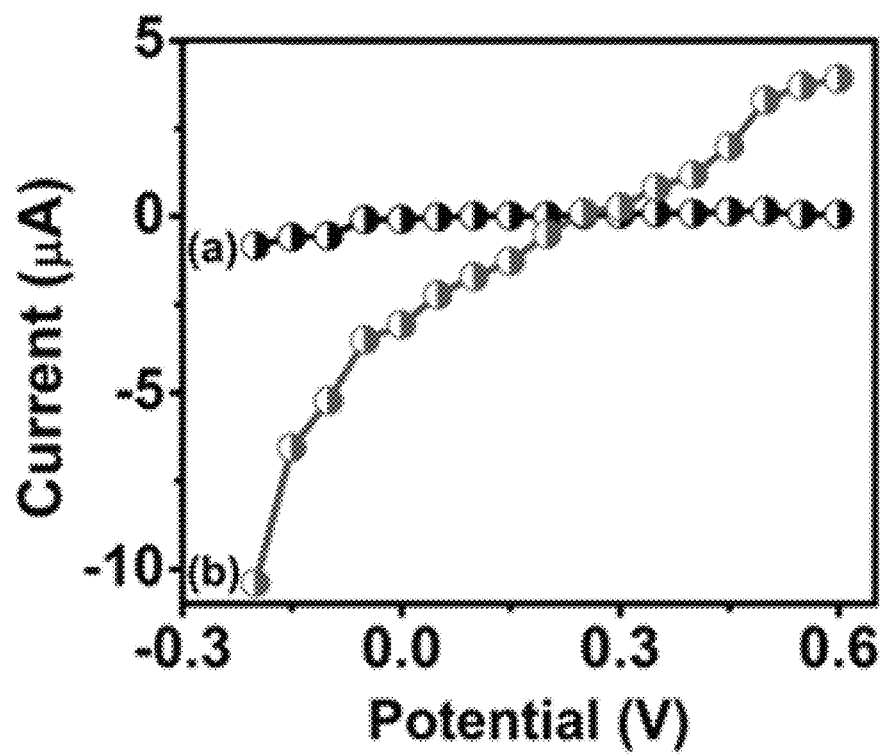
FIG. 28A shows plots of hydrodynamic voltammograms of buffer and hydrogen peroxide at the rhodium-dispersed carbon paste microneedle electrode.

Exemplary implementations of the disclosed embodiment included electrochemical characterization of the carbon paste microelectrode array towards peroxide-based amperometric sensing. For example, initial electrochemical implementations were carried out to characterize the response of the carbon paste microneedle array to $H_2O_2$. A hydrodynamic voltammogram (HDV) was recorded over the −0.20 to +0.60 V range in order to deduce a suitable operating potential and to demonstrate the strong catalytic ability of the Rh-CPE towards the redox processes of $H_2O_2$. The exemplary results, shown in FIG. 28A, elucidate that the Rh-CPE offers convenient detection of $H_2O_2$ over the entire range tested, with a crossover point occurring around 0.22V (vs. Ag/AgCl). FIG. 28A shows plots of hydrodynamic voltammograms of 0.1M potassium phosphate buffer (data plot (a)) and 10 mM $H_2O_2$ (data plot (b)) at the rhodium-dispersed carbon paste microneedle electrode. For example, such lowering of the overvoltage enables the selection of a low operating potential of −0.15V vs. Ag/AgCl for subsequent sensor implementations. At this exemplary potential, a reduction current of 5.95 μA can be achieved for 10 mM $H_2O_2$. Contributions imparted by common electroactive interferences were negligible.

Figure 28B:
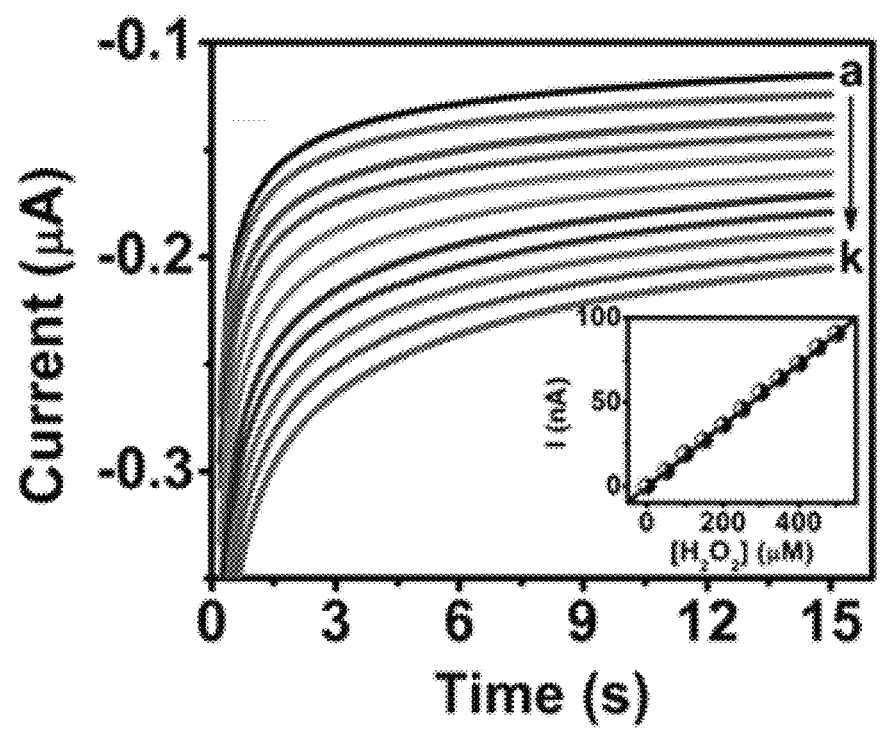
FIG. 28B shows plots of chronoamperograms obtained using the exemplary rhodium-dispersed carbon paste microneedle electrode.

The exemplary microneedle CPEs display a wide dynamic range for $H_2O_2$ detection. FIG. 28B shows plots of chronoamperograms obtained using the rhodium-dispersed carbon paste microneedle electrode (e.g., 0-500 µM $H_2O_2$ in 50 µM increments, a→k; $E_{App}$=−0.15 V vs. Ag/AgCl). An exemplary calibration curve is shown in the inset of FIG. 28B. For example, as shown in FIG. 28, well-defined currents, proportional to the $H_2O_2$ concentration, were observed. The exemplary resulting calibration curve, based on sampling the current at 15 s following the potential step, displays high linearity ($R^2$=0.999; as shown in the inset). The response for 50 µM $H_2O_2$ (curve b) indicated a limit of detection (LOD) of ~20 µM (S/N=3). The ability to detect $H_2O_2$ at low potentials is an attractive feature of the disclosed Rh-CPE microneedle array when positioned for use in minimally-invasive oxidase-based biosensors.

Figure 29:
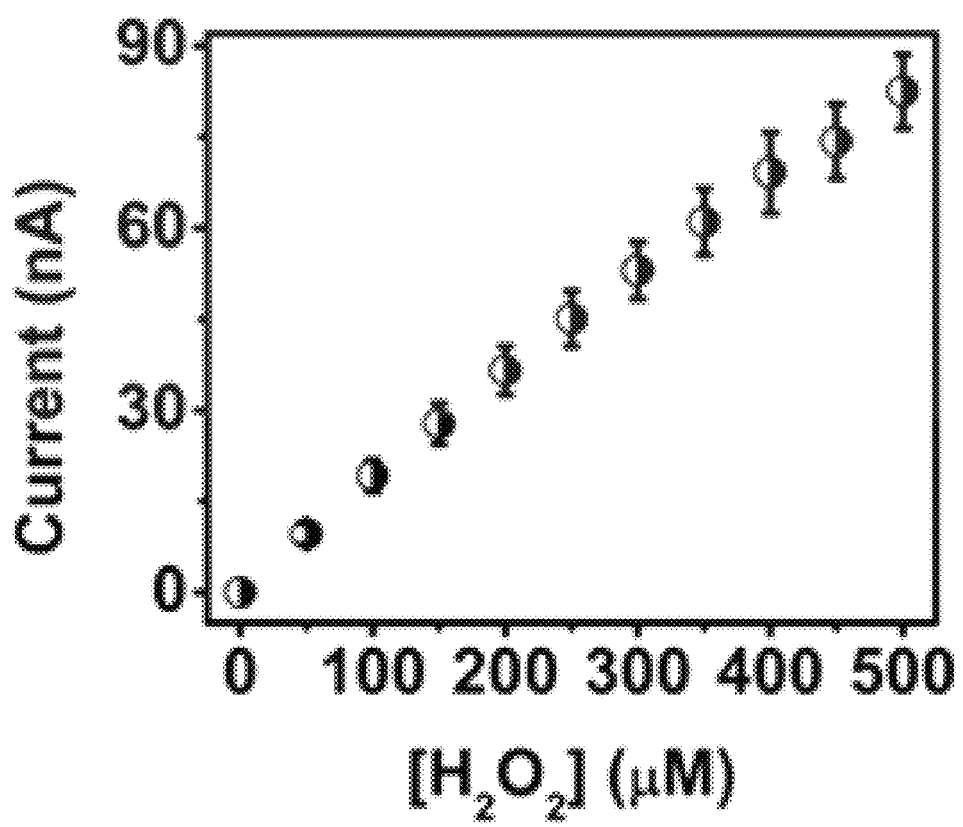
FIG. 29 shows a plot of a calibration curve obtained for hydrogen peroxide concentrations.

Exemplary implementations of the disclosed embodiment included evaluations on the effect of reconstitution of the carbon paste matrix within the microelectrode array. For example, a key advantage of carbon paste-based electrodes is their renewable surface, which can be readily regenerated. Such regeneration should facilitate the re-use of the microneedle array. Accordingly, the effect of repetitive packing of the array upon the resulting response was evaluated. As such, five calibration experiments were executed for $H_2O_2$ over the 50 to 500 µM $H_2O_2$ range, which involved successively reconstituted carbon paste surfaces. Between each experimental implementation, the electrode was thoroughly disassembled, cleaned, reassembled, and repacked; its electrochemical response was then characterized. FIG. 29 shows a plot of a calibration curve obtained for $H_2O_2$ concentrations from 0 to 500 µM in 50 µM increments (e.g., $E_{App}$=−0.15 V vs. Ag/AgCl, t=15 s). The effect of reconstitution of the Rh-dispersed carbon paste microneedle array is illustrated for five subsequent reconstitution operations. The results, illustrated in FIG. 29, are indicative of a highly-repeatable calibration. For example, the response of successive packings deviated by no more than 5.4% from the average current at each level over the examined concentration range. Highly linear results were observed over the concentration range ($R^2$=0.997), along with a very low standard deviation (e.g., σ<10 nA). These exemplary data demonstrate that repeated packing/unpacking of the carbon paste constituent in the microneedle array resulted in a reproducible electrochemical response.

Figure 30A:
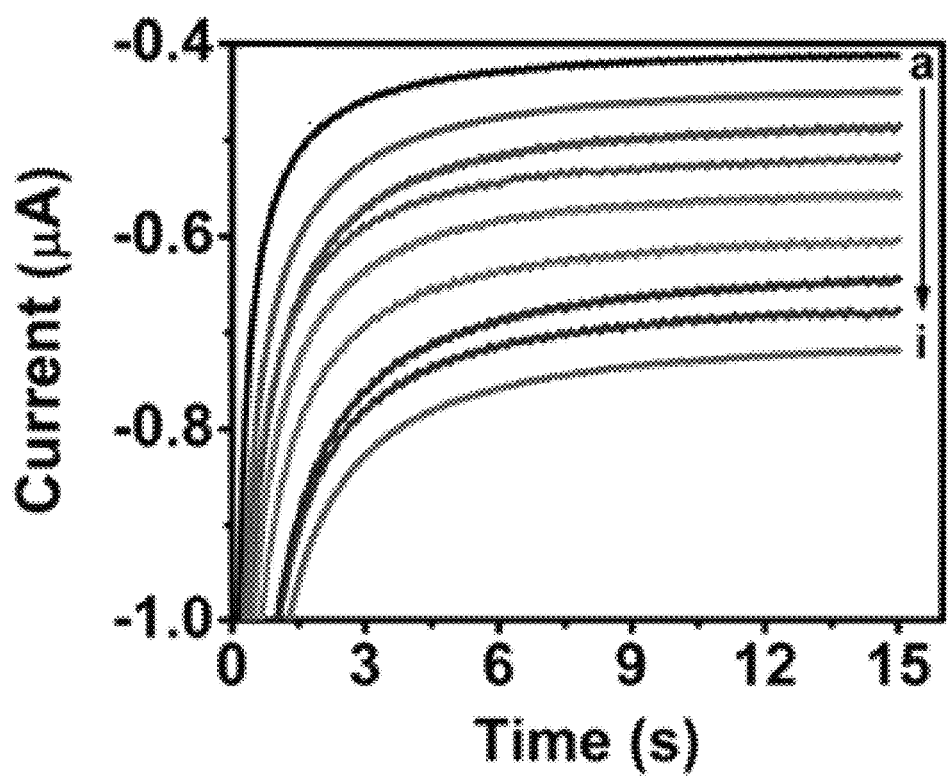
FIG. 30A shows plots of chronoamperograms obtained for lactate.
Figure 30B:
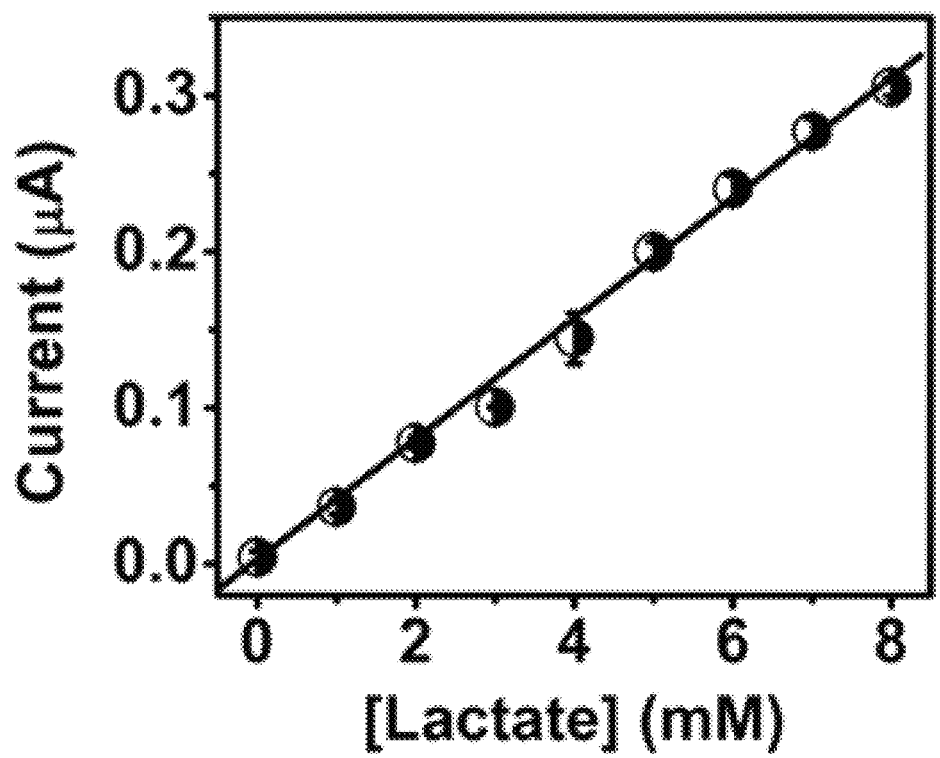
FIG. 30B shows a plot of a calibration curve obtained for lactate concentrations.

Exemplary implementations of the disclosed embodiment included the biosensing of lactate at the microneedle CPE arrays. For example, an exemplary microneedle array CPE biosensor for lactate was developed. Lactate oxidase (LOx)-dispersed metallized carbon paste was prepared using PEI for the electrostatic entrapment of the enzyme within the matrix. Chronoamperometric calibration experiments were performed using the LOx-Rh-carbon paste microneedle array at −0.15 V vs. Ag/AgCl for increasing levels of lactate (e.g., 0 to 8 mM in 1 mM increments). Typical chronoamperograms are displayed in FIG. 30A, which shows exemplary plots of chronoamperograms obtained for lactate concentrations from 0 to 8 mM in 1 mM increments (e.g., $E_{App}$=−0.15 V vs. Ag/AgCl). FIG. 30B shows an exemplary calibration curve corresponding to the chronoamperometric current at t=15 s. For example, high linearity ($R^2$=0.990) and low deviation (e.g., σ<10 nA) were observed. A detection limit was estimated to be 0.42 mM lactate (S/N=3), which is well below normal physiological levels and is therefore more than sufficient for relevant applications. It should be noted that the exemplary linear concentration range encompasses the entire physiological and pathological range of lactate in transdermal fluids, e.g., indicating the diagnostic value of the microneedle-based lactate biosensor.

Figure 31:
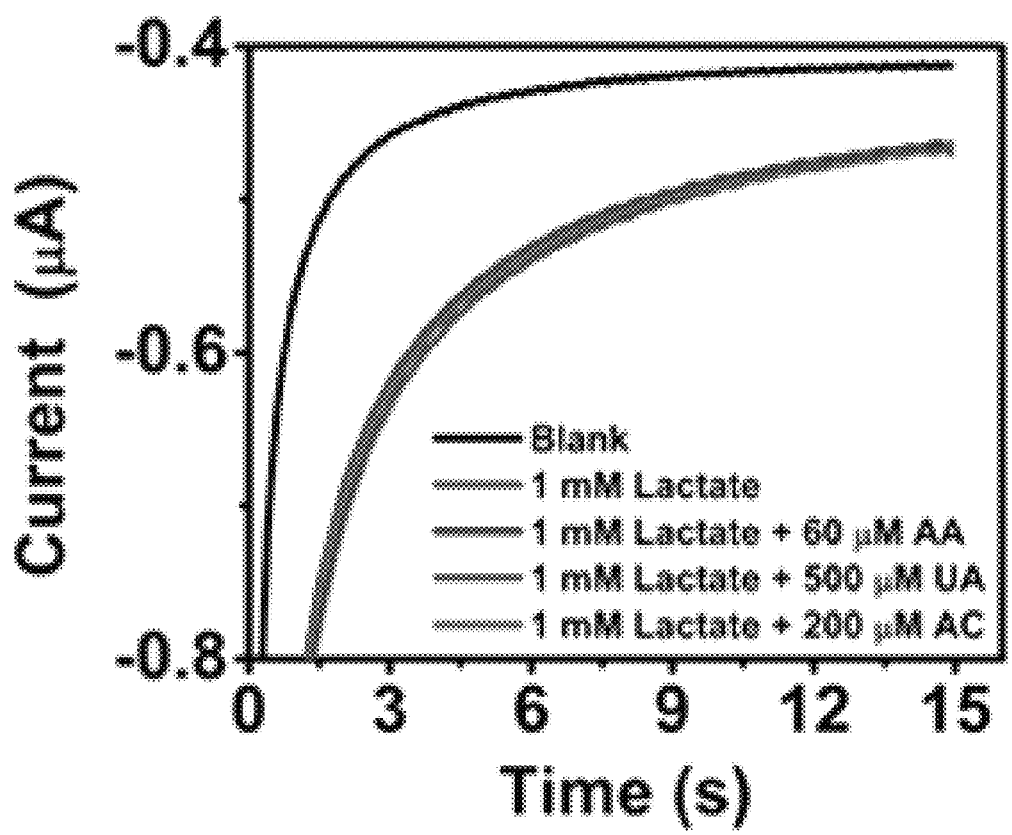
FIG. 31 shows plots of chronoamperograms showing the effect of physiologically-relevant electroactive interferents.

Exemplary implementations of the disclosed embodiment included evaluating the microneedle CPE arrays for interference by common electroactive compounds. For example, in order to ascertain that the exemplary biosensor could function as intended in the presence of common electroactive substances found in transdermal fluids, an interference investigation was conducted using physiological levels of these compounds. FIG. 31 shows plots of chronoamperograms showing the effect of physiologically-relevant electroactive interferents upon the detection of 1 mM lactate in the presence of 60 µM ascorbic acid (AA), 500 µM uric acid (UA), and 200 µM acetaminophen (AC) (e.g., $E_{App}$=−0.15 V vs. Ag/AgCl). As shown in the figure, the addition of any of these common electroactive interferents resulted in a negligible effect on the lactate response of the exemplary biosensor device. For example, a maximum current deviation of only 1.5% from the 1 mM lactate level was observed for the addition of AC. For example, such interference-free lactate detection reflects the strong and preferential electrocatalytic activity of the Rh-CPE towards $H_2O_2$, which can be detected by the described microneedle paste biosensor, e.g., for lactate monitoring in transdermal fluids.

Figure 32:
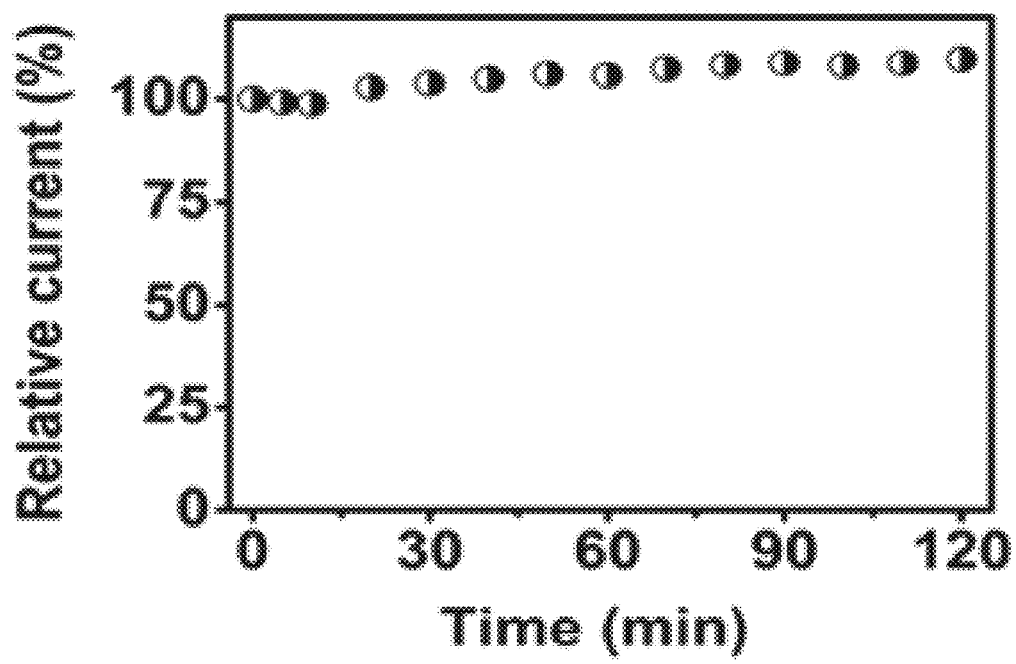
FIG. 32 shows a data plot showing the stability of the electrochemical response of an exemplary microneedle array used for lactate detection.

Exemplary implementations of the disclosed embodiment included evaluating the stability of the lactate response of the microneedle CPE arrays. For example, the stability of the microneedle array-based biosensor was examined from repetitive chronoamperograms for 2 mM lactate over a 2 hour period. In some examples, an initial short preconditioning step was implemented. This process involved the immersion of the exemplary CPE microneedle array in a 0.1 M potassium phosphate buffer (pH 7.0) and the concomitant recording of six chronoameprograms, followed by the immersion of the array in a 2 mM lactate solution for 10 min while recording two chronoamperograms. After the exemplary preconditioning, the current was sampled every 10 min over the entire 2 hour stability test period. FIG. 32 illustrates the time-course profile of the resulting current response, e.g., with the initial reading at t=0 min normalized to 100%. FIG. 32 shows a data plot of the stability of the electrochemical response of the microneedle array for 2 mM lactate ($E_{App}$=−0.15V vs. Ag/AgCl) over a 2 hour duration. As shown in the figure, a stable current was achieved almost immediately following the initialization of the experiment, with only a slight increase (of 9.7%) over the entire 2 hour time course. The stable response reflects the integrity of the exemplary CPE microneedle array biosensor. For example, tight packing of the CPE, which can prevent the potential accumulation of the enzymatic product within the microneedle openings, can influence the stable response.

For example, in the disclosed embodiment, the coupling of CPE transducers with microneedle hosts was shown to provide low-potential detection of $H_2O_2$. For example, exemplary implementations of the disclosed embodiment demonstrated that a reproducible amperometric response can be achieved following successive reconstitution of the carbon paste matrix. For example, exemplary implementations of the disclosed embodiment demonstrated that highly-linear lactate detection can be achieved over the entire physiological range, along with the high selectivity imparted by the very low cathodic detection potential. The high selectivity, sensitivity, and stability of the described CPE microneedle array demonstrates the ability of the array to be implemented in diverse on-body sensing applications.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for in situ measurement of one or more target chemical species present in a physiological fluid, the method comprising:
    causing a microneedle sensing device to contact the physiological fluid, wherein the microneedle sensing device includes a substrate and an array of electrically-conducting electrodes, wherein each electrically-conducting electrode is respectively disposed in a hollow interior of a hollow microneedle of a hollow microneedle array formed on the substrate, one electrode per hollow microneedle, wherein each electrically-conducting electrode has a tip located inside the hollow interior of its respective hollow microneedle to form a recess microcavity that surrounds the electrode within the hollow interior, wherein the tip is coated to be functionalized for interacting with one or more target chemical species present in a portion of the physiological fluid that is trapped in its respective recess microcavity;
    applying a stimulus signal to an electrically conductive structure disposed on the substrate that is coupled to the array of electrically-conducting electrodes to cause biosensing of the physiological fluid entrapped in each recess microcavity; and
    reading a resultant signal arising at an interface between the physiological fluid and the coated tip of the electrically-conducting electrode in each recess microcavity as part of the in situ measurement,
    wherein a property of said resultant signal is indicative of a concentration of the one or more target chemical species present in said physiological fluid.

2. The method according to claim 1, comprising:
    processing the resultant signal to determine whether the concentration of the one or more target chemical species present in said physiological fluid reflects a healthy or disease state.

3. The method according to claim 2, wherein processing the resultant signal includes comparing the resultant signal to a threshold value.

4. The method according to claim 2, wherein processing the resultant signal includes determining a pattern in the resultant signal.

5. The method according to claim 1, wherein the property of said resultant signal includes magnitude of the resultant signal.

6. The method according to claim 1, wherein the property of said resultant signal includes an impedimetric property.

7. A device for in situ measurement of one or more target chemical species present in a physiological fluid, the device comprising:
    a substrate;
    a hollow microneedle array of hollow microneedles formed on one side of the substrate, each hollow microneedle including a hollow interior;
    an array of electrically-conducting electrodes, wherein each electrically-conducting electrode is respectively disposed in the hollow interior of one of the hollow microneedle, one electrode per hollow microneedle, wherein each electrically-conducting electrode has a tip located inside the hollow interior of its respective hollow microneedle to form a recess microcavity that surrounds the electrode within the hollow interior, wherein the tip is coated to be functionalized for interacting with one or more target chemical species present in a portion of the physiological fluid that is trapped in its respective recess microcavity;
    an electrically conductive structure disposed on the substrate, wherein the conductive structure is configured to receive an excitation signal and is electrically connected with each of the electrodes to cause electrochemical sensing of a portion of the physiological fluid that is trapped in each recess microcavity.

8. The device of claim 7, wherein the device is configured to measure a resultant signal at an interface between each electrode and the physiological fluid; and
    wherein a property of said resultant signal is indicative of a concentration of the one or more target chemical species present in said physiological fluid.

9. The device according to claim 8, wherein the property of said resultant signal includes magnitude of the resultant signal.

10. The device according to claim 8, wherein the property of said resultant signal includes an impedimetric property.

11. The device according to claim 7, wherein said array of hollow microneedles include at least one of a conal, columnar, triangular, pyramidal, rectangular, or polygonal geometric shape.

12. The device according to claim 7, wherein each microneedle is made of a polymer.

13. The device according to claim 7, wherein said substrate is planar and comprises one of a polymer, semiconductor, metal, glass, or film.

14. The device according to claim 7, wherein each tip is functionalized by a chemical species-selective layer deposited on a surface of said tip and facilitates quantification of the target species.

15. The device according to claim 14, wherein said chemical species includes one of a metabolite, electrolyte, ion, pathogen, microorganism, hormone, protein, enzyme, vitamin, anti-oxidant, nucleic acid, antibodies, neurotransmitter, acid, or drug.

16. The device according to claim 14, wherein the chemical species-selective layer comprises one of an ion-selective membrane, enzyme-loaded membrane, conducting polymer, diffusion-limiting polymer, electrostatically-bound biocatalyst, covalently-bound biocatalyst, or surface-adsorbed biocatalyst.

17. The device according to claim 7, wherein said physiological fluid includes liquids originating from a living human body and lying beneath biological tissues or membranes.

18. The device according to claim 7, wherein the physiological fluid comprises one of interstitial fluid, intracellular fluid, extracellular fluid, blood, plasma, serum, cerebrospinal fluid, mucus, intraocular, or vitreous humor.

19. The device according to claim 7, wherein the electrically-conducting electrodes comprise a platinum coating.

20. The device according to claim 7, wherein each microneedle extends from the substrate to a distance of between 20 to 1500 micrometers.

* * * * *